US010519296B2

(12) United States Patent
Arendt et al.

(10) Patent No.: US 10,519,296 B2
(45) Date of Patent: Dec. 31, 2019

(54) POLYESTER PLASTICIZERS WITH BENZOIC ACID END-CAPS

(71) Applicant: EMERALD KALAMA CHEMICAL, LLC, Kalama, WA (US)

(72) Inventors: William D. Arendt, Libertyville, IL (US); Emily McBride, Kalama, WA (US); Steven D. Roth, Ridgefield, WA (US); Eric Hatcher, Monmouth, OR (US)

(73) Assignee: EMERALD KALAMA CHEMICAL, LLC, Kalama, WA (US)

( * ) Notice: Subject to any disclaimer, the term of this patent is extended or adjusted under 35 U.S.C. 154(b) by 338 days.

(21) Appl. No.: 15/109,339

(22) PCT Filed: Jan. 2, 2015

(86) PCT No.: PCT/US2015/010019
§ 371 (c)(1),
(2) Date: Jun. 30, 2016

(87) PCT Pub. No.: WO2015/103460
PCT Pub. Date: Jul. 9, 2015

(65) Prior Publication Data
US 2016/0326345 A1 Nov. 10, 2016

Related U.S. Application Data

(60) Provisional application No. 62/067,573, filed on Oct. 23, 2014, provisional application No. 61/922,906, filed on Jan. 2, 2014.

(51) Int. Cl.
*C08K 5/11* (2006.01)
*C08L 27/06* (2006.01)
*C08K 5/00* (2006.01)
*C07C 67/08* (2006.01)
*C07C 69/78* (2006.01)
*C08G 63/12* (2006.01)
*C08G 63/20* (2006.01)
*C09J 11/06* (2006.01)
*C09K 3/10* (2006.01)
*C09J 7/24* (2018.01)

(52) U.S. Cl.
CPC ............... *C08K 5/11* (2013.01); *C07C 67/08* (2013.01); *C07C 69/78* (2013.01); *C08G 63/12* (2013.01); *C08G 63/20* (2013.01); *C08K 5/0016* (2013.01); *C08L 27/06* (2013.01); *C09J 7/245* (2018.01); *C09J 11/06* (2013.01); *C09K 3/1012* (2013.01); *C09J 2201/606* (2013.01); *C09J 2203/334* (2013.01); *C09J 2205/106* (2013.01); *C09J 2427/006* (2013.01)

(58) Field of Classification Search
CPC ...... C08K 5/0016; C08K 5/11; C09K 3/1012; C07C 67/08; C07C 69/78; C08G 63/12; C08G 63/20; C09J 11/06; C09J 7/245; C09J 2427/006; C09J 2205/106; C09J 2203/334; C09J 2201/606; C08L 27/06
USPC ........................................................ 524/299
See application file for complete search history.

(56) References Cited

U.S. PATENT DOCUMENTS

| 4,135,009 | A | 1/1979 | Mercurio |
| 5,412,894 | A | 5/1995 | Sizensky et al. |
| 2005/0106967 | A1* | 5/2005 | Suzuki .................... B32B 27/12 442/86 |
| 2009/0088513 | A1* | 4/2009 | Yukino .................... C08K 3/34 524/450 |
| 2010/0204401 | A1 | 8/2010 | Marsh et al. |
| 2013/0274396 | A1 | 10/2013 | Arendt et al. |
| 2015/0135990 | A1† | 5/2015 | Harada |

FOREIGN PATENT DOCUMENTS

| JP | 04-185634 A † | 7/1992 | |
| JP | 05-017684 A † | 1/1993 | |
| JP | 05-117528 A † | 5/1993 | |
| JP | 2004196895 A | 7/2004 | |
| JP | 2012-177018 A † | 9/2012 | |
| JP | 2013-234273 A † | 11/2013 | |
| WO | WO-2013168713 A1 * | 11/2013 | ................ C08J 3/18 |

OTHER PUBLICATIONS

Australian Examination Report No. 2, dated Aug. 29, 2019.

* cited by examiner
† cited by third party

*Primary Examiner* — Angela C Scott
(74) *Attorney, Agent, or Firm* — Hudak, Shunk & Farine Co. LPA

(57) ABSTRACT

Polyester plasticizer compositions for adhesives, caulk, sealants, vinyl and other polymeric compositions comprising low molecular weight oligomeric dibenzoates prepared by end-capping a polyester plasticizer, having alternating units of glycols or diols and dibasic acids, with benzoic acid. Methods for preparing oligomeric dibenzoates include steps to reduce or eliminate residual hydroxyl content and improve plasticizer performance by adding acetic anhydride are also disclosed. Propylene glycol adipate and propylene glycol succinate polyesters with benzoic acid end-caps are particularly useful, as are hybrid benzoate/acetate end-capped polyesters formed in the process with acetic anhydride. Caulks, adhesives, sealants, and vinyl compositions comprising the oligomeric end-capped polyesters of the invention are also contemplated.

4 Claims, 47 Drawing Sheets

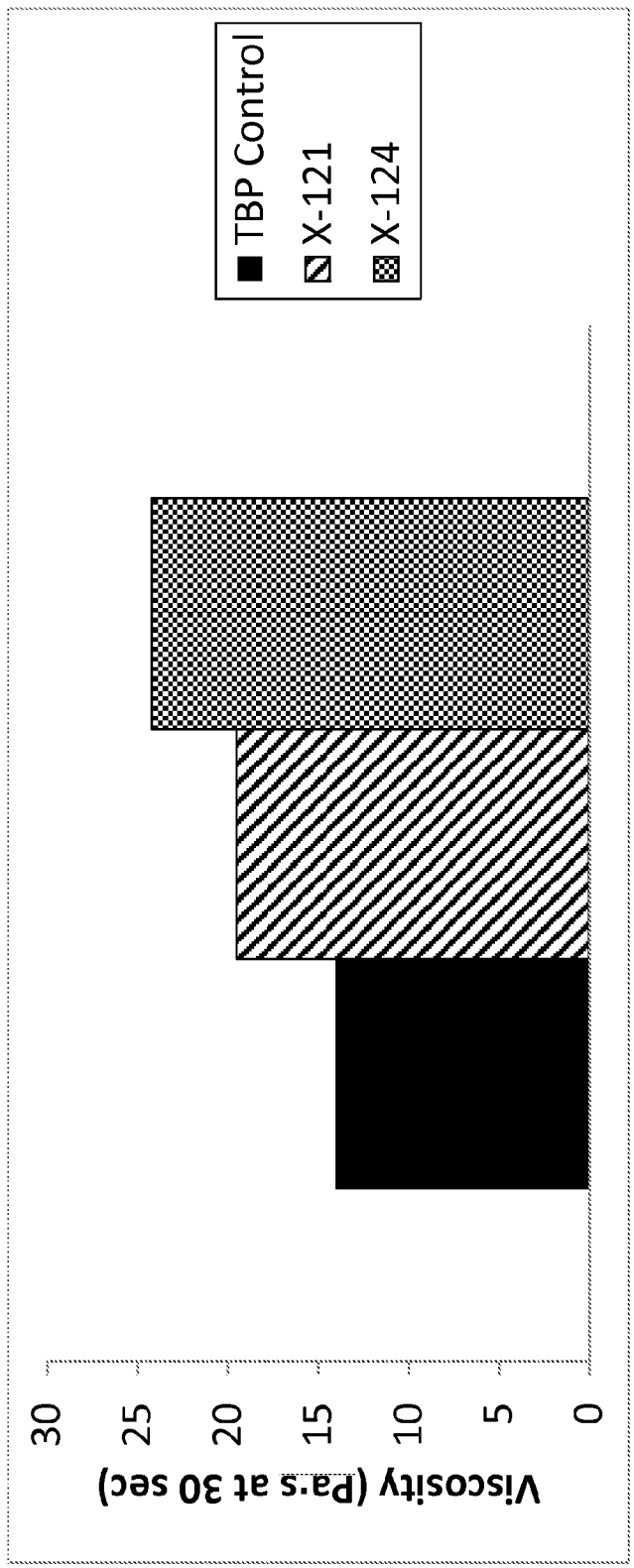
FIG. 1 - B SIDE STEADY SHEAR VISCOSITY (100 s⁻¹)

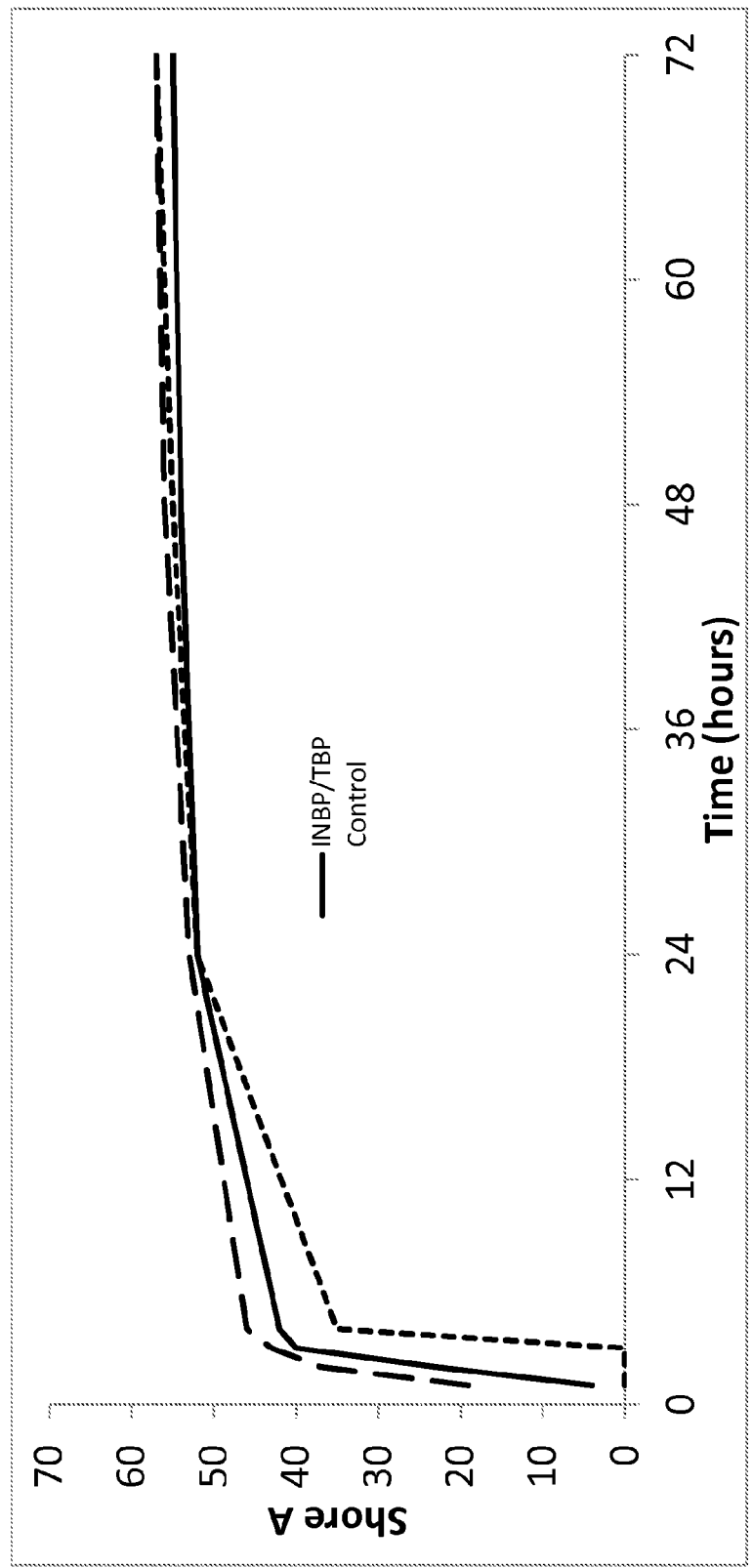

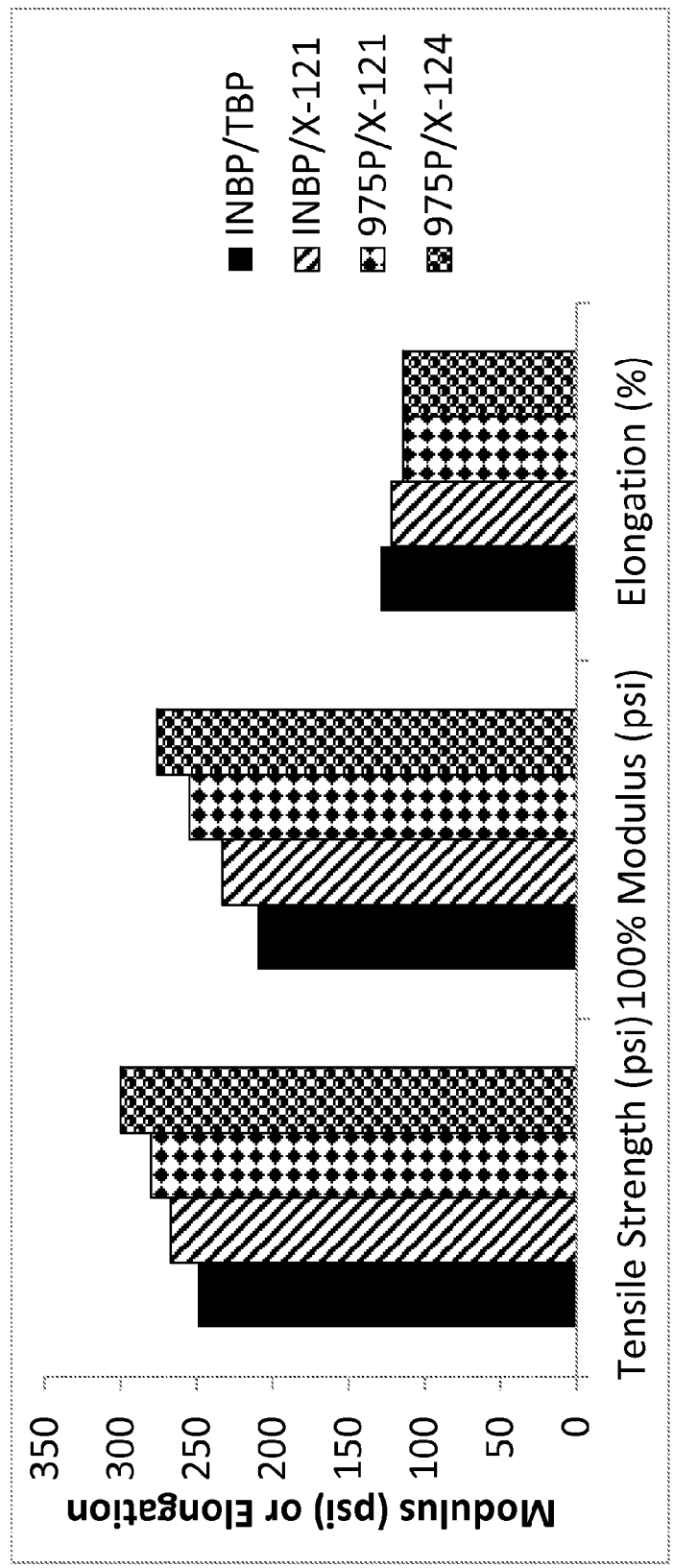

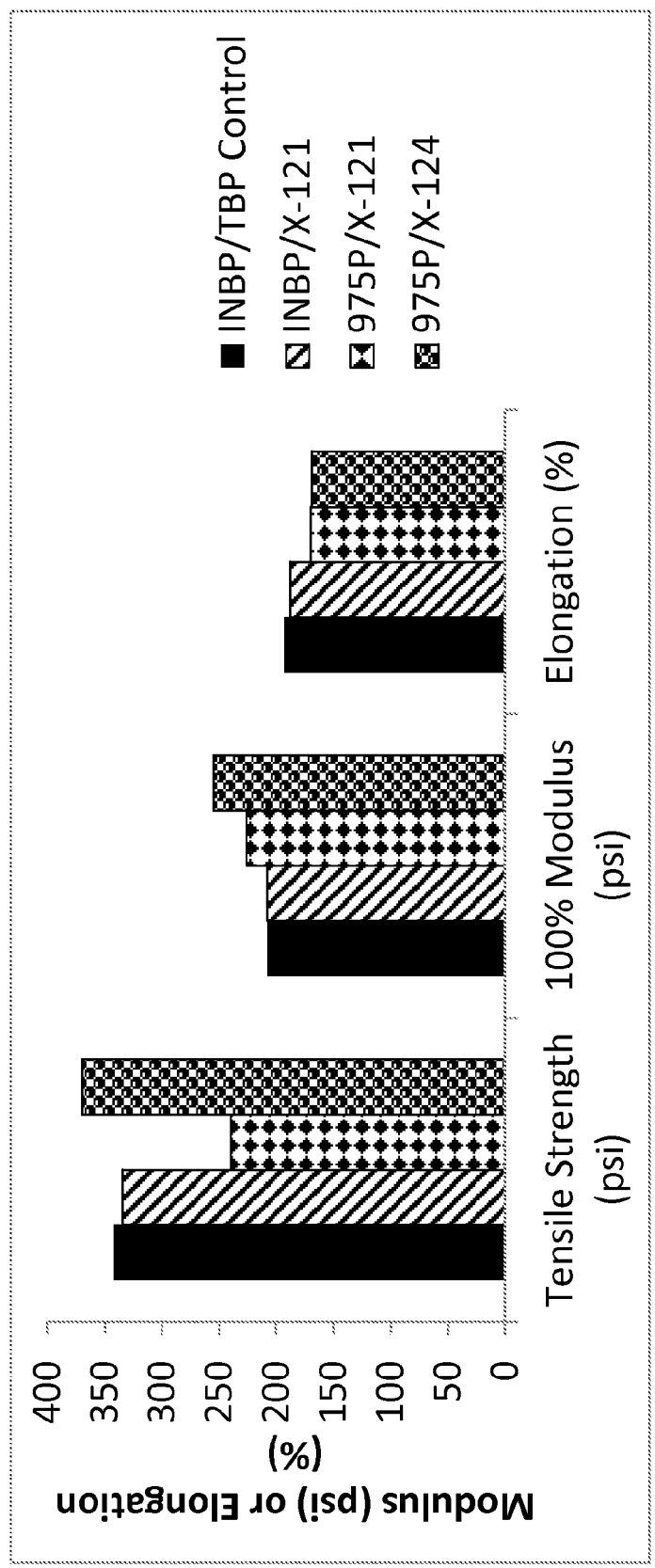

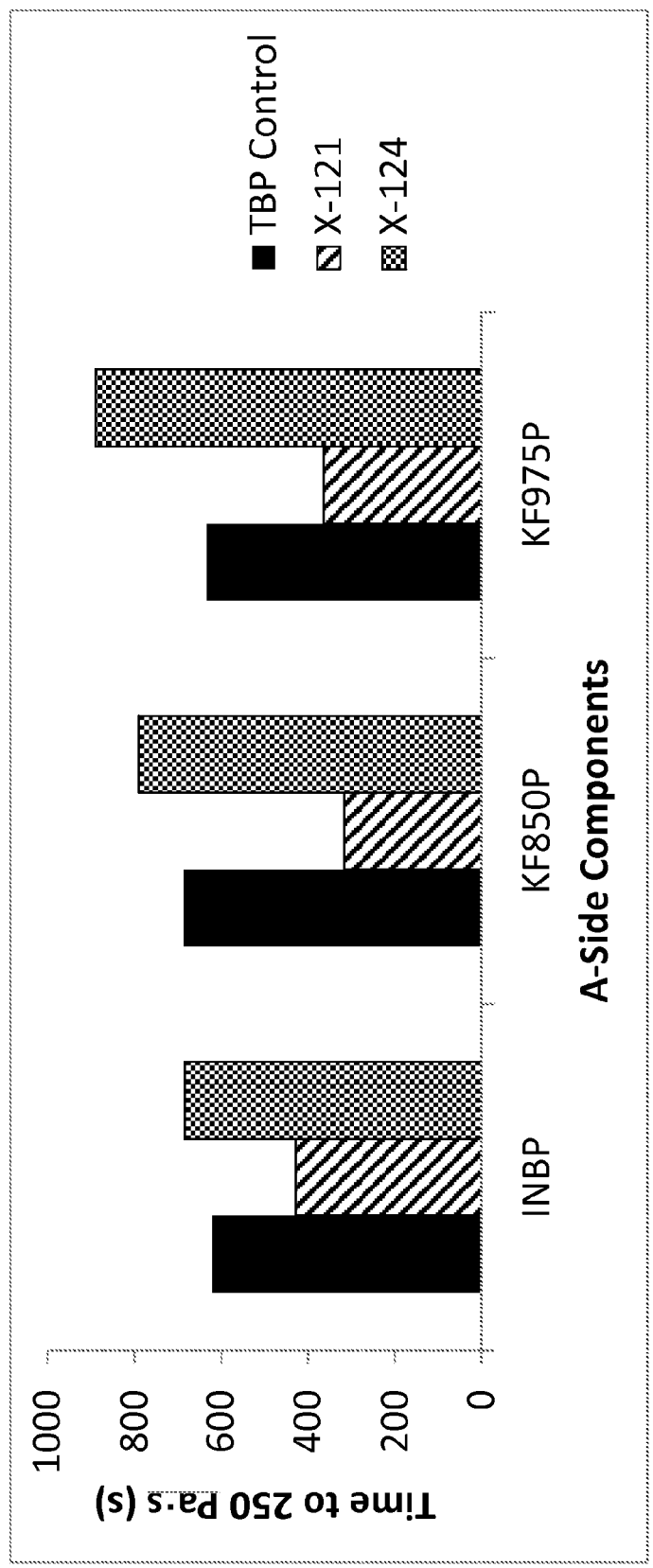

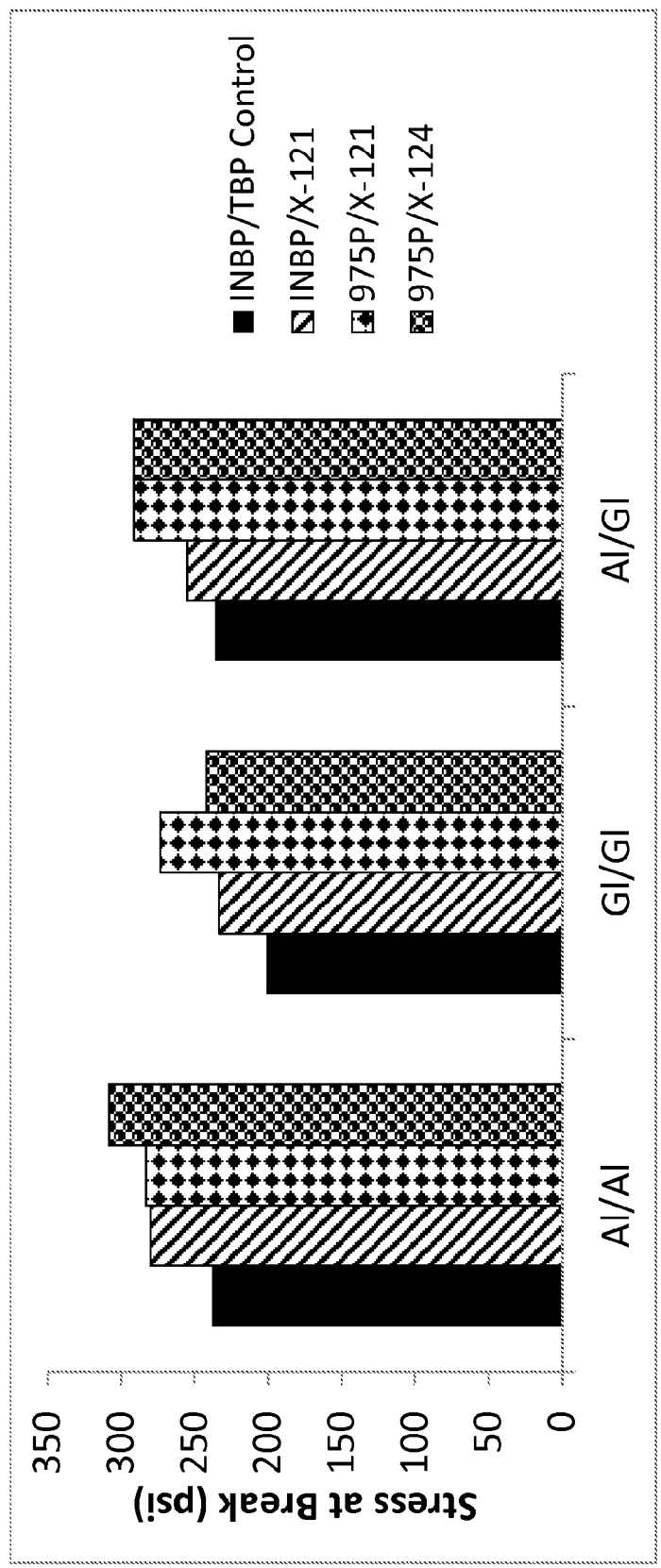
FIG. 6 - LAP SHEAR (ASTM C961)

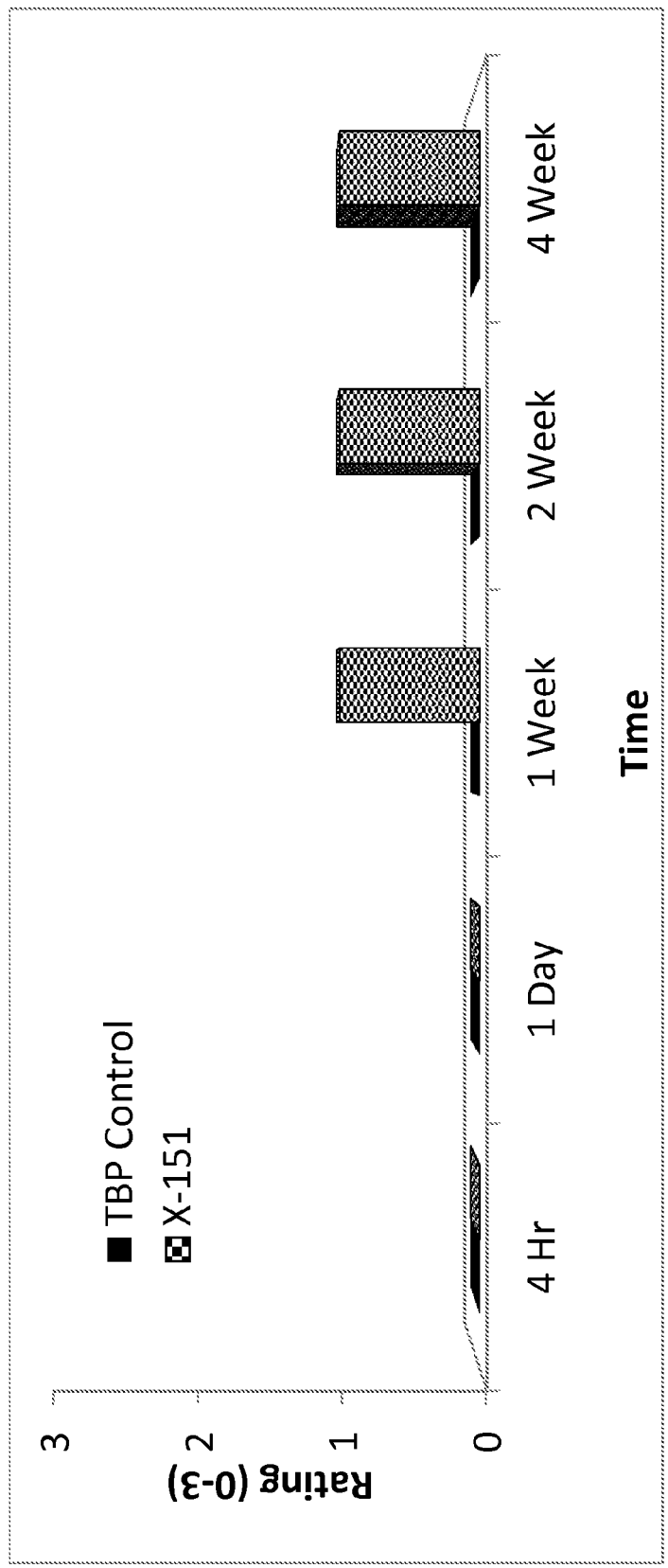

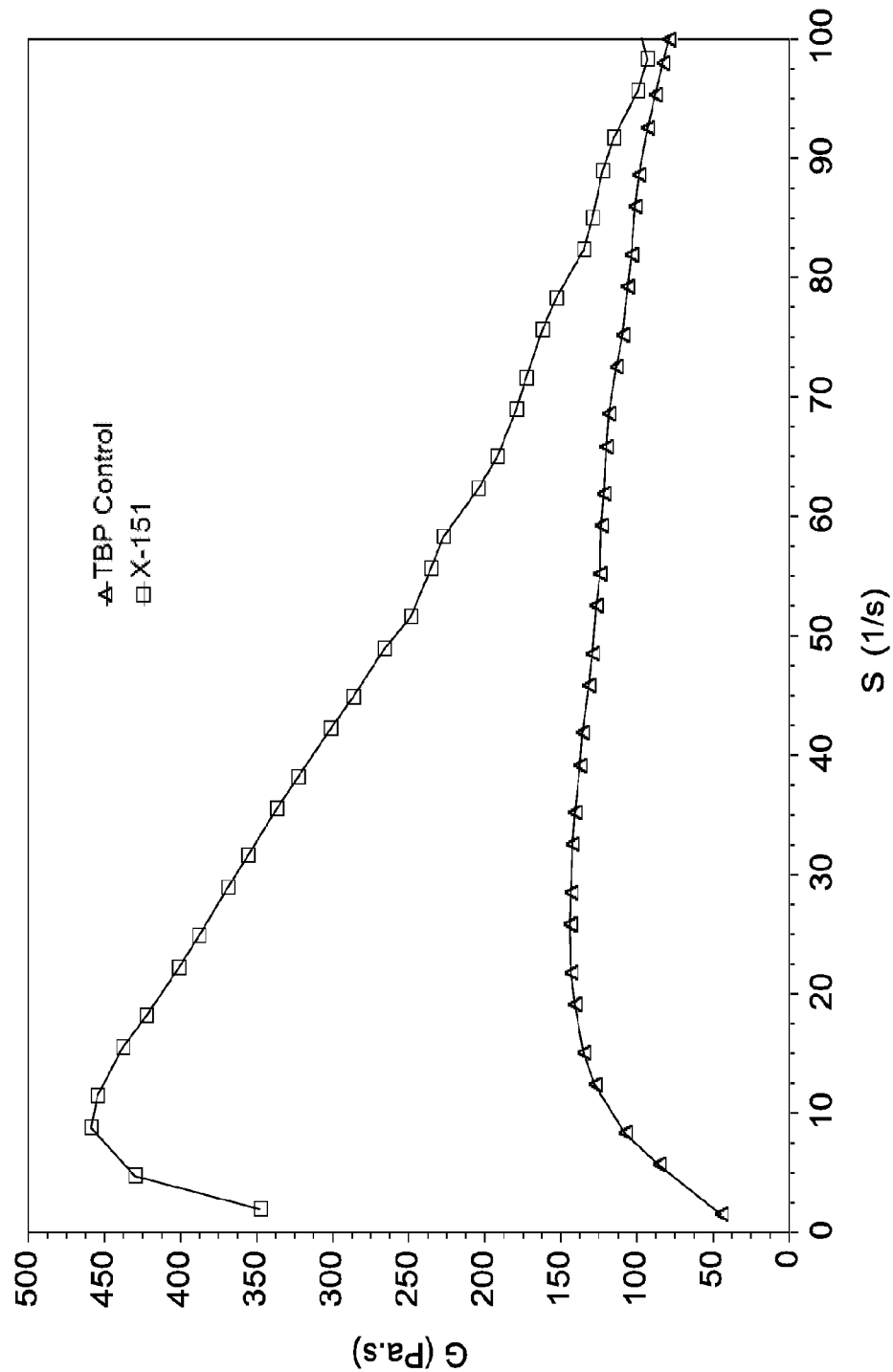

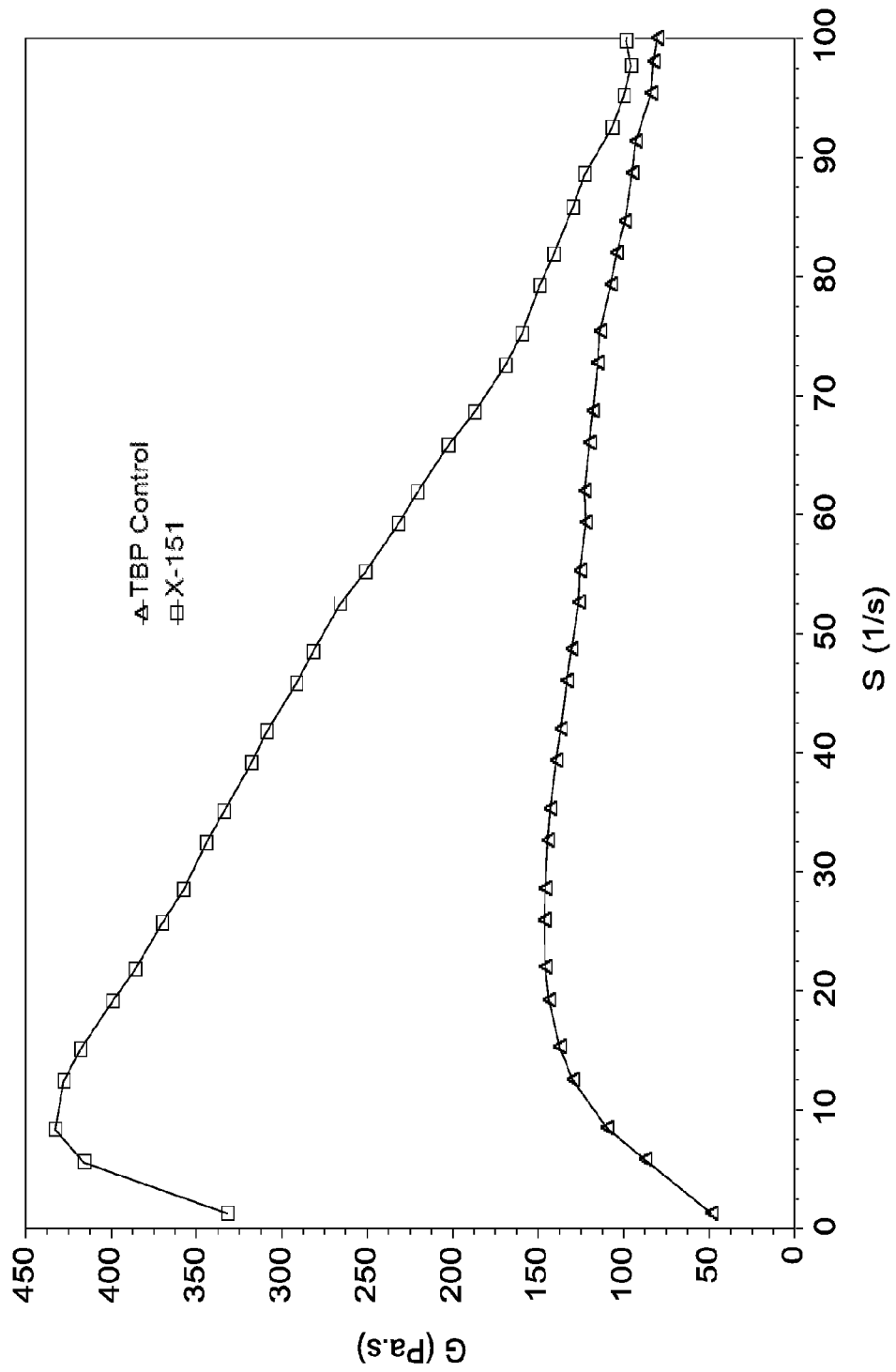

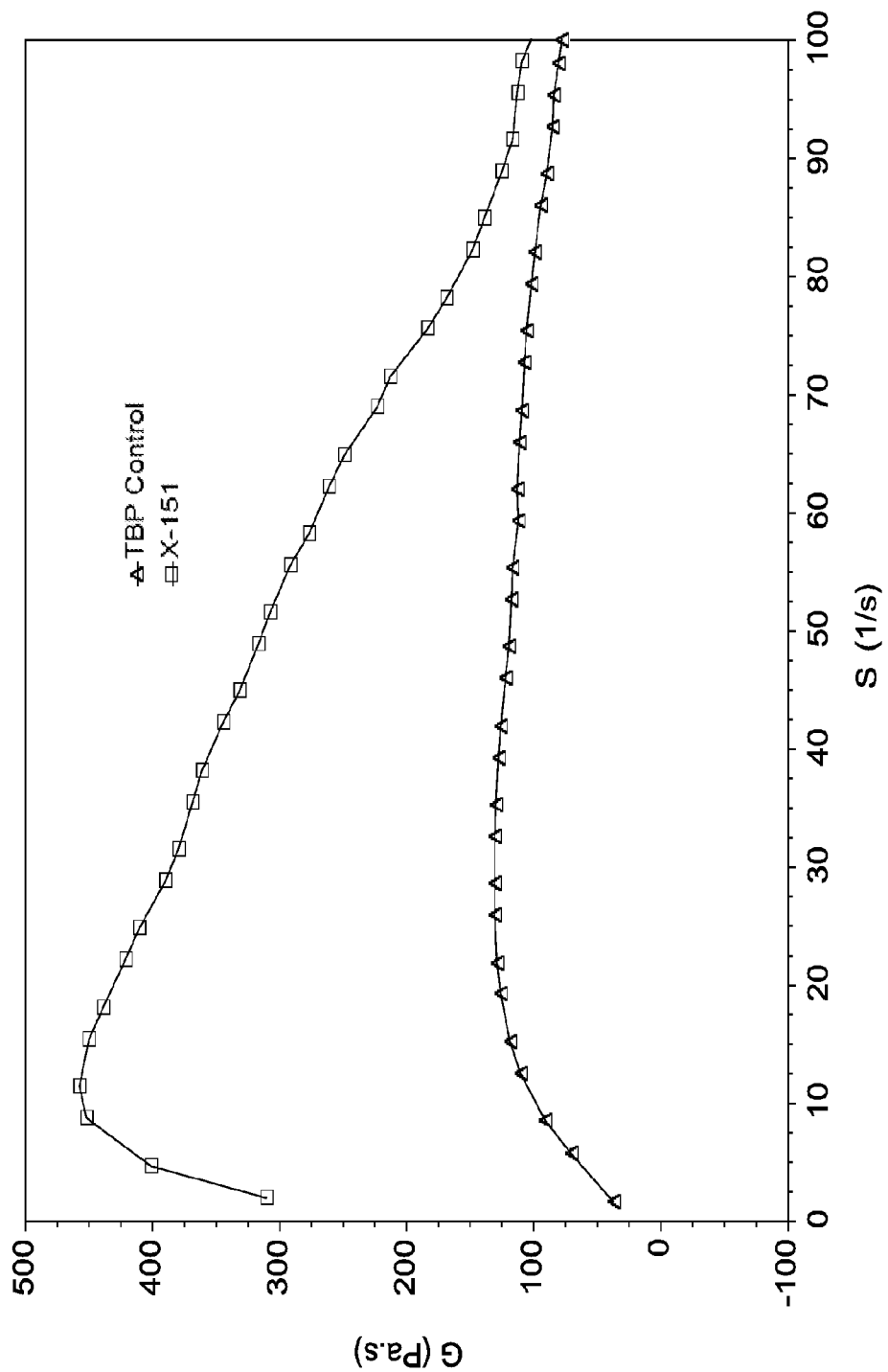
FIG. 10 - THREE DAY SHEAR

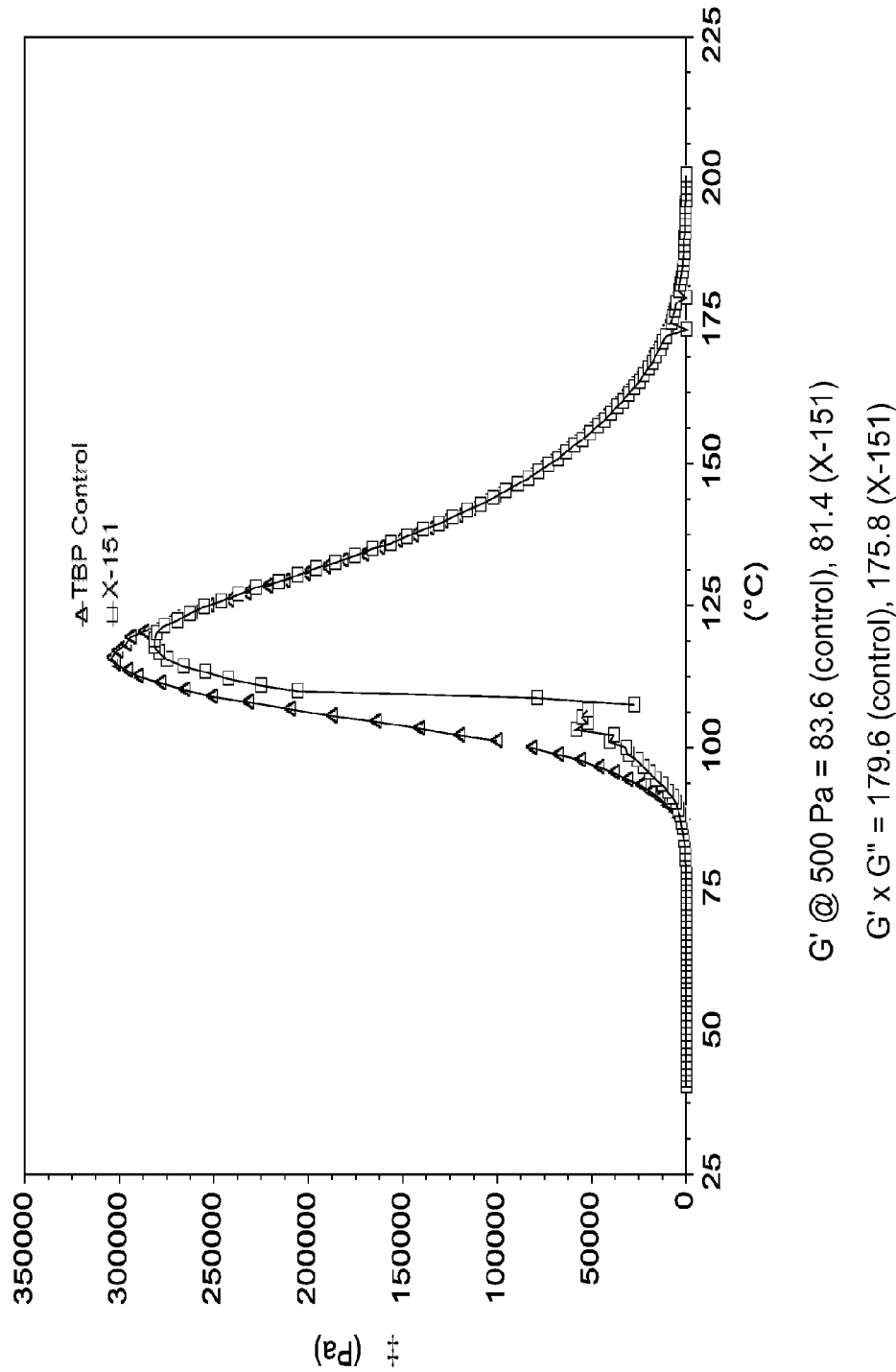

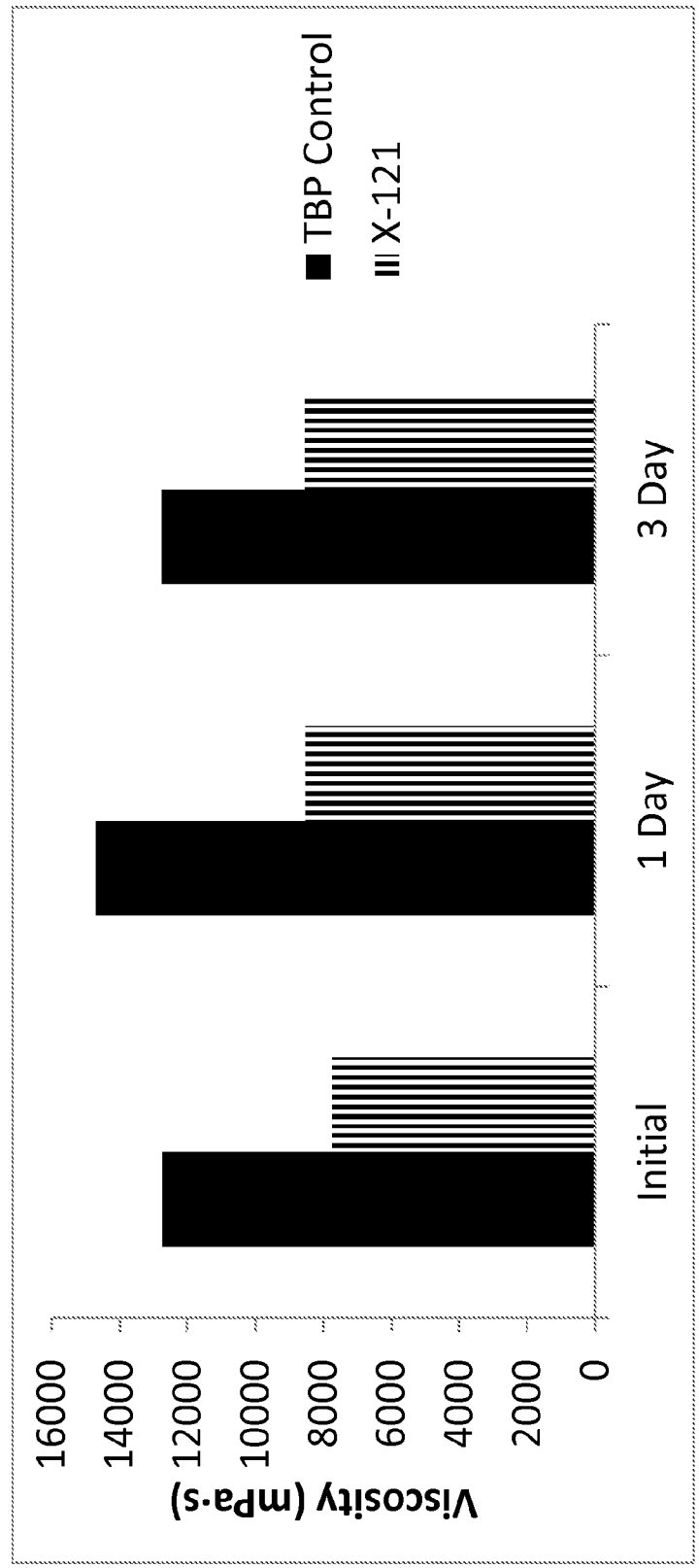

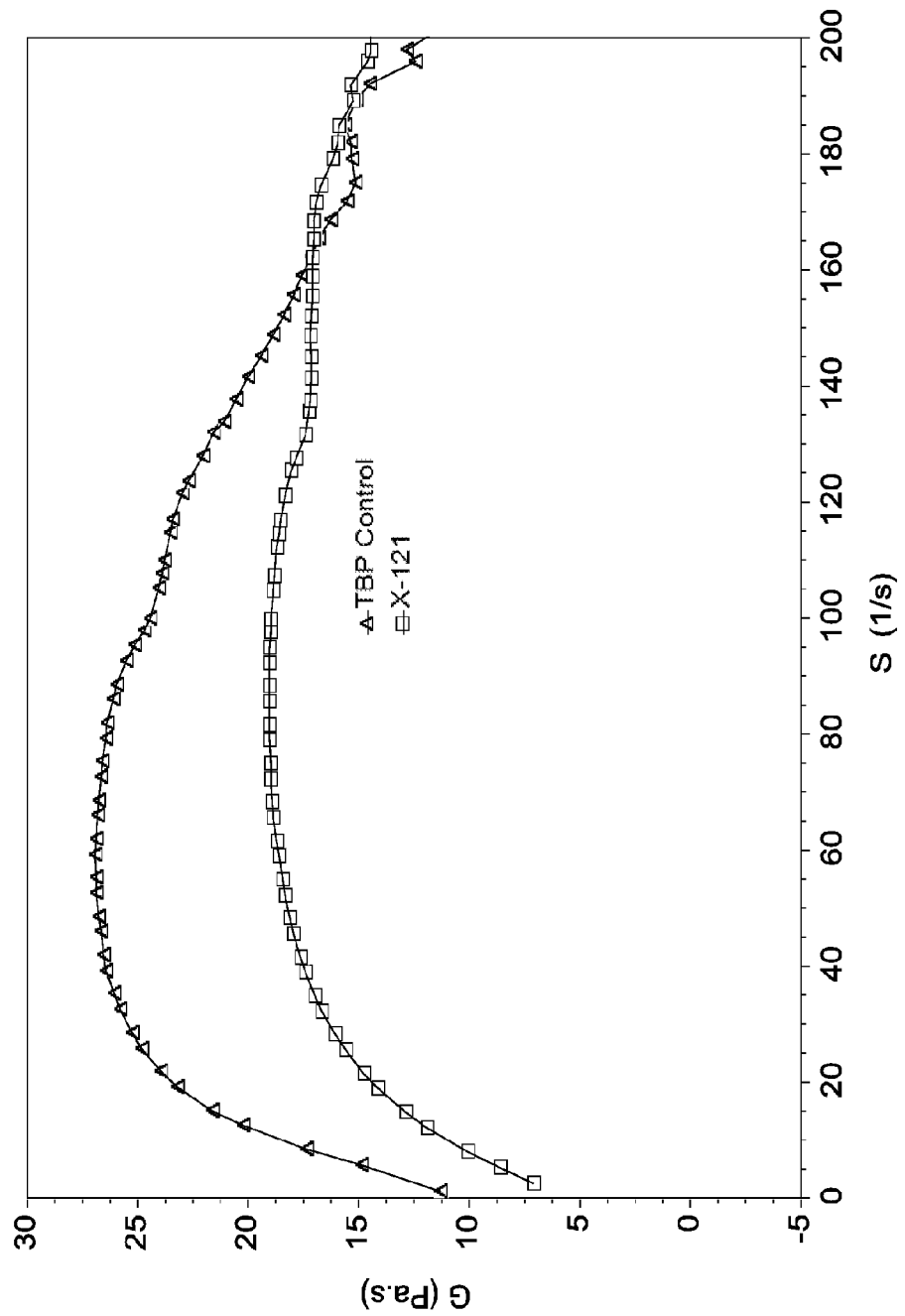

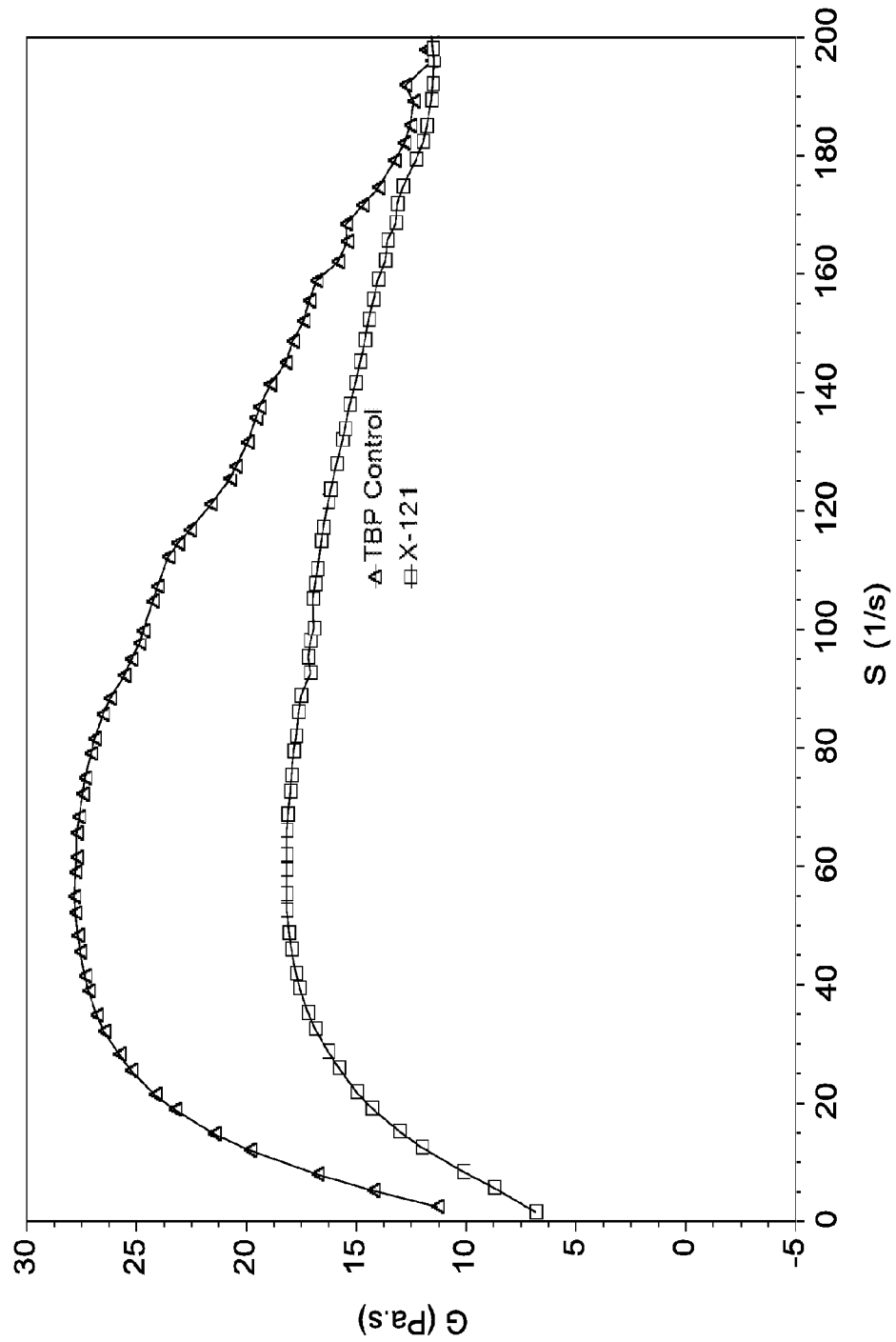

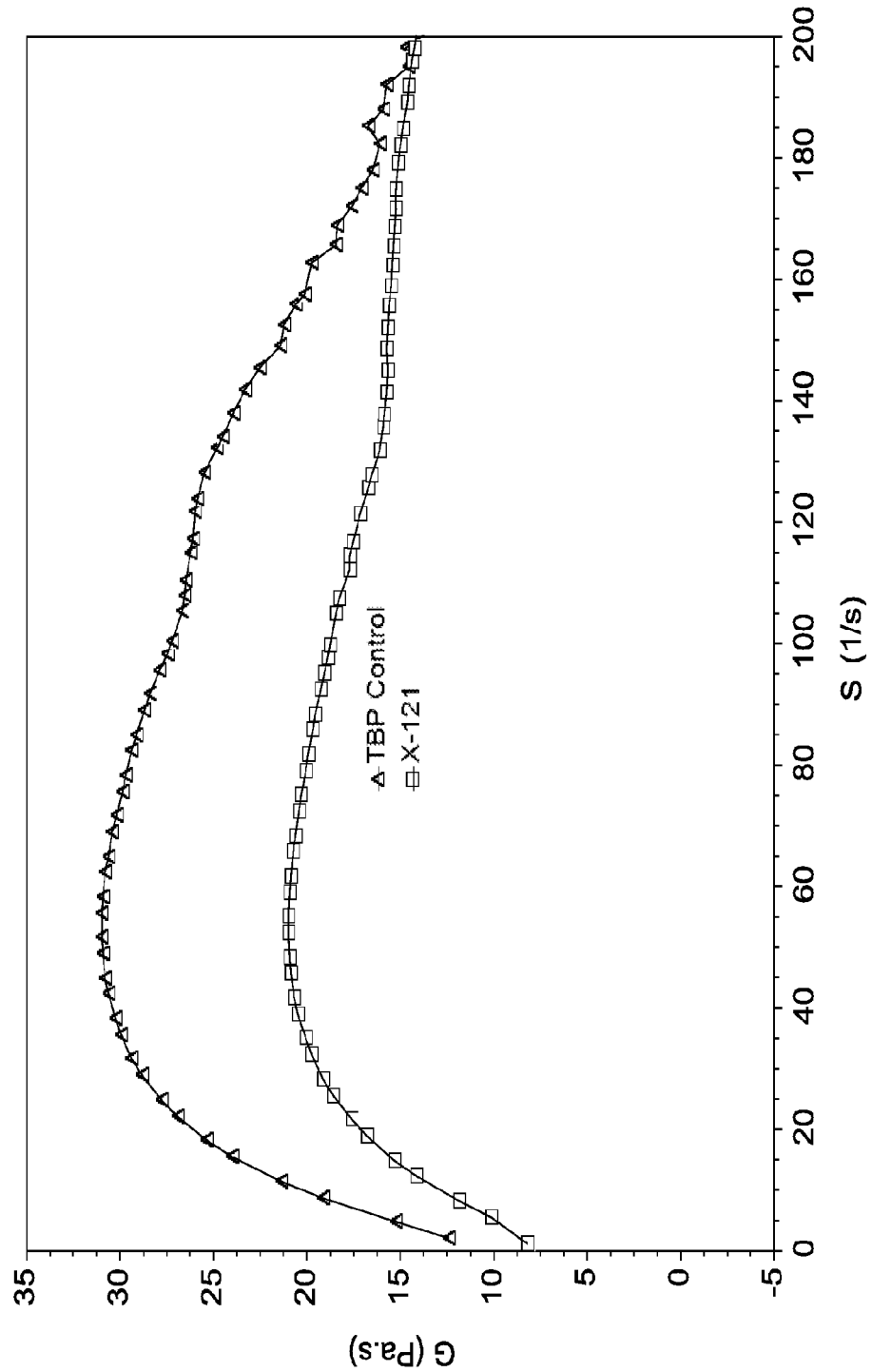

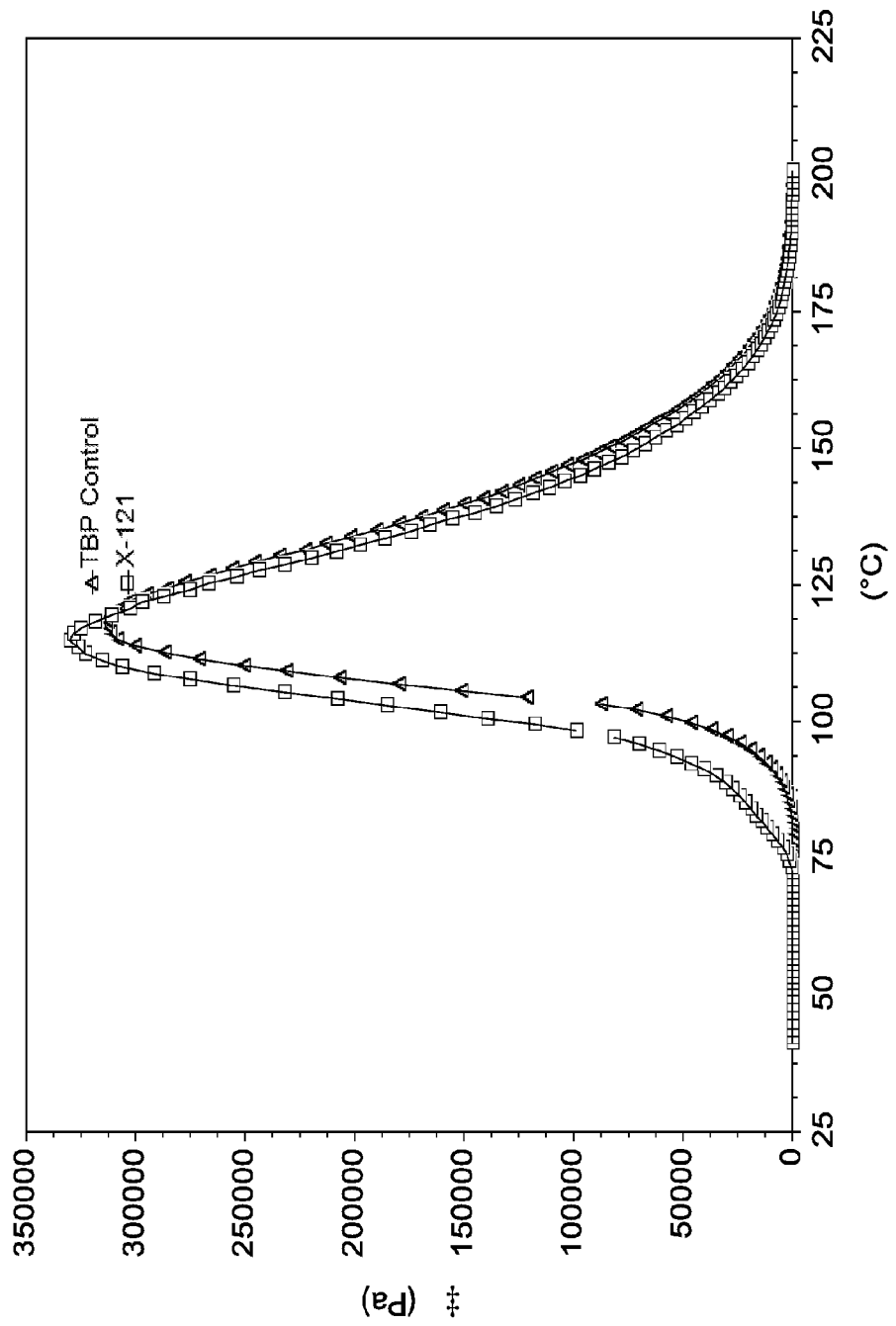

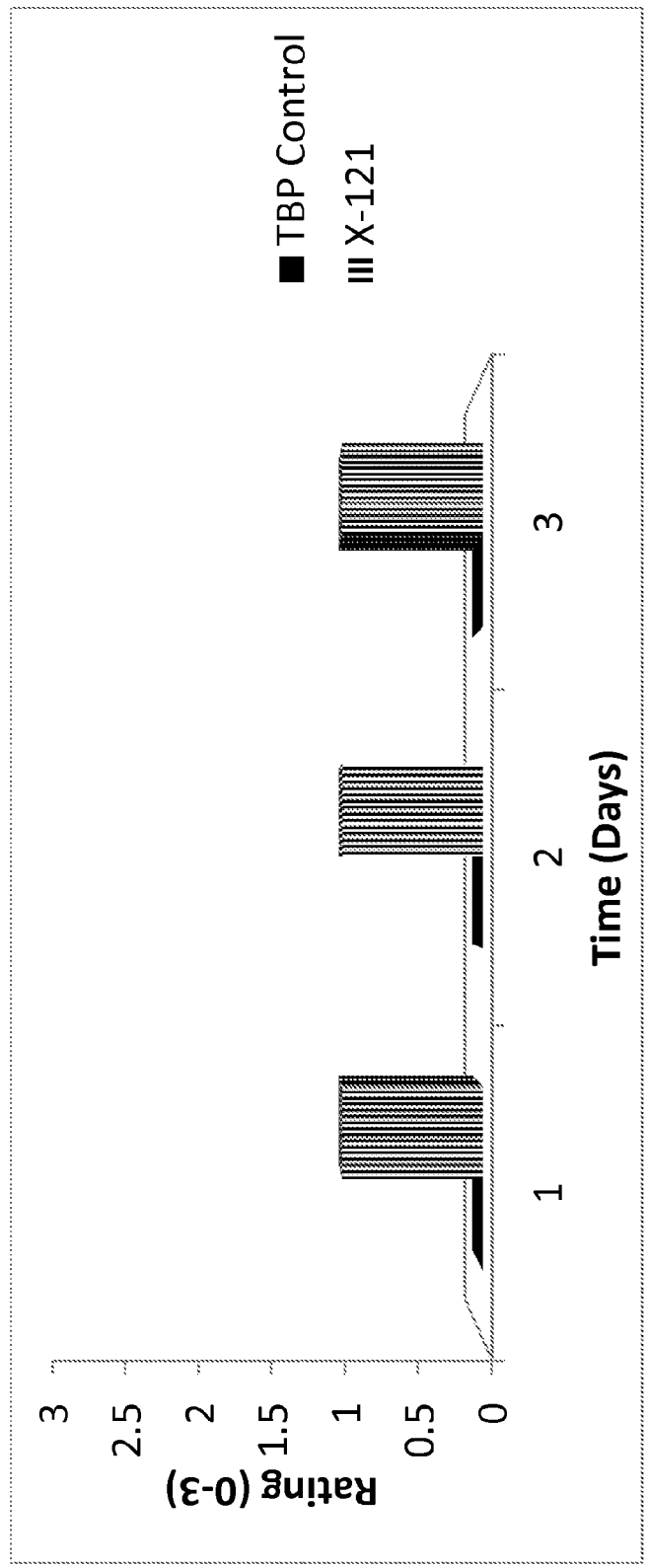
FIG. 17 - COMPATIBILITY, ROLL TEST

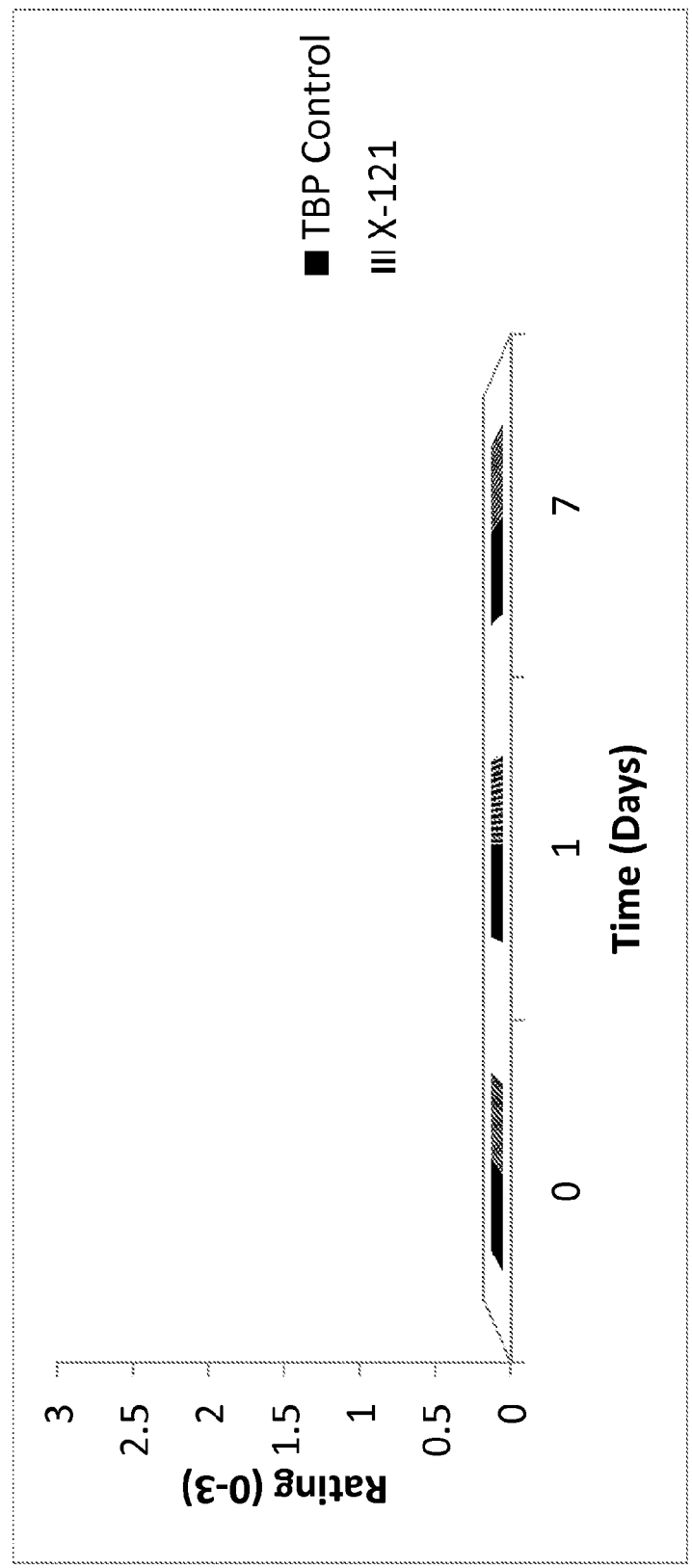
FIG. 18 - COMPATIBILITY, LOOP TEST

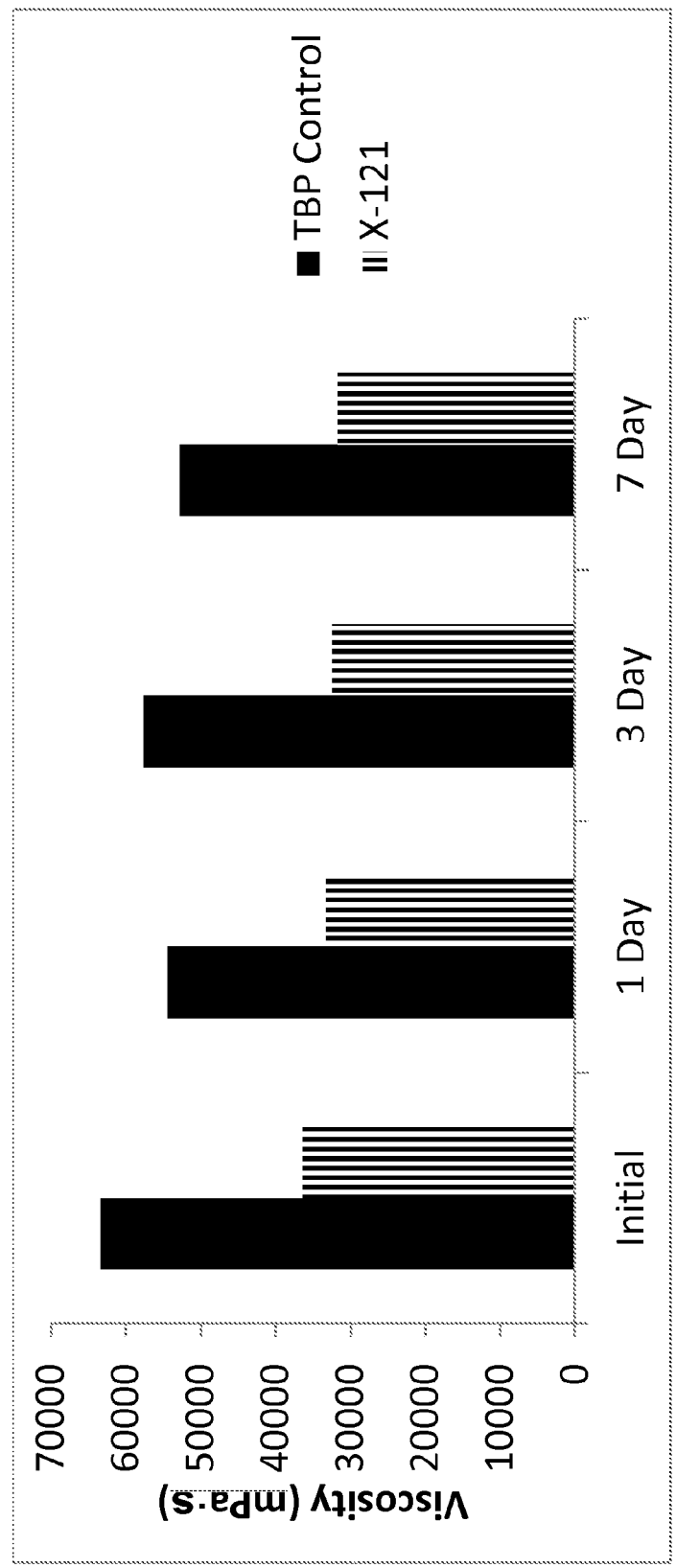

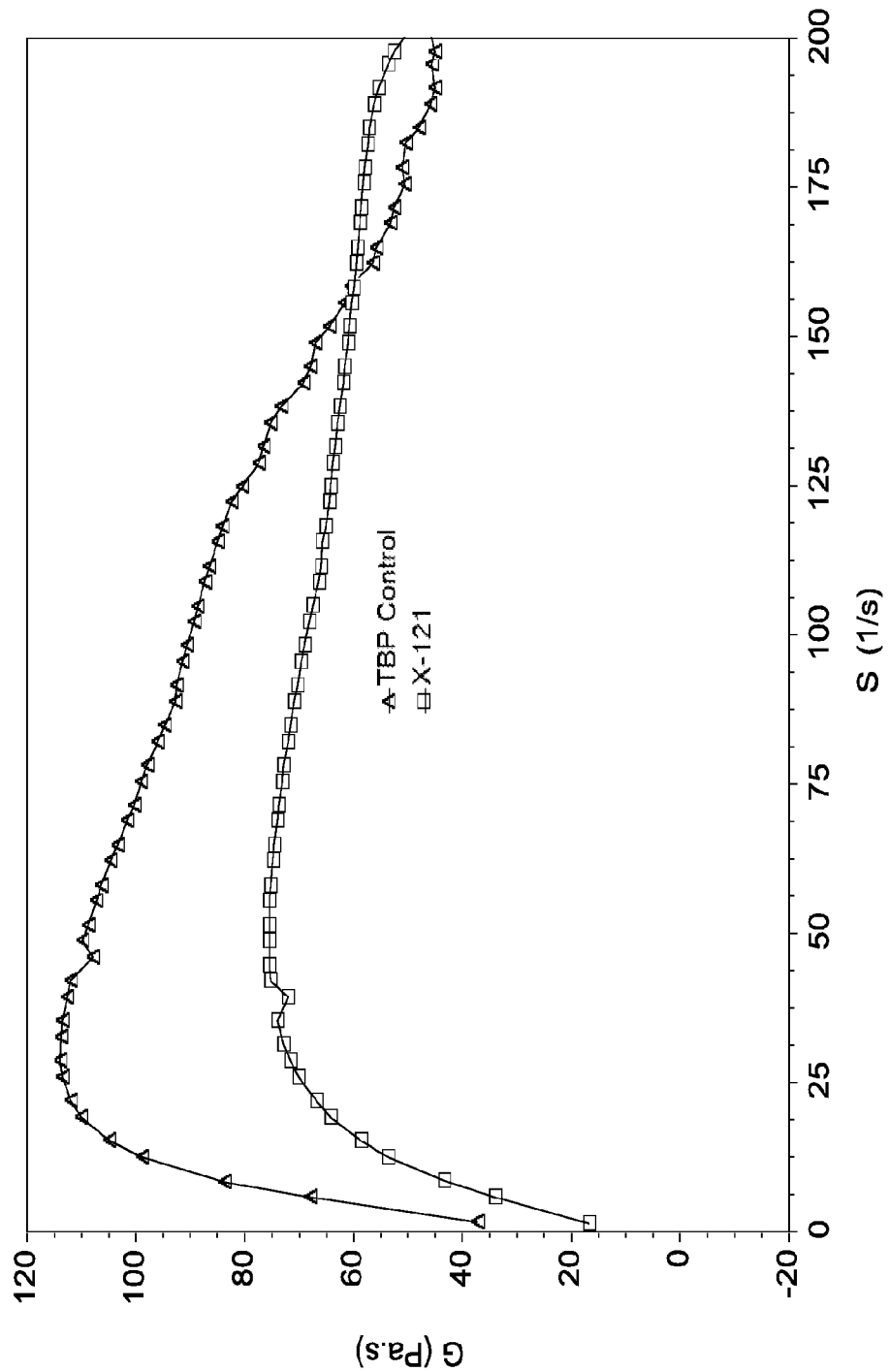

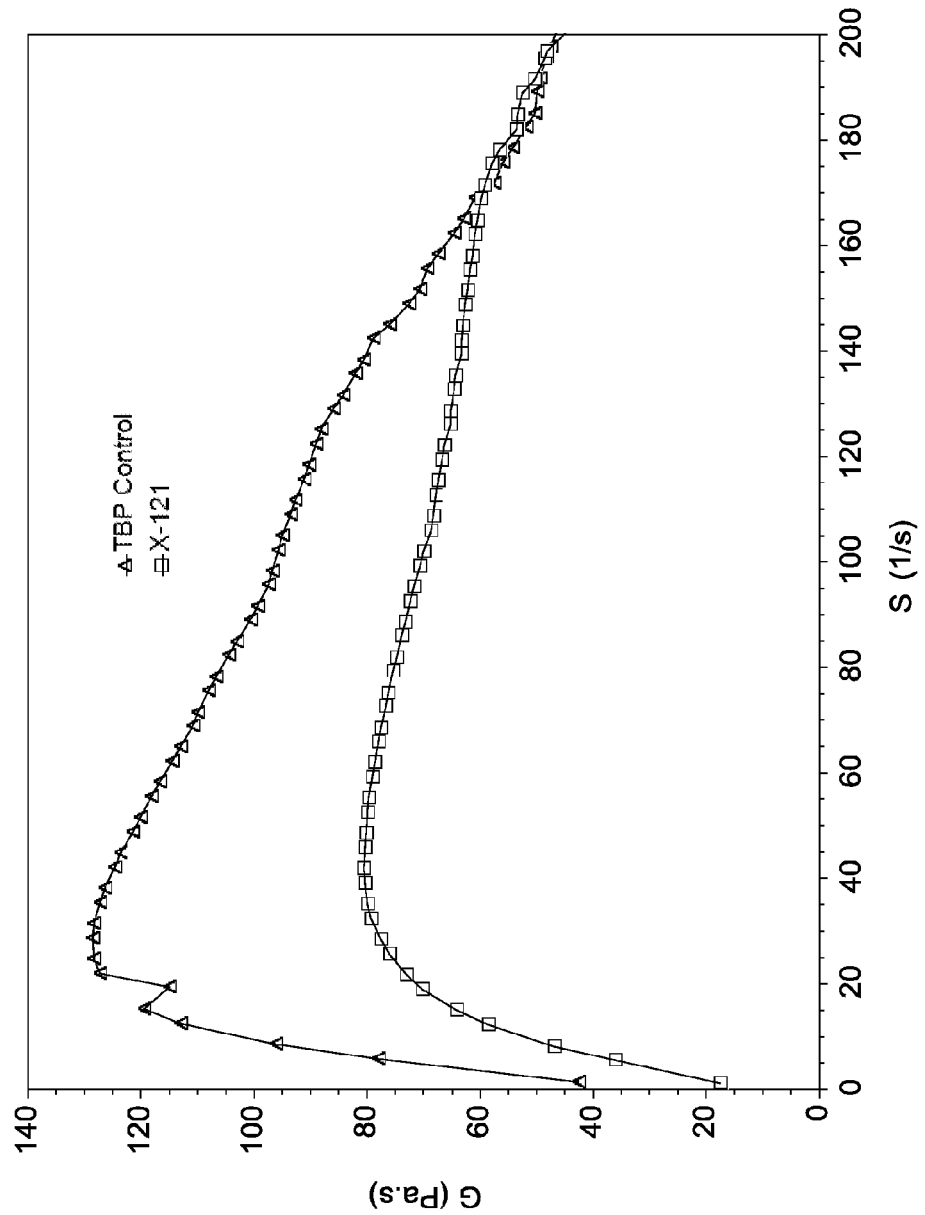
FIG. 21 - ONE DAY SHEAR

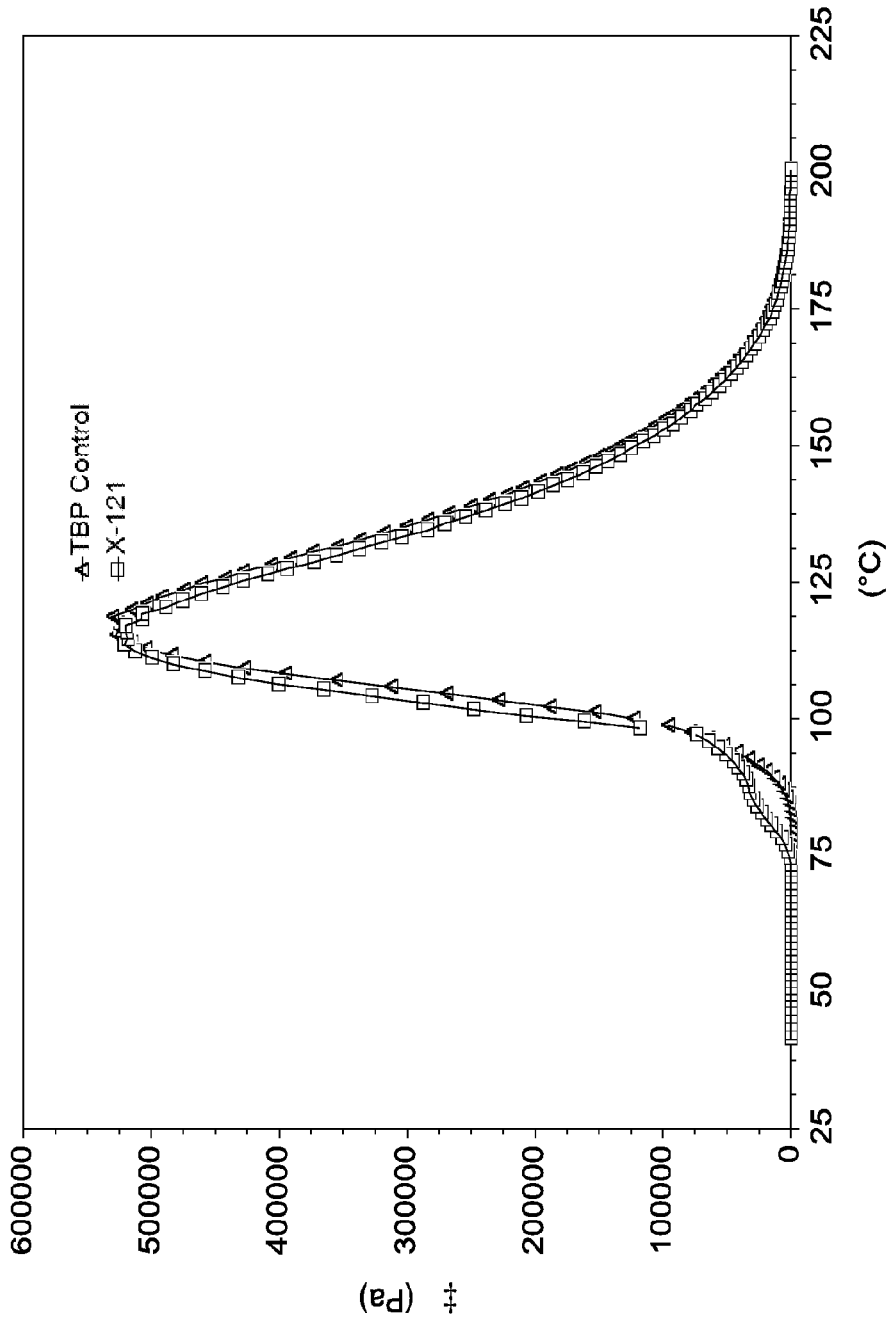

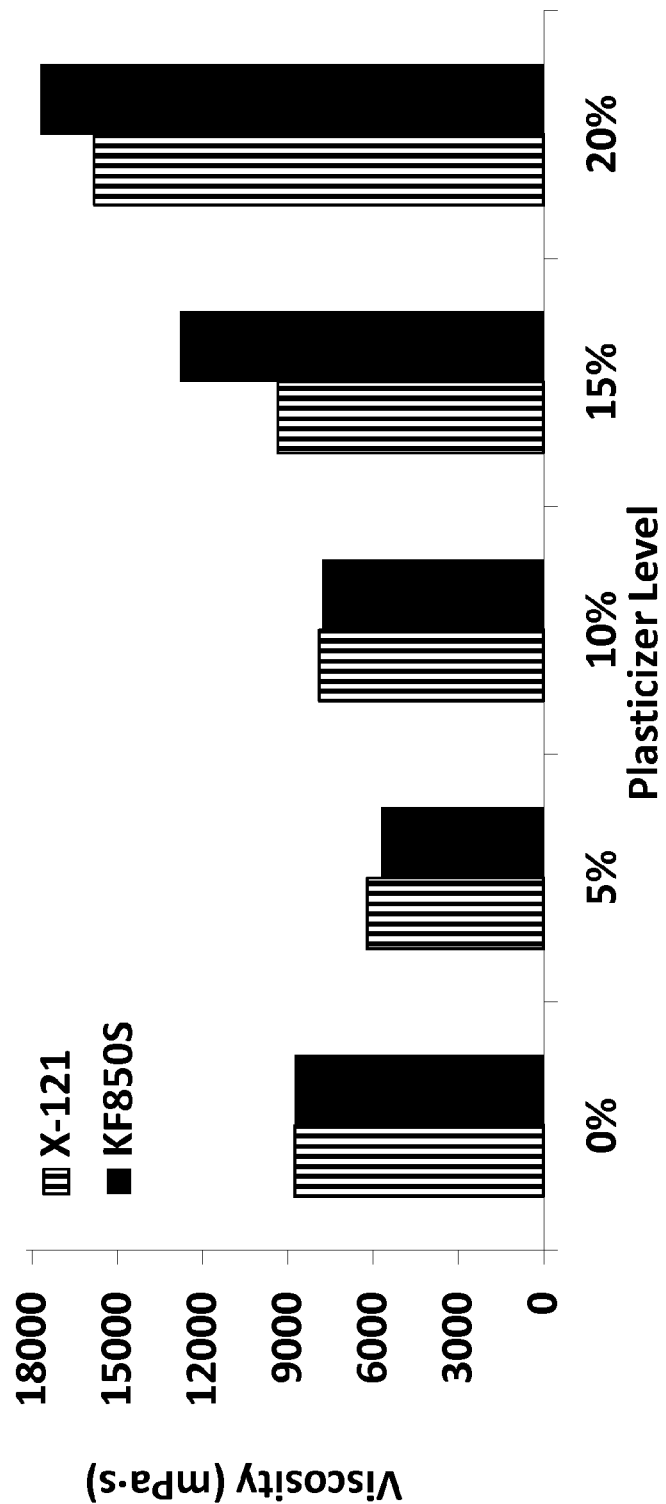

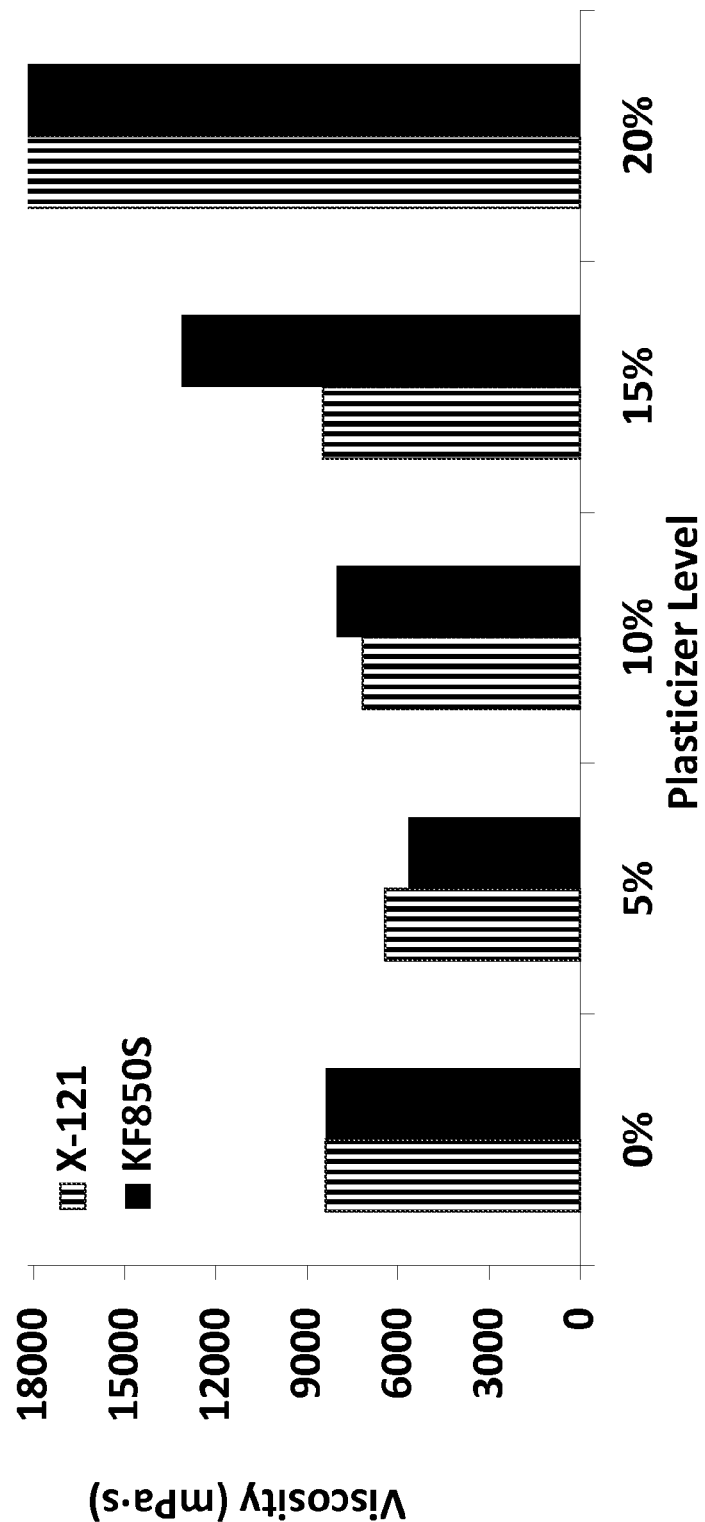

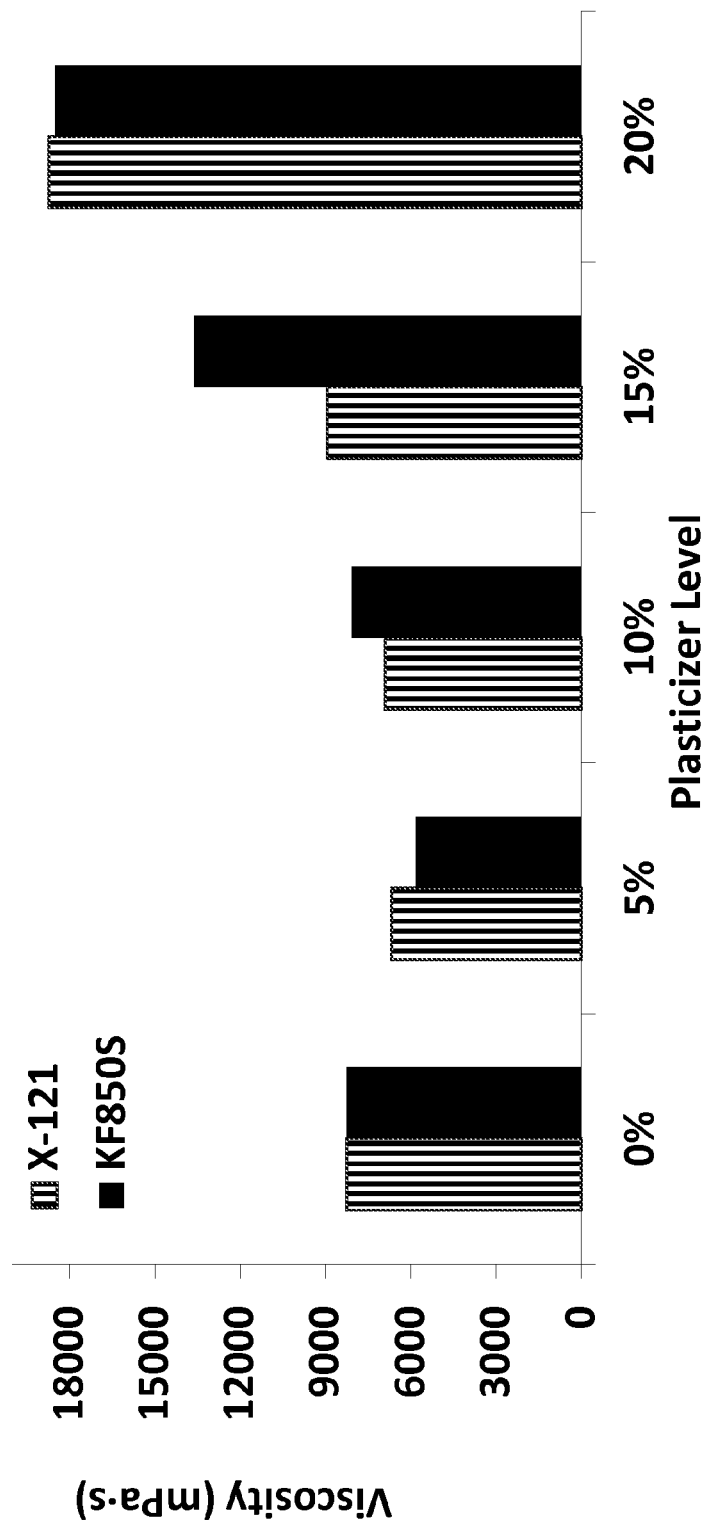

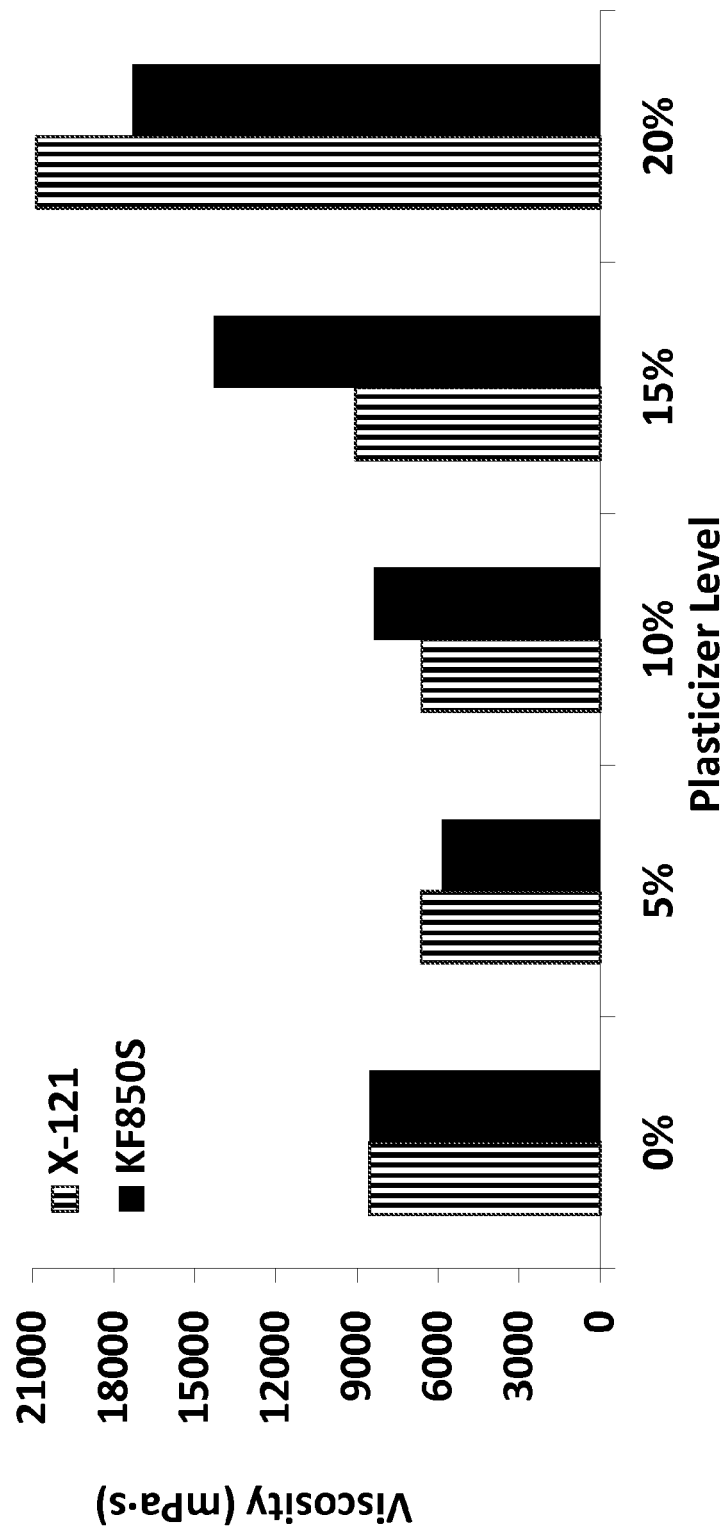

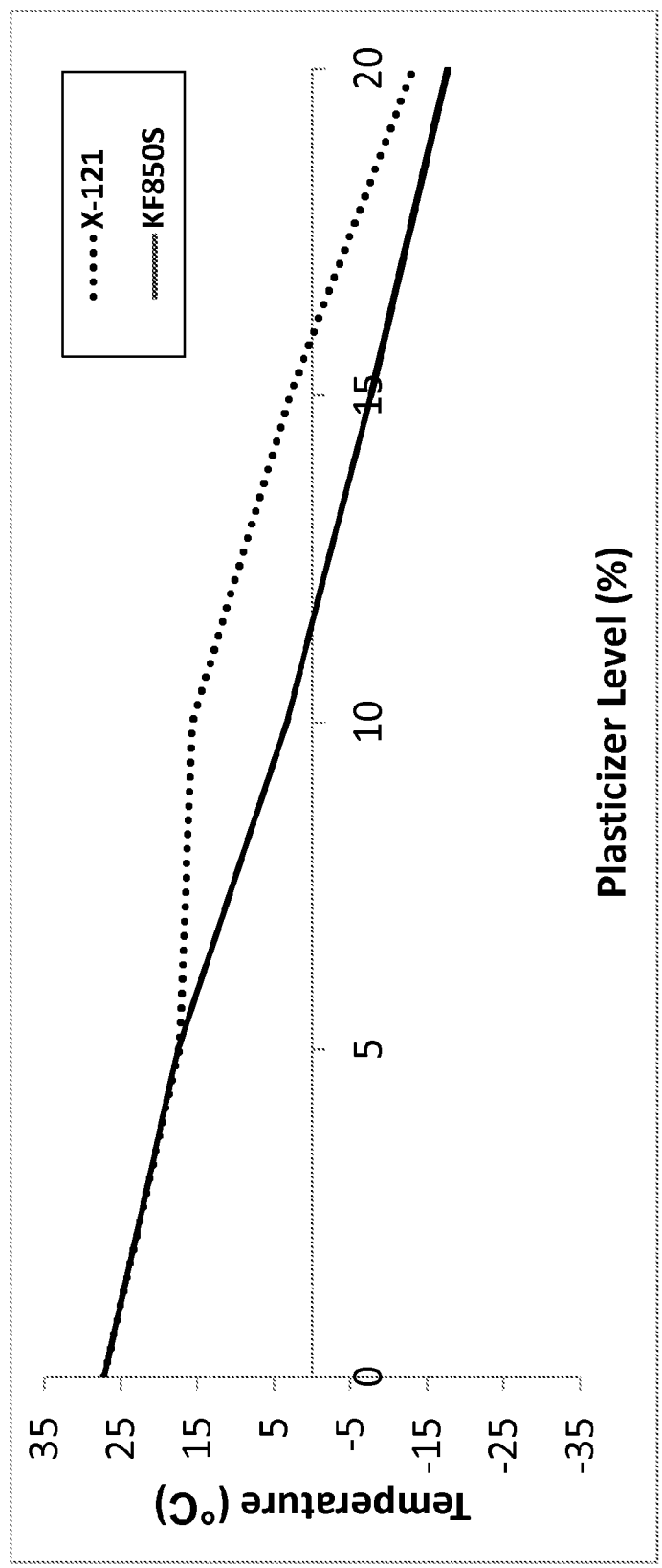
FIG. 27 - GLASS TRANSITION TEMPERATURE

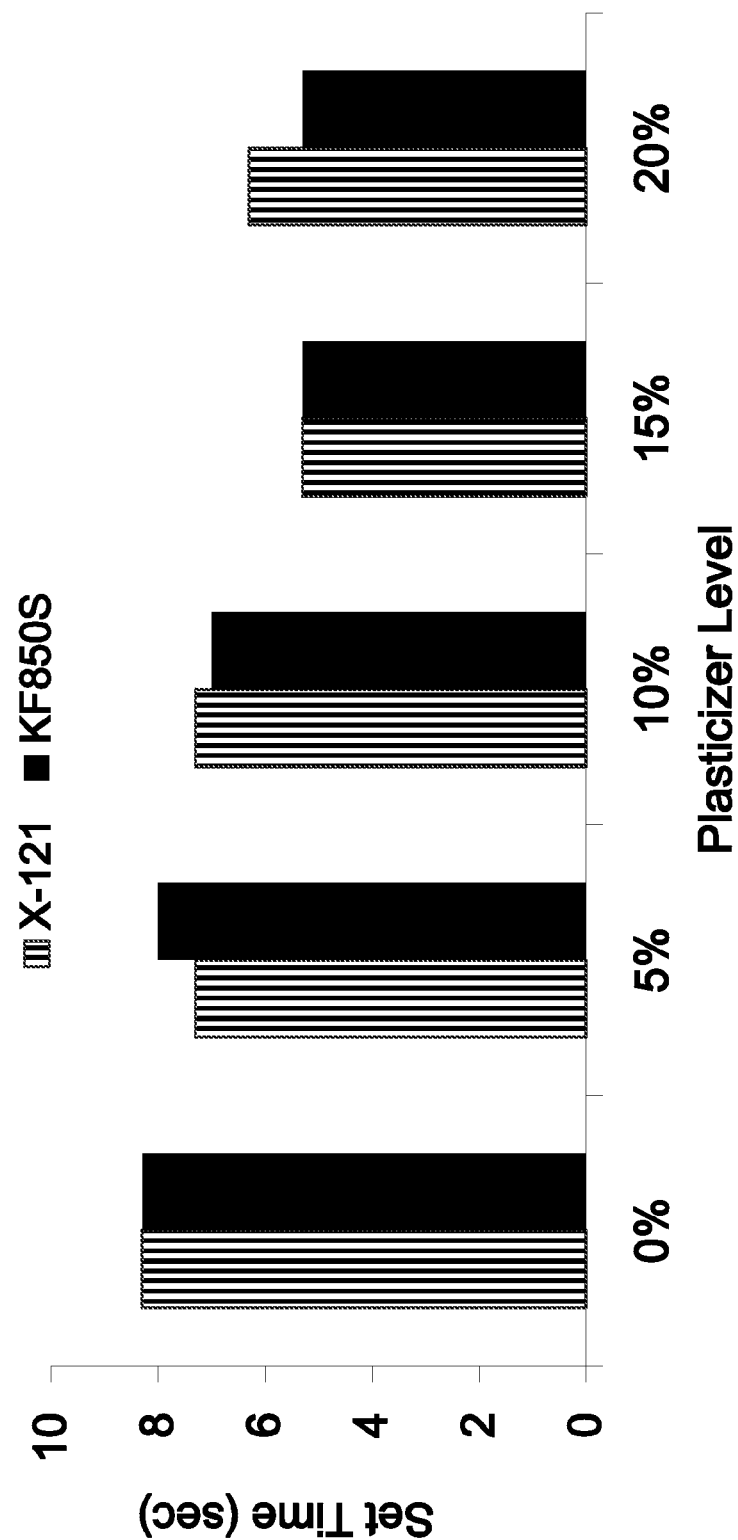

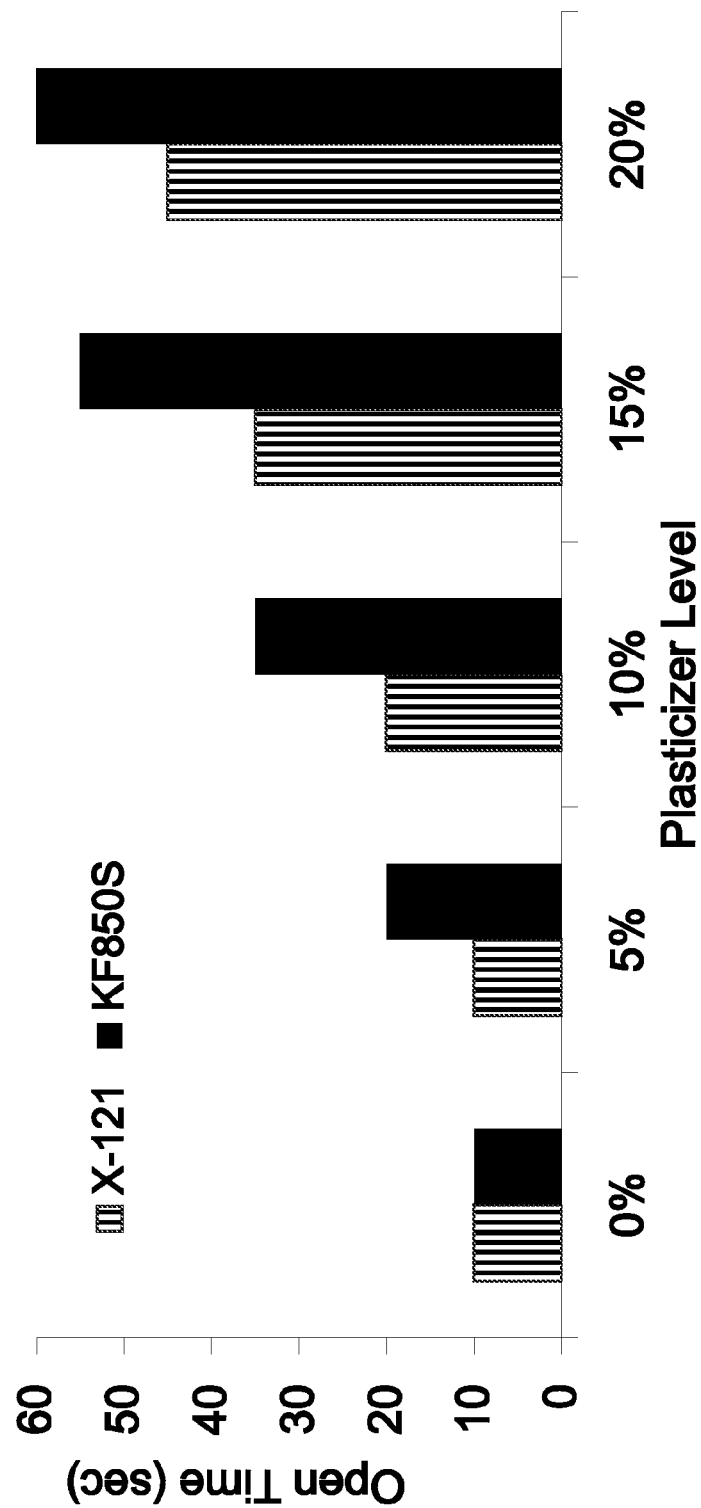

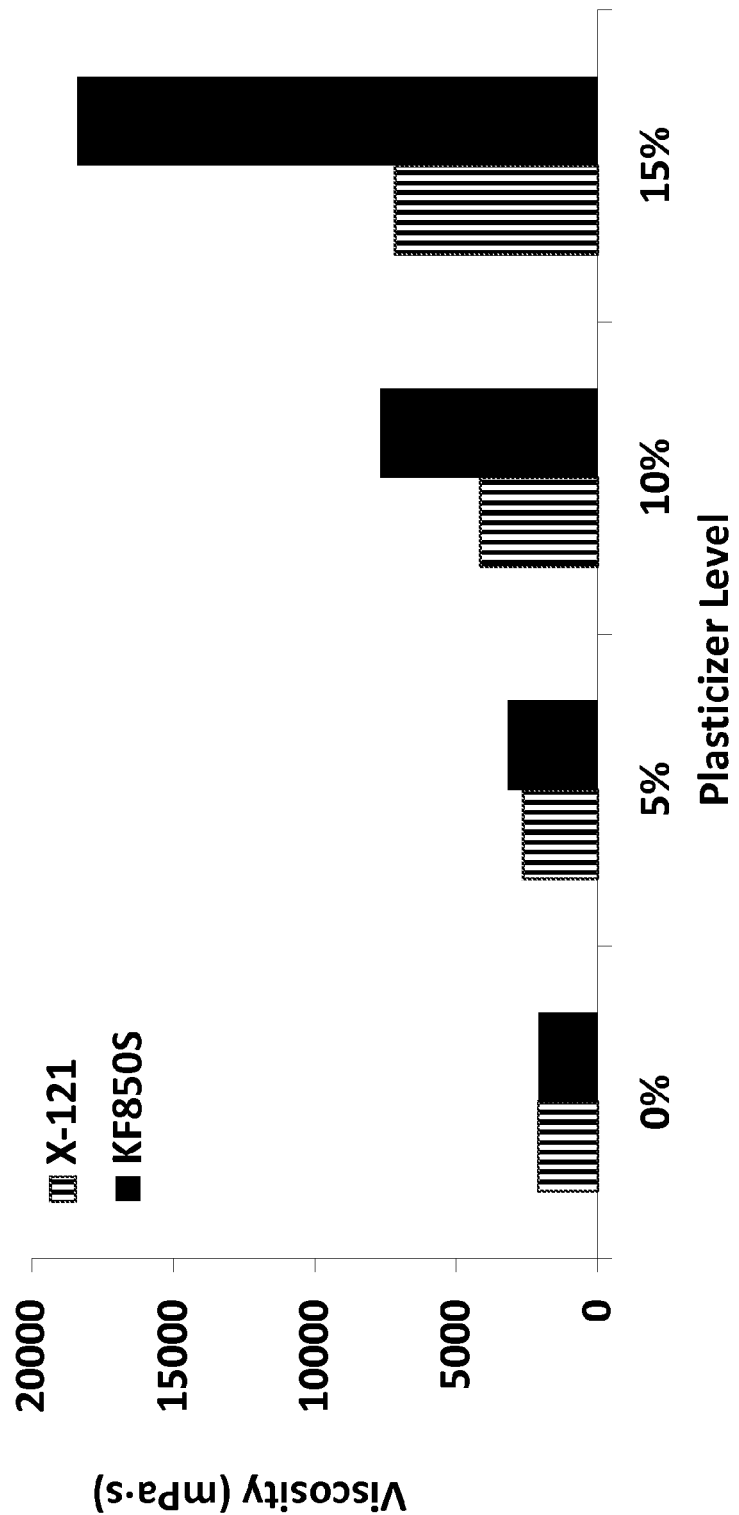

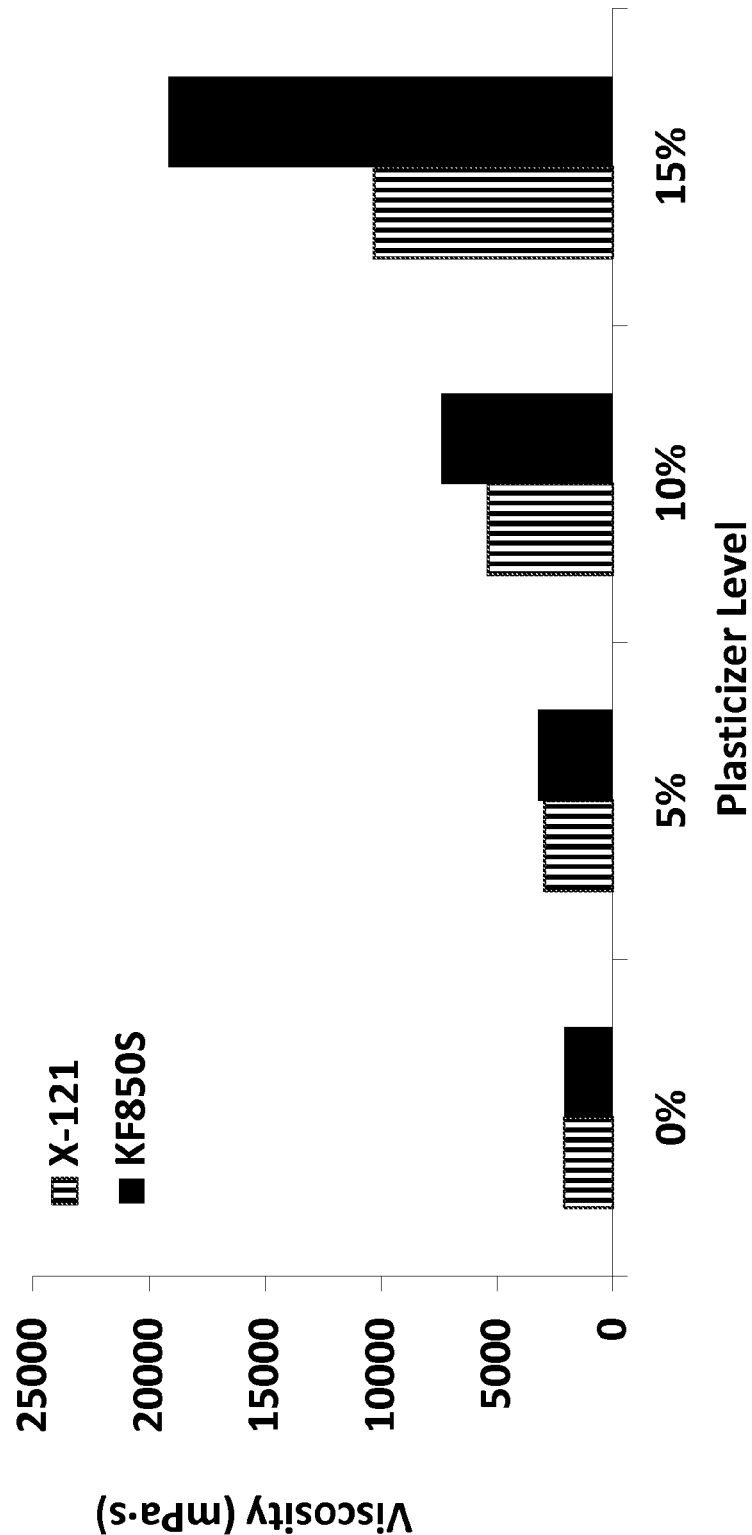

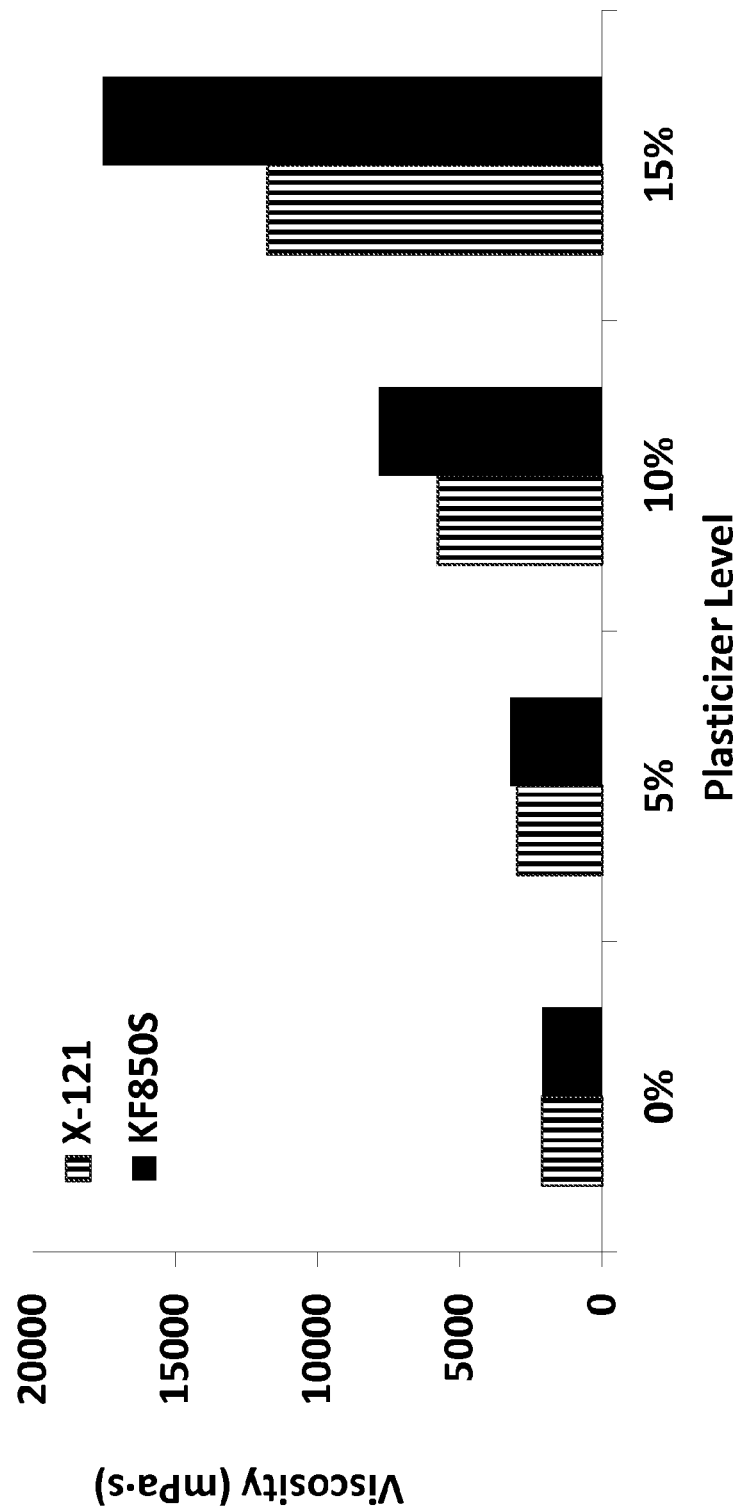

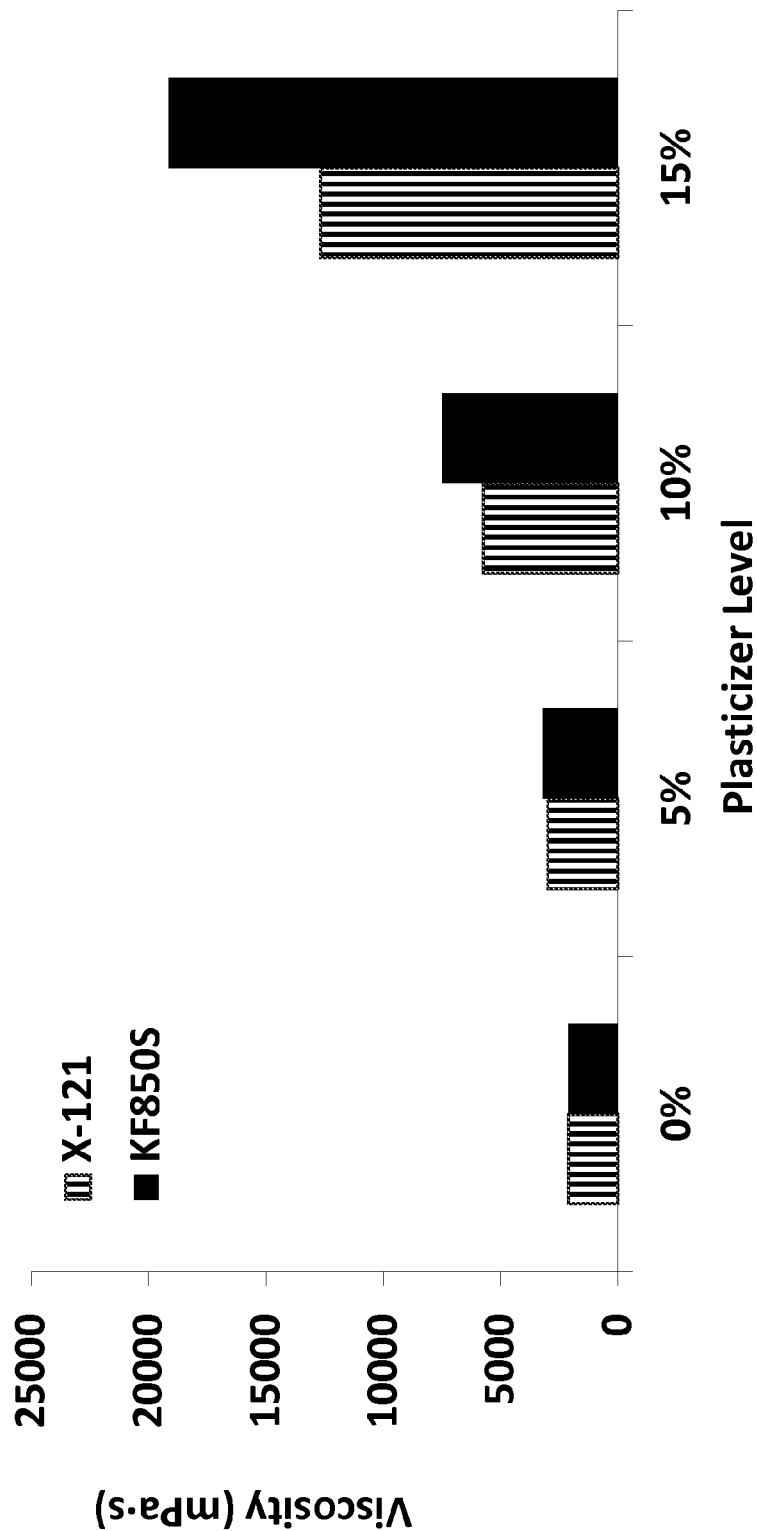

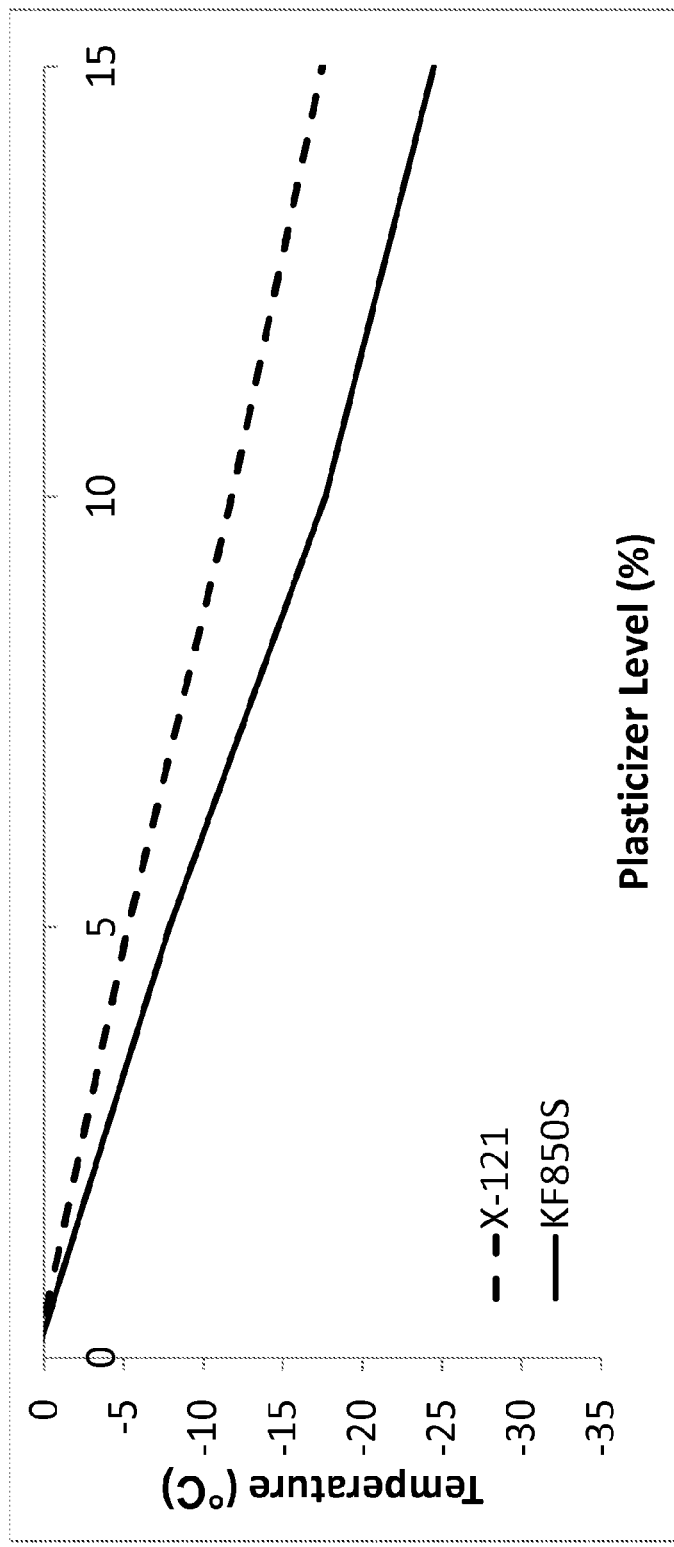
FIG. 34 - GLASS TRANSITION TEMPERATURE

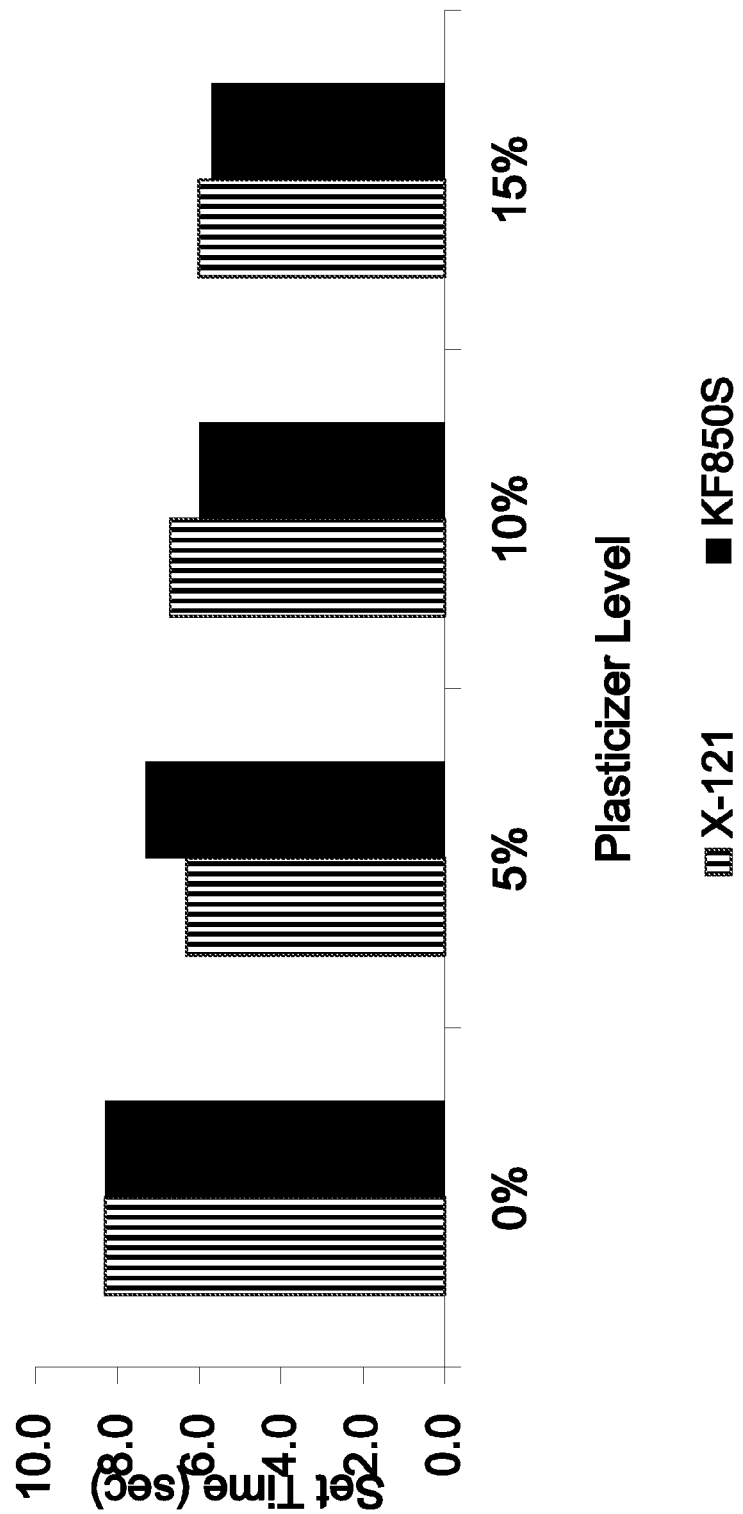

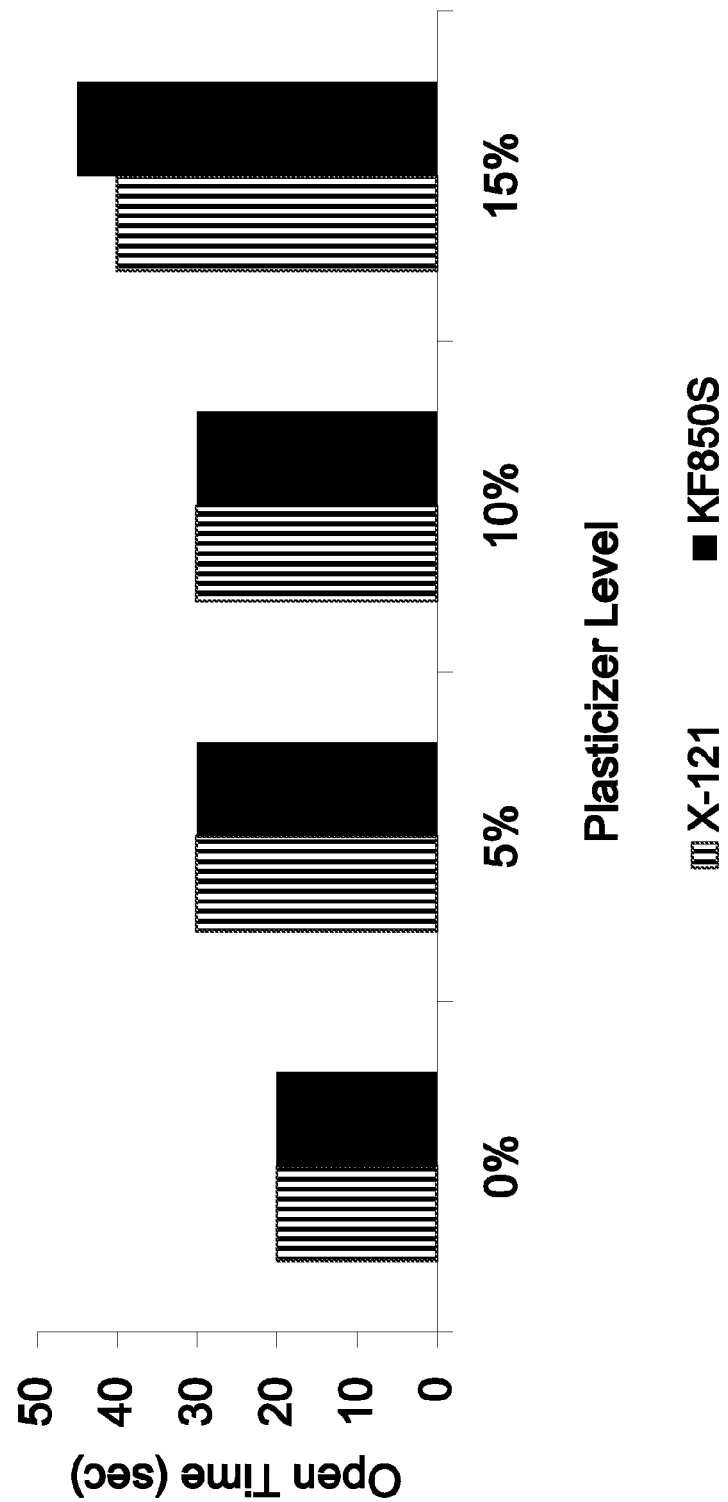

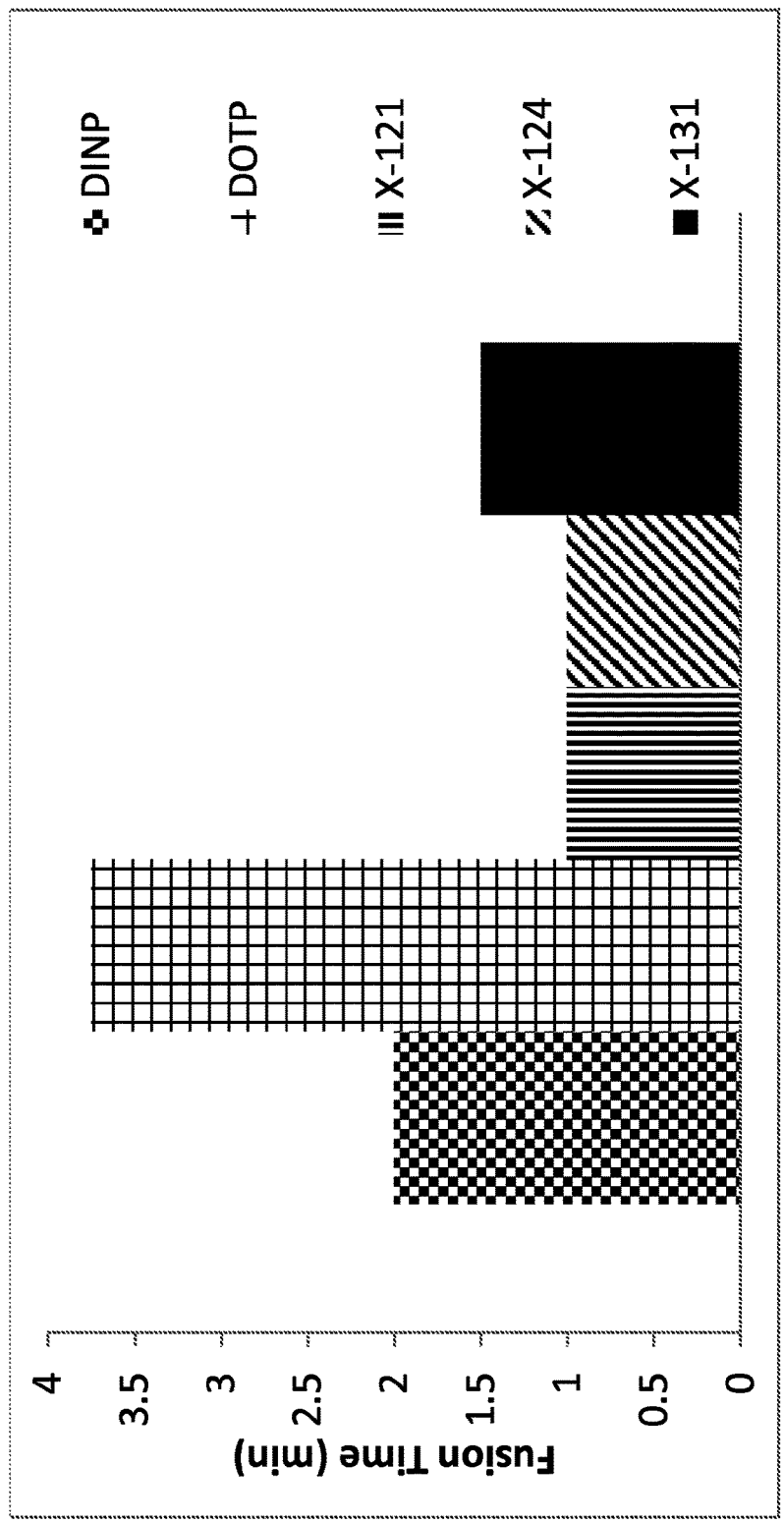
FIG. 37 - TIME TO FUSION

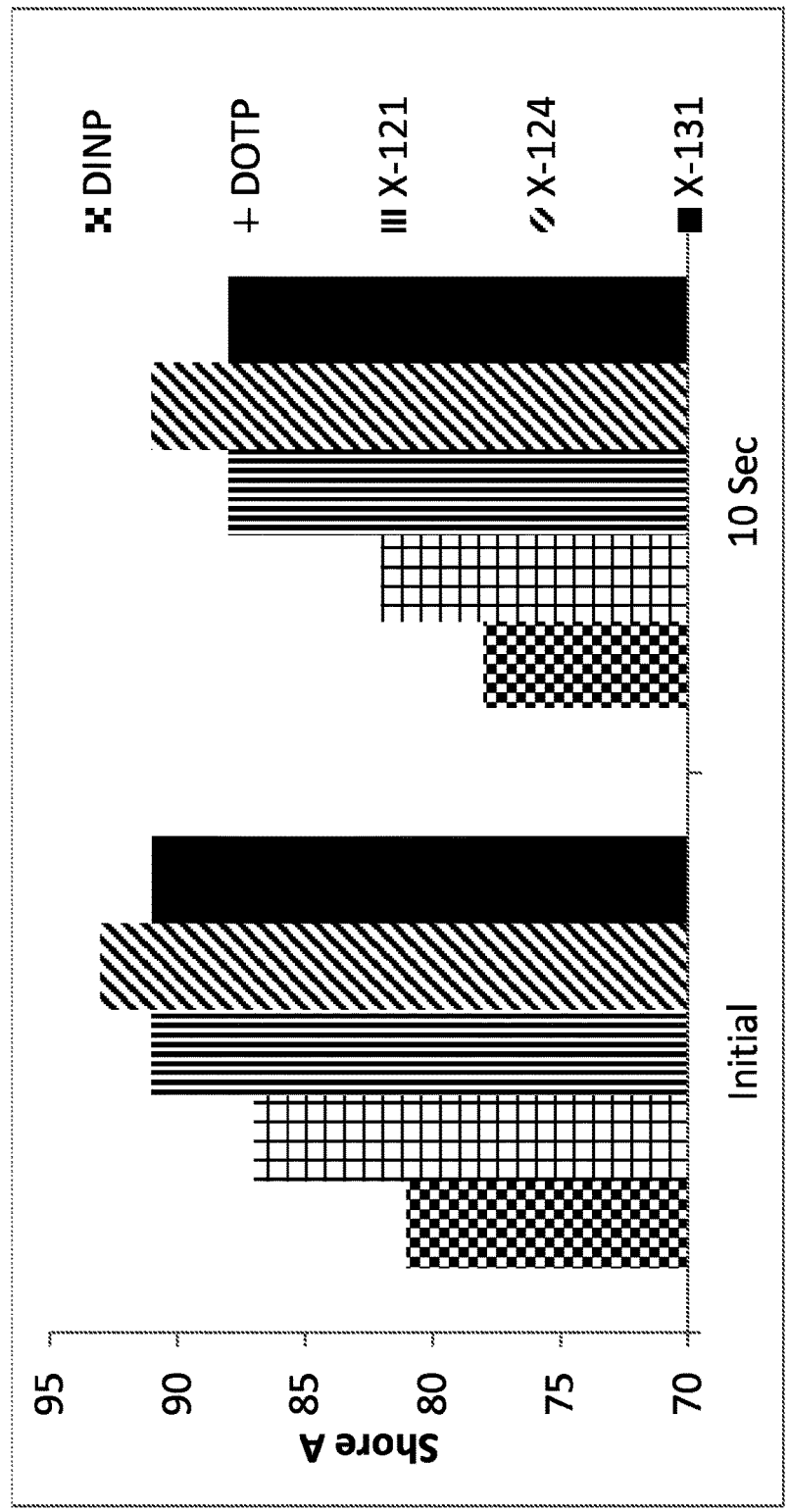

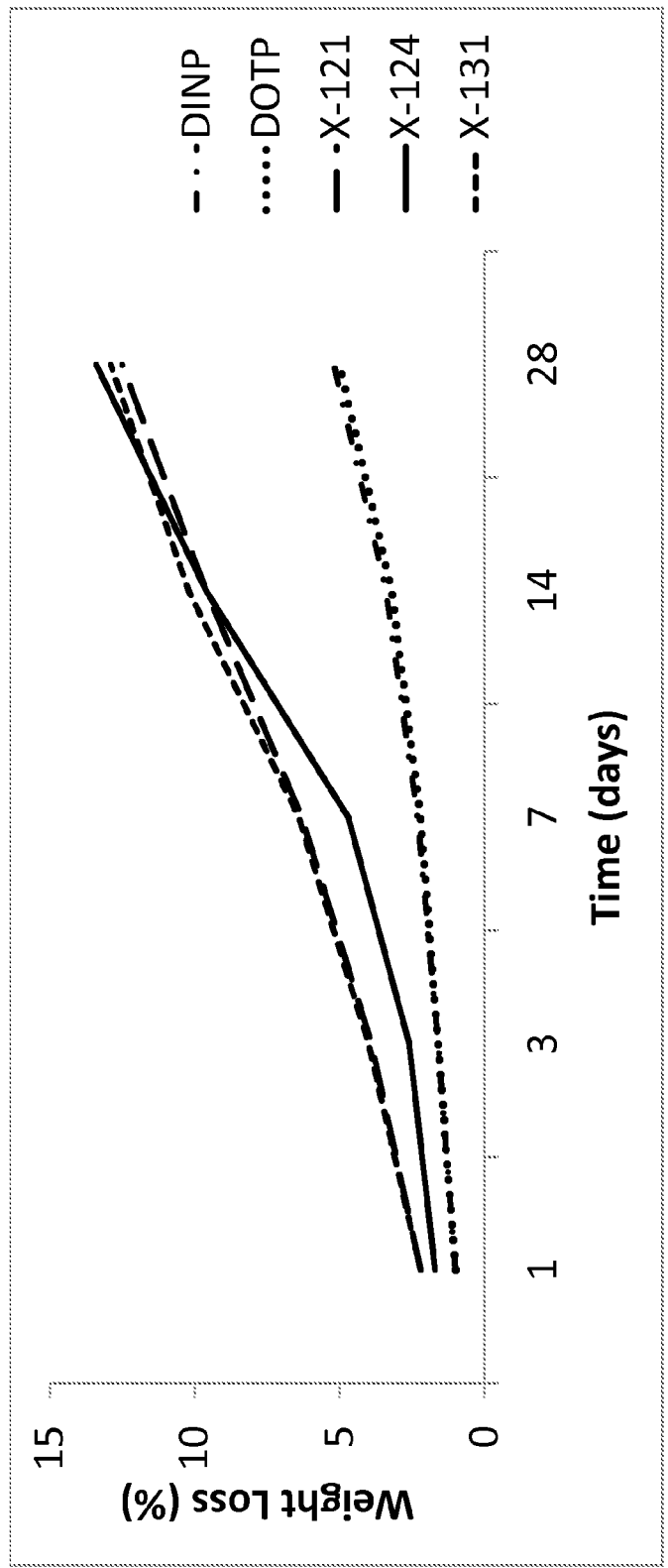
FIG. 39 - VOLATILE LOSS

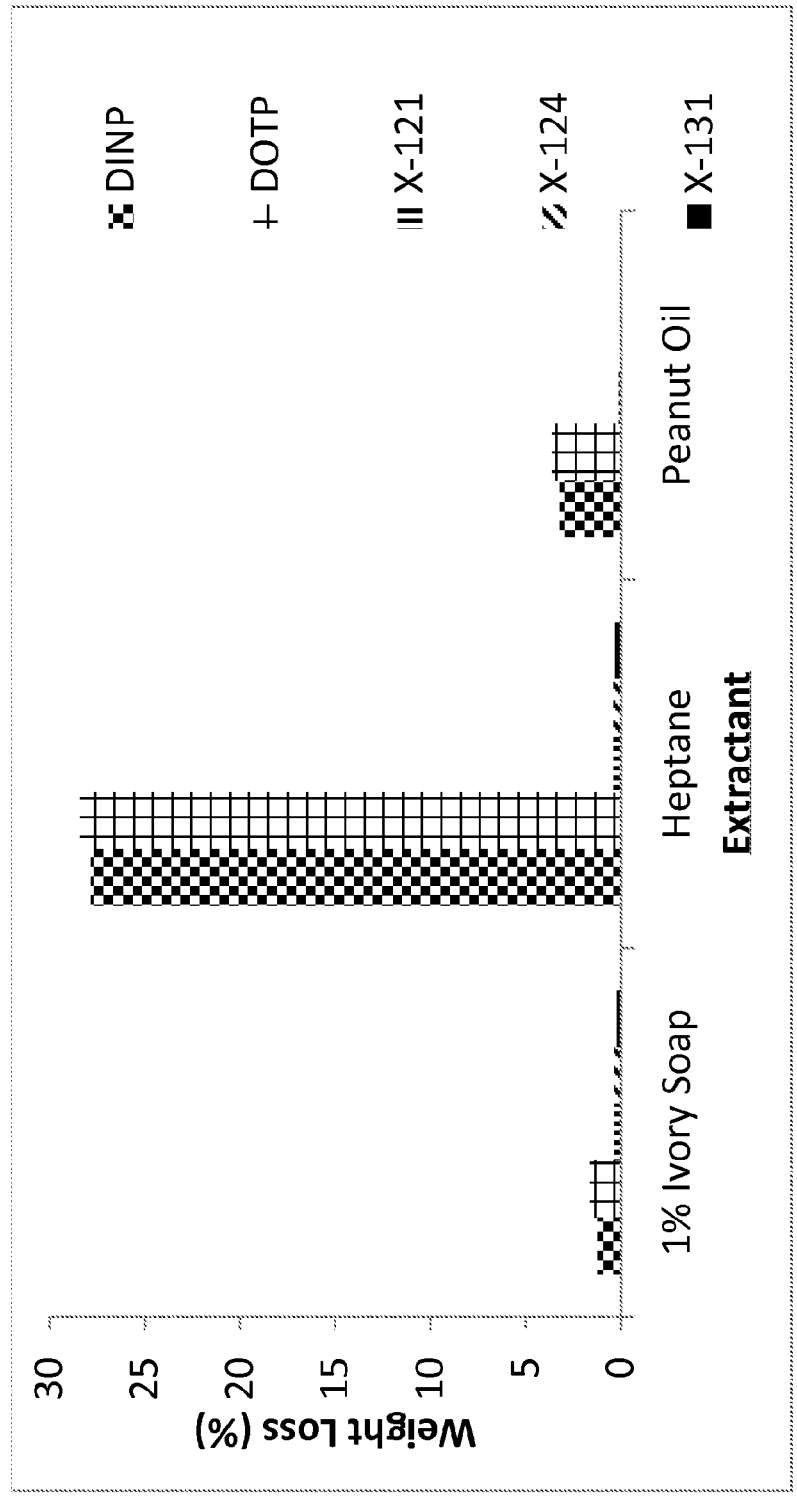
FIG. 40 - EXTRACTION RESISTANCE

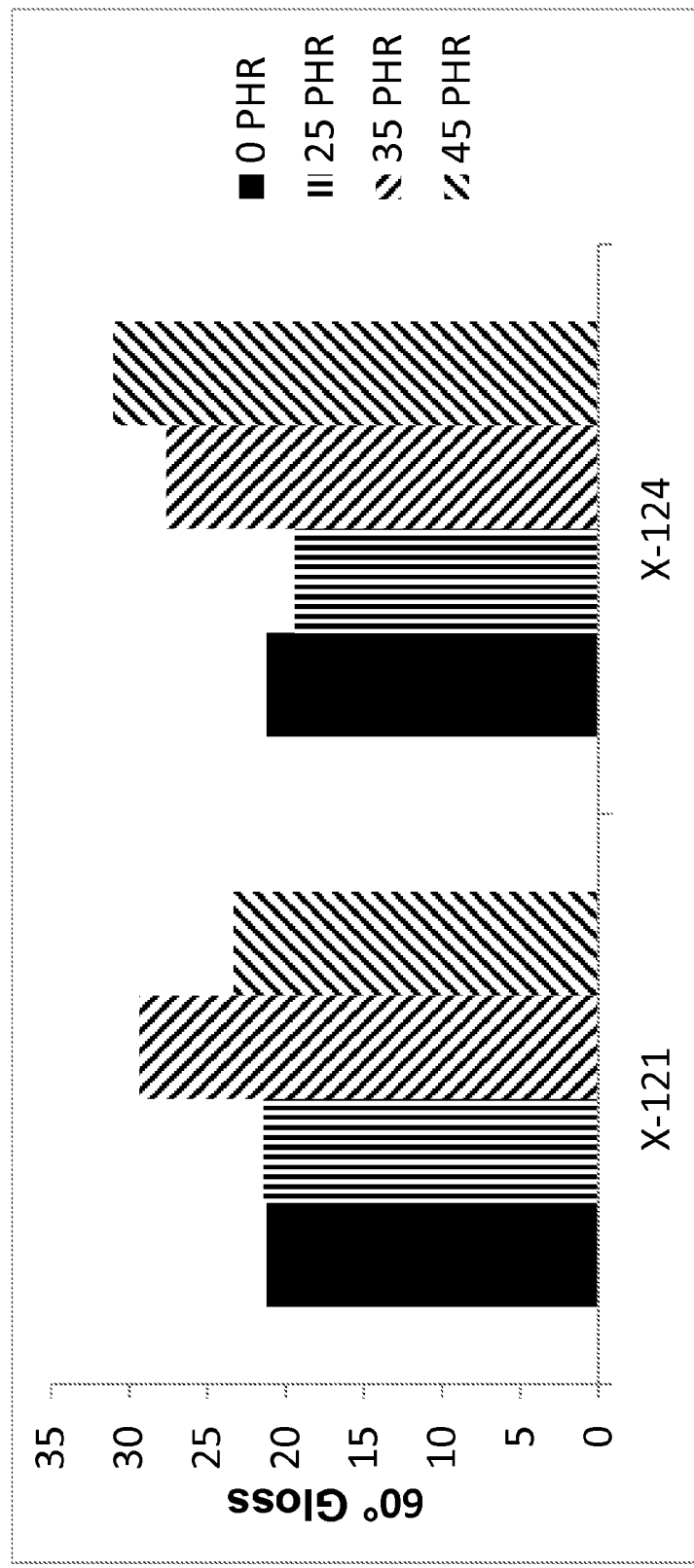

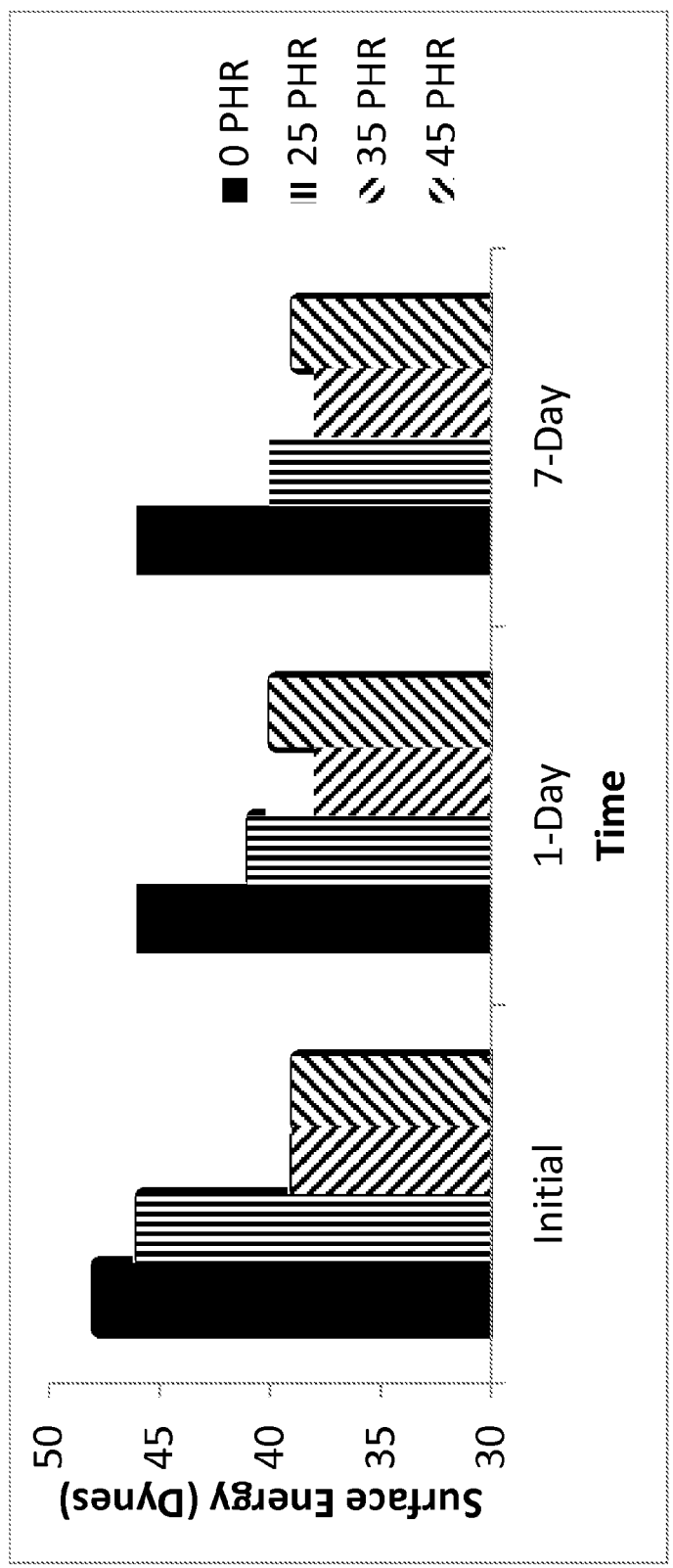

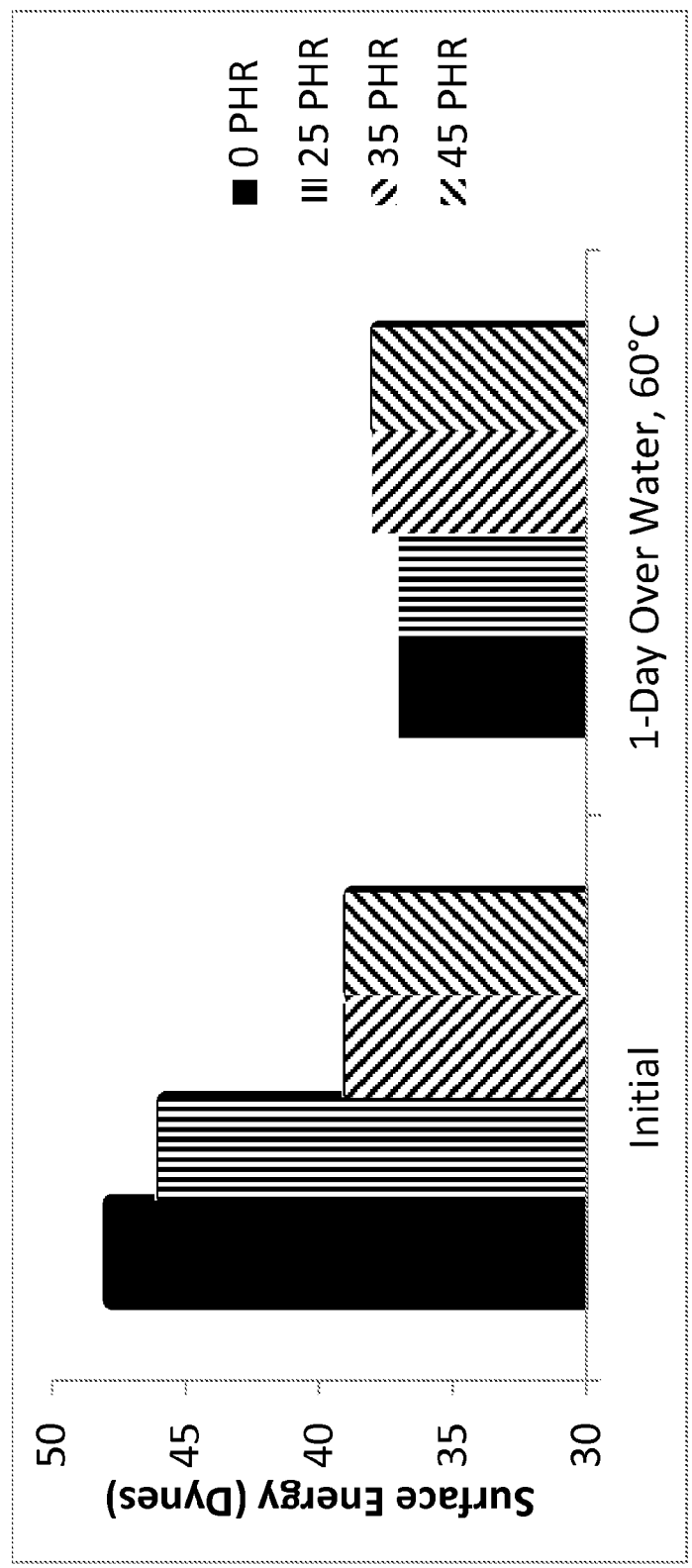

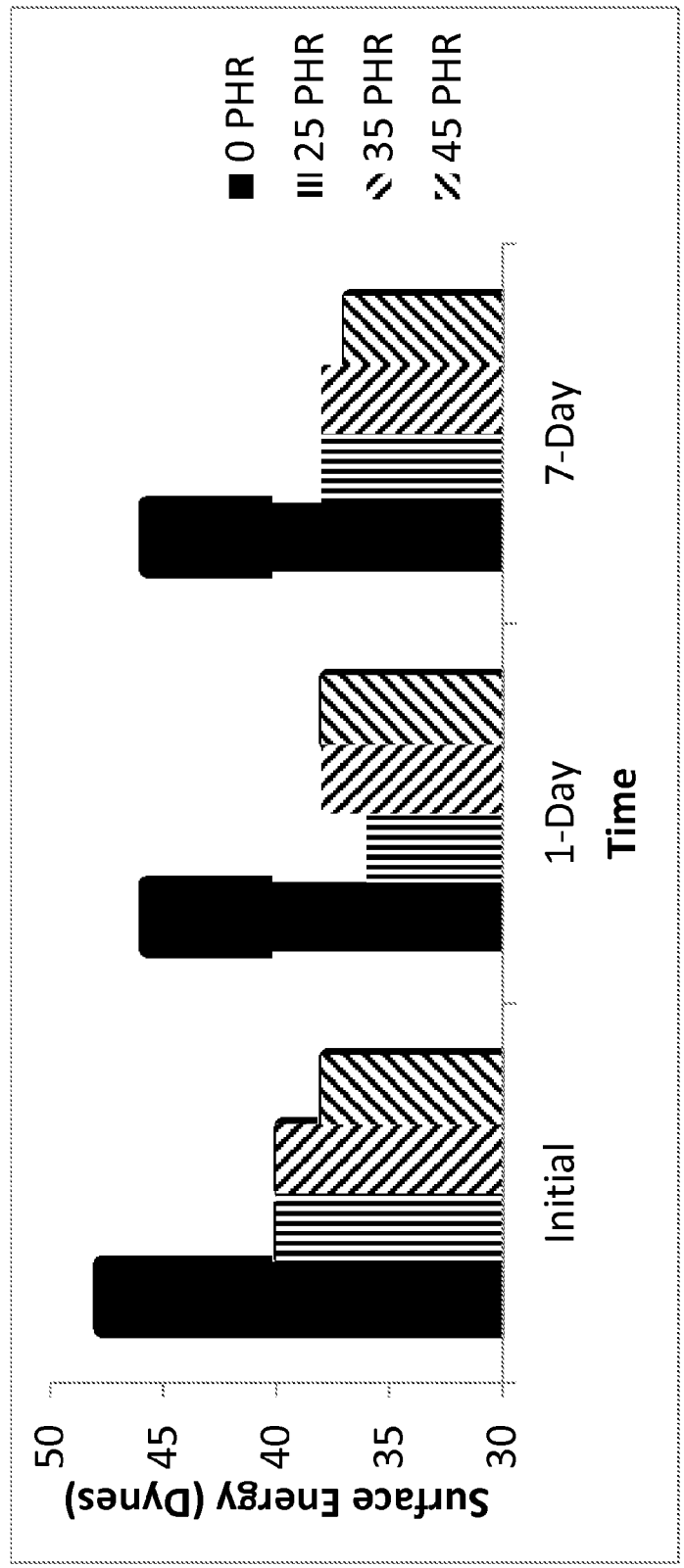
FIG. 44 - SURFACE ENERGY OVER TIME, 23°C/50% RH - X-124

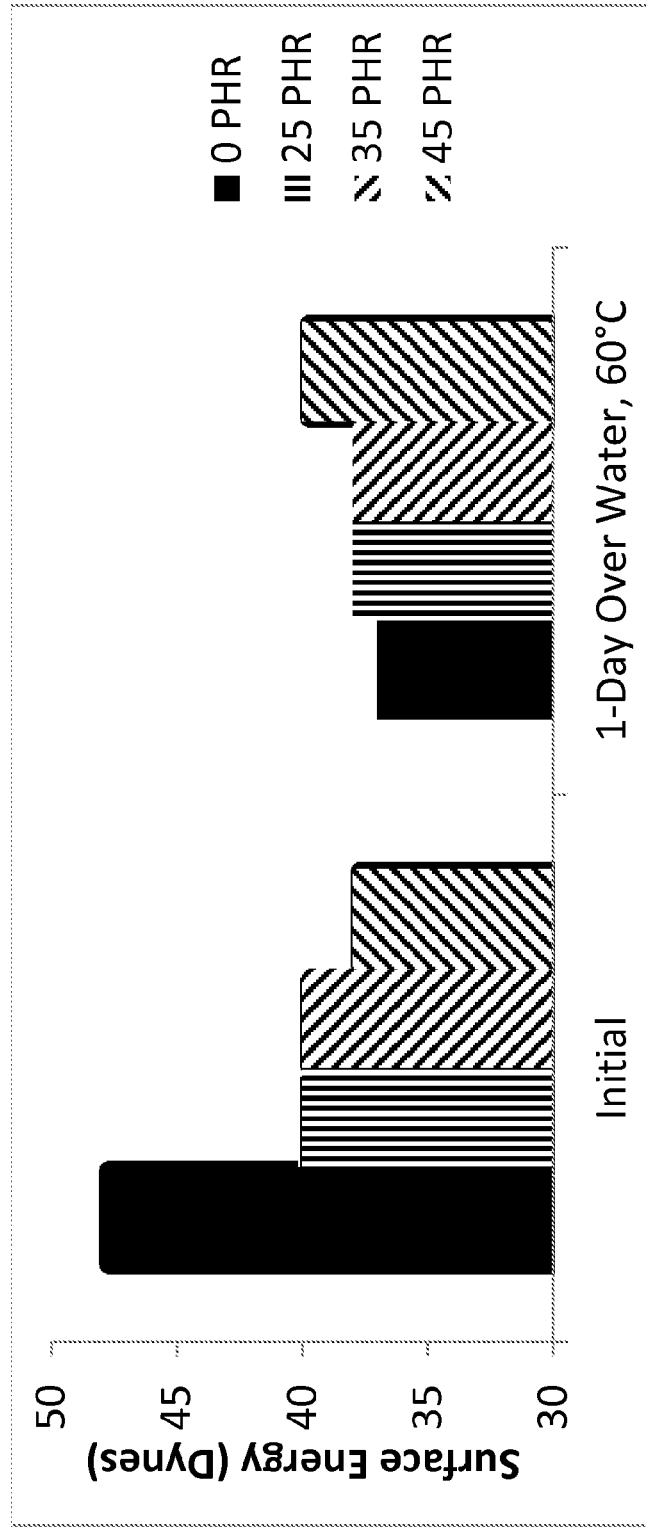

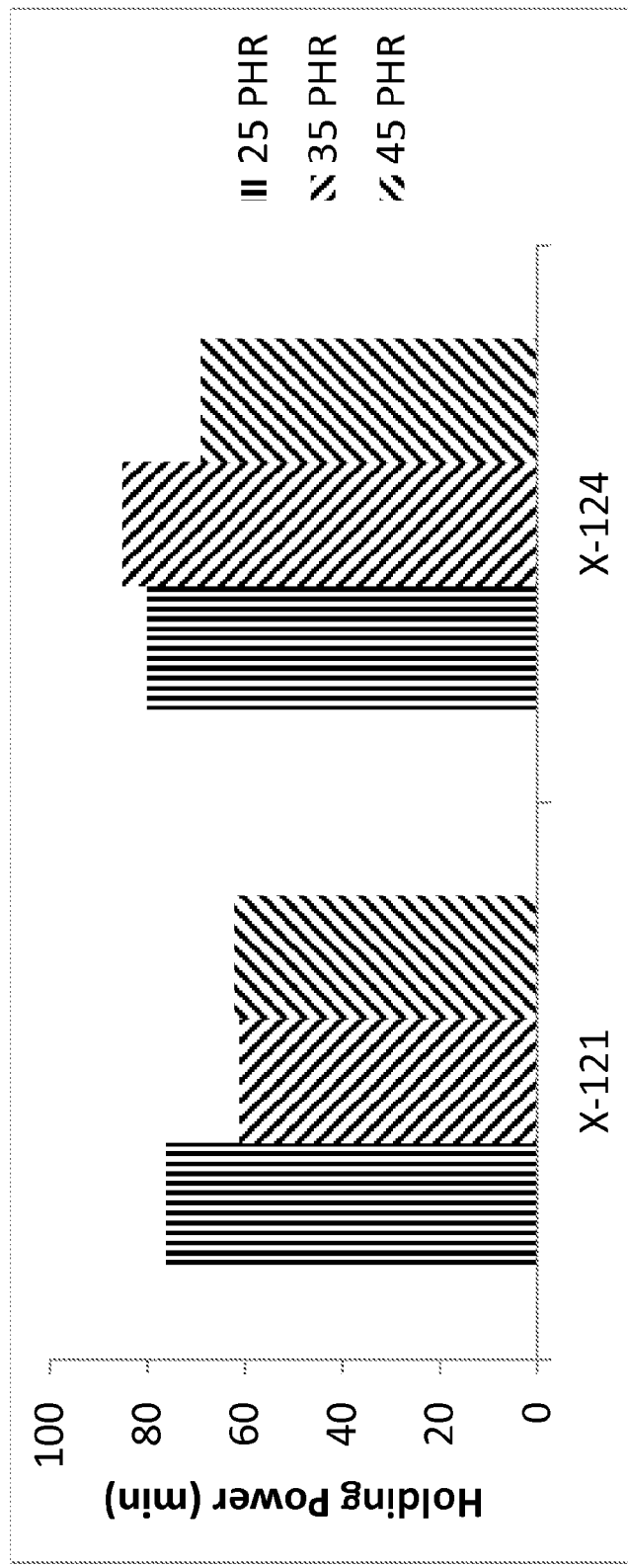
FIG. 46 - PLASTICIZER MIGRATION - 1-DAY, 23°C/RH
Plasticizer migration as determined by a change in adhesive holding power as plasticizer loading increases. None noted under 24 hour/RT conditioning.

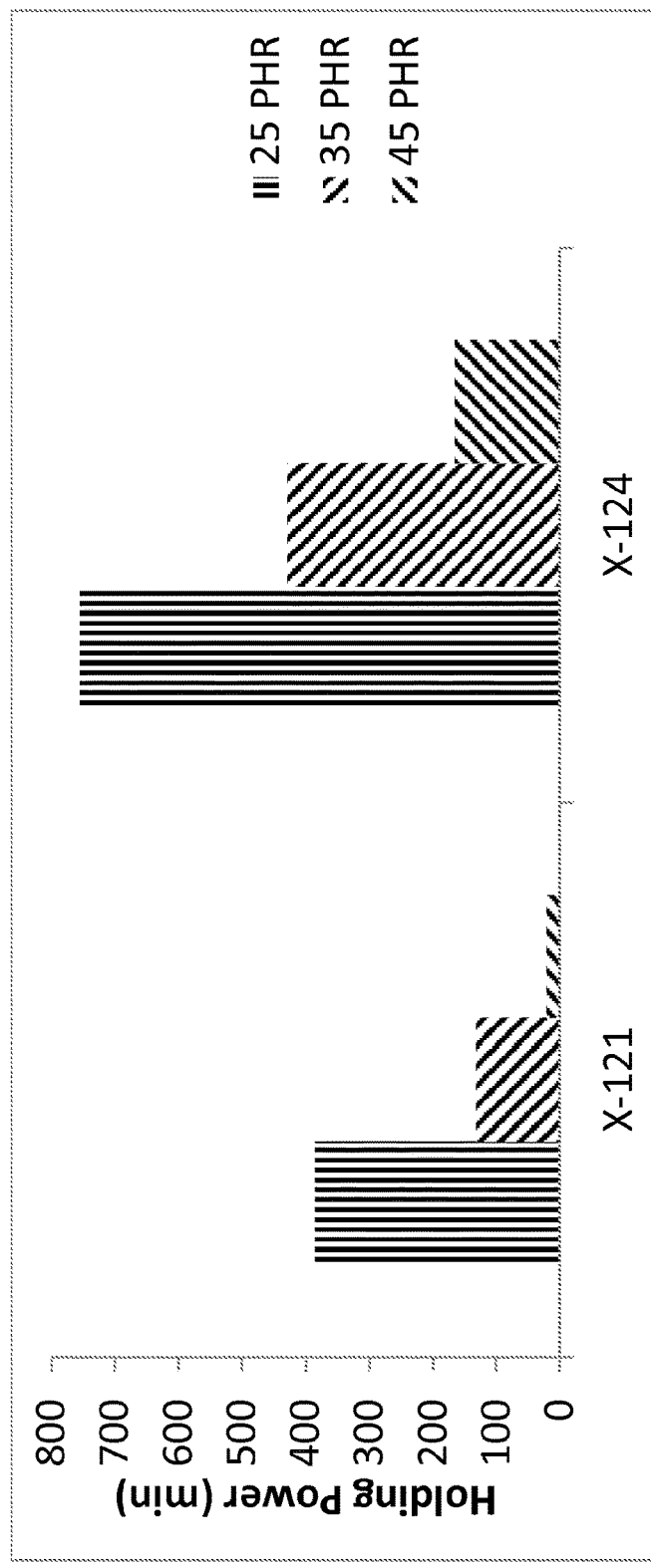

POLYESTER PLASTICIZERS WITH BENZOIC ACID END-CAPS

FIELD OF THE INVENTION

This invention is directed to novel plasticizer compositions for use in a variety of polymeric dispersions, including without limitation caulks, sealants, adhesives and vinyl. In particular, the invention is directed to polyester plasticizers comprising alternating units of glycols and dibasic acids end-capped with benzoate and/or acetate esters. The invention is also directed to compositions containing the novel plasticizer compositions.

BACKGROUND OF THE INVENTION

Polyester plasticizers are generally categorized as specialty-type plasticizers and comprise a wide variety of chemistries. Polymeric polyester plasticizers are produced from polyhydric alcohols (diols) esterified with dibasic acids, commonly adipic acid, in the presence of monobasic acids or alcohols. These polymeric polyesters comprise regularly alternating (repeating) units of dibasic acids and glycols (or diols), as compared to monomeric plasticizers that do not contain repeating units.

Polyester plasticizers are known in the art for use in a number of applications, such as adhesives, caulks, sealants, and polyvinyl chloride (PVC) plastisols. As do other plasticizers, polyester plasticizers provide compounded polymeric compositions with improved properties, such as low volatility, resistance to extraction, excellent flexibility, durability, and UV and heat resistance properties, among others, depending on the structure and molecular weight of the particular polyester utilized. Polymeric polyester plasticizers, in particular, offer low volatility, resistance to extraction by hydrocarbon fluids, and depending on the particular plasticizer—resistance to surface marring. As one example, polyester plasticizers used in polyvinyl chloride (PVC) have better extraction resistance properties than that achieved with most monomeric plasticizers, and they also demonstrate excellent non-migration properties in vinyl plastics.

Polyester plasticizers can be used in blends to improve the performance of standard monomeric plasticizers or as a substitute for them. They also may but are not required to be blended with various other conventional plasticizers to enhance or augment properties of polymeric compositions, including but not limited to improving solvating characteristics and compatibility and processability in plastisol applications. Suitable conventional plasticizers for use with polyester plasticizers include general purpose, specialty and/or secondary plasticizers, examples of which include without limitation phthalate esters, dibenzoate esters, phosphate esters, various adipate, azelate, oleate, succinate and sebacate compounds, terephthalate esters such as dioctyl terephthalate (DOTP), 1,2-cyclohexane dicarboxylate esters (such as Hexamoll® DINCH®), epoxy plasticizers, fatty acid esters, glycol derivatives, sulfonamides, and hydrocarbons and hydrocarbon derivatives that are often utilized as secondary plasticizers. Monobenzoates, such as isononyl benzoate, isodecyl benzoate, and 2-ethylhexyl benzoate, and 2,2,4-trimethyl-1,3-pentanediol diisobutyrate, among other plasticizers, can also be blended with polyester plasticizers.

It has been discovered that certain polyester plasticizers, in particular lower molecular weight oligomeric dibenzoates, are viable alternatives for traditional phthalate plasticizers used in adhesives, caulks, and sealants. They are also useful substitutes alone or in combination with other plasticizers in plastisol applications, including without limitation in PVC. These oligomeric dibenzoates comprise certain polyester plasticizers that are end-capped with benzoic acid esters.

In preparation, the oligomeric dibenzoates of the invention may have a portion of molecules which are not fully reacted, i.e., do not convert to dual benzoic acid end caps. As a result, shorter chain, hydroxyl (—OH) terminated molecules are formed, which are more water soluble than molecules having dual benzoic acid ester end-caps. These hydroxyl terminated compositions can, in some circumstances, be reactive. Depending on application, their use may be limited due to incompatibility with a polymer. Decreasing the concentration of residual hydroxyl-terminated molecules will improve compatibility by decreasing the percentage of molecules that are extractable by water.

By adding acetic anhydride during the preparation process of the oligomeric dibenzoates of the invention, unreacted hydroxyl groups may be eliminated or significantly reduced. Any excess acetic anhydride is removed at the end of the process. Use of acetic anhydride may also result in the formation of a polyester having hybrid benzoate/acetate ester end-caps. It has been discovered that this hybrid benzoate/acetate end-capped polyester is also a viable alternative for more traditional plasticizers in certain applications, often with improved results, even over the non-acetic anhydride-modified oligomeric polyester plasticizers of the invention.

The oligomeric polyester plasticizers of the invention are preferably based upon propylene glycol adipate and propylene glycol succinate polyesters that are dual end-capped (terminated on both ends) with esters of benzoic acid, i.e., propylene glycol/adipate/benzoate and propylene glycol/succinate/benzoate. The benzoate end-caps change the polarity of the polyesters making them very versatile plasticizers for use with a large number of polymers. Alternatively, the oligomeric polyester plasticizers of the invention preferably include those having hybrid benzoate/acetate end-caps.

The polyester plasticizers of the invention may also comprise other glycols (diols) and dibasic acids. Diol glycols useful in the inventive compositions, including without limitation 1,3-butane diol, 1,4-butane diol, 1,3-propane diol, and mixtures thereof. Useful dibasic acids include without limitation azelaic, glutaric, sebacic, phthalic and terephthalic acid. Polyesters prepared from these other diols and dibasic acids are also within the contemplation of the invention.

Applications for use of the inventive polyester plasticizers may depend on molecular weight. For example, the higher molecular weight propylene glycol adipate end-capped with benzoic acid esters functions well as a substitute for industry standard phthalates in polysulfide or other sealant and caulk applications, as well as in vinyl applications. The lower molecular weight propylene glycol succinate end-capped with benzoic acid esters also performs well in vinyl applications. None of these oligomeric dibenzoates are known to have been used in these applications heretofore. Surprisingly, these oligomeric dibenzoates function as well or better than traditional higher molecular weight phthalate plasticizers.

It has also been found that the inventive polyesters having hybrid benzoate and acetate ester end caps are less prone to water extraction and reactivity in certain use applications. This will result in better and longer term performance in PVC applications where exposure to weathering is expected. Since it does not extract easily, it will perform better as a plasticizer as it will continue to soften the polymer.

The inventive polyester plasticizers may be derived from natural sources, making them highly desirable from an environmental perspective.

It is an object of the invention to provide novel plasticizers comprising polyesters end-capped with dual benzoate esters or hybrid benzoate/acetate esters, which are useful in a wide variety of applications where plasticizers are traditionally used.

It is a further object of the invention to provide novel polyester plasticizers that may be used as alternatives to traditional phthalate or other traditional plasticizers in adhesives, caulks, sealants, plastisols, vinyl compositions, and other polymeric dispersions.

Yet another object of the invention is to provide adhesive, caulk, sealant, vinyl and other polymeric compositions utilizing the novel polyester plasticizers of the invention.

Still another object of the invention is to provide novel polyester plasticizers that may be blended with traditional plasticizers to improve properties of both the plasticizer and the polymeric compositions in which the blends are used.

Still a further object of the invention is to provide novel polyester plasticizers that achieve comparable or improved compatibility, processability, extraction resistance, hardness, strength, surface energy retention, volatility, and migration characteristics over traditional plasticizers used in polymeric compositions.

Other objects of the invention will be evident to one skilled in the art.

SUMMARY OF THE INVENTION

The invention is directed to the use of oligomeric dibenzoate or oligomeric benzoate/acetate polyesters as plasticizers in adhesives, caulks, sealants, and vinyl, among other polymeric compositions. The invention is also directed to adhesives, caulks, sealants, coatings, and vinyl compositions, among others, comprising the inventive oligomeric polyesters as a plasticizer component. The oligomeric polyester plasticizers of the invention are useful as alternative plasticizers alone or in blends with other plasticizers in applications where plasticizers are traditionally used.

The inventive polyester plasticizers of the invention have either dual end-caps of benzoate esters or hybrid benzoate/acetate ester end-caps. A particularly preferred embodiment is a polyester comprising regularly alternating units of a glycol (diol) and a dibasic acid, wherein the polyester is dual end-capped with benzoic acid.

In another embodiment, the inventive plasticizer is a polyester comprising regularly alternating units of a glycol (diol) and a dibasic acid, wherein the polyester is end-capped with hybrid benzoate and acetate esters.

In a particular embodiment, the invention is a plasticizer composition comprising a propylene glycol polyester (adipate or succinate) dual end-capped with benzoate esters, having little or no free hydroxyl groups.

In another particular embodiment, the invention is a plasticizer composition comprising a propylene glycol polyester (adipate or succinate) having hybrid benzoate and acetate end-caps.

In still another embodiment, the invention is an adhesive, caulk, sealant, plastisol or vinyl composition comprising the inventive polyester plasticizer end-capped compositions.

The invention is also directed to a method of preparing the inventive polyester end-capped compositions utilizing a zinc acetate catalyst and altered process conditions, which is an improvement over prior art methods of polyester preparation.

The inventive method for preparing the inventive polyester end-capped compositions includes acetic anhydride addition in situ to reduce or eliminate undesirable hydroxyl groups, during the preparation process for the oligomeric dibenzoate polyesters of the invention.

In still another embodiment, the invention is directed to plasticizer blends comprising the inventive polyester plasticizers.

In another embodiment, the invention is directed to polyester plasticizers achieving comparable or better compatibility, processability, extraction resistance, tensile strength, volatility, migration, surface energy, and surface energy retention, among other properties, when compared with results achieved with traditional plasticizers used in polymeric compositions.

DESCRIPTION OF THE DRAWINGS

FIG. 1 shows the steady shear viscosity for two inventive polyester plasticizers as compared to a phthalate control on the B-side of a polysulfide sealant;

FIG. 2 shows the Shore A hardness results over time obtained for polysulfide sealants comprising two inventive polyester plasticizers as compared to a phthalate control;

FIG. 3 shows one day results for tensile strength (psi), 100% modulus (psi) and elongation results (%) obtained for polysulfide sealant samples comprising a phthalate control, a phthalate/polyester blend, and two samples of a dibenzoate triblend each in combination with an inventive polyester;

FIG. 4 shows four week results for tensile strength (psi), 100% modulus (psi) and elongation results (%) obtained for polysulfide sealant samples comprising a phthalate control, a phthalate/polyester blend, and two samples of a dibenzoate triblend each in combination with an inventive polyester;

FIG. 5 shows polysulfide sealant pot-life (time to 250 Pa·s at 100 s$^{-1}$) results for two inventive polyester plasticizers and a traditional phthalate plasticizer in combination with a various A-side components: INBP, a dibenzoate diblend, and a dibenzoate triblend;

FIG. 6 shows lap shear results obtained for polysulfide sealant samples comprising an isononyl benzyl phthalate (INBP)/trimethyl-1-3-pentanediol monoisobutyrate benzyl phthalate (TBP) control, and INBP/inventive polyester, and two samples of a dibenzoate triblend in combination with a polyester plasticizer of the invention;

FIG. 7 shows loop test results for an underbody "filled" sealant polyvinyl chloride (PVC) plastisol obtained over 4 weeks, comparing a phthalate control and a polyester plasticizer of the invention;

FIG. 8 shows initial shear results obtained for the underbody filled sealant PVC plastisol, comparing a phthalate control and a polyester plasticizer of the invention;

FIG. 9 shows one day shear results obtained for the underbody filled sealant PVC plastisol, comparing a phthalate control and a polyester plasticizer of the invention;

FIG. 10 shows three day shear results obtained for the underbody filled sealant PVC plastisol, comparing a phthalate control and a polyester plasticizer of the invention;

FIG. 11 shows gel fusion results obtained for the underbody filled sealant PVC plastisol, comparing a phthalate control and a polyester plasticizer of the invention;

FIG. 12 shows Brookfield viscosity results initially and at one day and three days for an unfilled PVC plastisol, comparing a traditional phthalate plasticizer and an inventive polyester plasticizer;

FIG. 13 shows initial shear results for an unfilled PVC plastisol, comparing a traditional phthalate control and an inventive polyester plasticizer;

FIG. 14 shows one day shear results for an unfilled PVC plastisol, comparing a traditional phthalate control and an inventive polyester plasticizer;

FIG. 15 shows three day shear results for an unfilled PVC plastisol, comparing a traditional phthalate control and an inventive polyester plasticizer;

FIG. 16 shows gel fusion curves for an unfilled PVC plastisol, comparing a traditional phthalate control and an inventive polyester plasticizer;

FIG. 17 shows roll test results for an unfilled PVC plastisol, comparing a traditional phthalate control and an inventive polyester plasticizer;

FIG. 18 shows loop test results for an unfilled PVC plastisol, comparing a traditional phthalate control and an inventive polyester plasticizer;

FIG. 19 shows viscosity results obtained initially and at one day, three days, and seven days for a filled PVC plastisol, comparing a traditional phthalate control and an inventive polyester plasticizer;

FIG. 20 shows initial shear results obtained for a filled PVC plastisol, comparing a traditional phthalate control and an inventive polyester plasticizer;

FIG. 21 shows one day shear results obtained for a filled PVC plastisol, comparing a traditional phthalate control and an inventive polyester plasticizer;

FIG. 22 shows gel fusion results obtained for a filled PVC plastisol, comparing a traditional phthalate control and an inventive polyester plasticizer;

FIG. 23 shows initial viscosity results obtained for a waterborne polyvinyl acetate (PVAc) homopolymer adhesive comparing an inventive polyester plasticizer and a traditional dibenzoate diblend at 0%, 5%, 10%, 15%, and 20% plasticizer levels;

FIG. 24 shows one day viscosity results obtained for a waterborne PVAc homopolymer adhesive comparing an inventive polyester plasticizer and a traditional dibenzoate diblend at 0%, 5%, 10%, 15%, and 20% plasticizer levels;

FIG. 25 shows three day viscosity results obtained for a waterborne PVAc homopolymer adhesive comparing an inventive polyester plasticizer and a traditional dibenzoate diblend at 0%, 5%, 10%, 15%, and 20% plasticizer levels;

FIG. 26 shows seven day viscosity results obtained for a waterborne PVAc homopolymer adhesive comparing an inventive polyester plasticizer and a traditional dibenzoate diblend at 0%, 5%, 10%, 15%, and 20% plasticizer levels;

FIG. 27 shows glass transition temperature (Tg) curves obtained for a waterborne PVAc homopolymer adhesive comparing an inventive polyester plasticizer and a traditional dibenzoate diblend at 0%, 5%, 10%, 15%, and 20% plasticizer levels;

FIG. 28 shows set time results obtained for a waterborne PVAc homopolymer adhesive comparing an inventive polyester plasticizer and a traditional dibenzoate diblend at 0%, 5%, 10%, 15%, and 20% plasticizer levels;

FIG. 29 shows open time results obtained for a waterborne PVAc homopolymer adhesive comparing an inventive polyester plasticizer and a traditional dibenzoate diblend at 0%, 5%, 10%, 15%, and 20% plasticizer levels;

FIG. 30 shows initial viscosity results obtained for a waterborne ethylene vinyl acetate (EVA) adhesive comparing an inventive polyester plasticizer and a traditional dibenzoate diblend at 0%, 5%, 10%, and 15% plasticizer levels;

FIG. 31 shows one day viscosity results obtained for a waterborne EVA adhesive comparing an inventive polyester plasticizer and a traditional dibenzoate diblend at 0%, 5%, 10%, and 15% plasticizer levels;

FIG. 32 shows three day viscosity results obtained for a waterborne EVA adhesive comparing an inventive polyester plasticizer and a traditional dibenzoate diblend at 0%, 5%, 10%, and 15% plasticizer levels;

FIG. 33 shows seven day viscosity results obtained for a waterborne EVA adhesive comparing an inventive polyester plasticizer and a traditional dibenzoate diblend at 0%, 5%, 10%, and 15% plasticizer levels;

FIG. 34 shows a glass transition temperature (Tg) curve obtained for a waterborne EVA adhesive comparing an inventive polyester plasticizer and a traditional dibenzoate diblend at 0%, 5%, 10%, and 15% plasticizer levels;

FIG. 35 shows set time results obtained for a waterborne EVA adhesive comparing an inventive polyester plasticizer and a traditional dibenzoate diblend at 0%, 5%, 10%, and 15% plasticizer levels;

FIG. 36 shows open time results obtained for a waterborne EVA adhesive comparing an inventive polyester plasticizer and a traditional dibenzoate diblend at 0%, 5%, 10%, and 15% plasticizer levels;

FIG. 37 shows time-to-fusion results obtained for a PVC melt compound, comparing traditional phthalate plasticizers and three inventive polyester plasticizers, all at 50 phr levels;

FIG. 38 shows Shore A hardness results obtained for a PVC melt compound, comparing traditional phthalate plasticizers and three inventive polyester plasticizers, all at 50 phr levels;

FIG. 39 shows volatile loss results obtained for a PVC melt compound, comparing traditional phthalate plasticizers and three inventive polyester plasticizers, all at 50 phr levels;

FIG. 40 shows extraction resistance results obtained for a PVC melt compound, comparing traditional phthalate plasticizers and three inventive polyester plasticizers, all at 50 phr levels;

FIG. 41 shows gloss results obtained for two vinyl label films comprising 0, 25, 35, and 45 phr of two different inventive polyester plasticizers;

FIG. 42 shows surface energy over time (initial, 1 day, 7 day) results obtained for a vinyl label film comprising an inventive polyester (X-121) at 0, 25, 35, and 45 phr levels;

FIG. 43 shows high humidity/temperature exposure surface energy results obtained for a vinyl label film comprising an inventive polyester (X-121) at 0, 25, 35, and 45 phr levels;

FIG. 44 shows surface energy over time (initial, 1 day, 7 day) results obtained for a vinyl label film comprising another inventive polyester plasticizer (X-124) at 0, 25, 35 and 45 phr plasticizer levels;

FIG. 45 shows high humidity/temperature exposure surface energy results obtained for a vinyl label film comprising another inventive polyester plasticizer (X-124) at 0, 25, 35 and 45 phr plasticizer levels;

FIG. 46 shows the holding power results at one day from a pressure sensitive adhesive (PSA) applied to a vinyl label film comprising two inventive polyester plasticizers (X-121, X-124) at 25, 35 and 45 phr plasticizer levels; and FIG. 47 shows seven day holding power results from a PSA applied to a vinyl label film comprising two inventive polyester plasticizers (X-121. X-124) at 0, 25, 35 and 45 phr plasticizer levels.

DETAILED DESCRIPTION OF THE INVENTION

The invention is directed to oligomeric dibenzoates comprising regularly alternating units of diols and dibasic acids dual end-capped with benzoate esters or end-capped with hybrid benzoate and acetate esters.

The invention is directed in particular to propylene glycol adipate and propylene glycol succinate polyesters end-capped with benzoic acid esters, but is not limited as such. These novel oligomeric dibenzoates are characterized by having little or no free hydroxyl groups, which may be achieved by adding acetic anhydride to the production process. While end-capping and reduction of free hydroxyl groups are not unique processes per se, end-capping propylene glycol adipate and/or propylene glycol succinate polyesters with benzoate esters to form useful plasticizer compositions is heretofore unknown.

If acetic anhydride is added to the process to remove or reduce residual or free hydroxyl groups, polyesters having hybrid benzoate/acetate ester end-caps may be formed. These hybrid benzoate/acetate end-capped polyesters are also useful plasticizer compositions and fall within the scope of the invention. These hybrid end-capped polyesters are also heretofore unknown as plasticizer compositions.

A typical structure for a polyester plasticizer of the invention based on propylene glycol adipate (dual end-capped with benzoic acid) is set forth below:

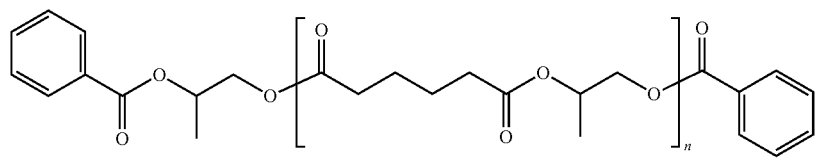

Adipic Acid:Propylene Glycol:Benzoic Acid

A typical structure for the polyester plasticizer of the invention based on propylene glycol succinate (dual end-capped with benzoic acid) is set forth below:

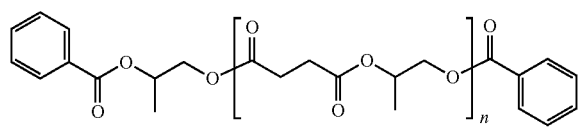

Succinic Acid:Propylene Glycol:Benzoic Acid

While the invention is described primarily with reference to polyesters comprising propylene glycol and succinic or adipic acid, other diols and dibasic acids may be used to form a polyester end-capped with benzoate esters or hybrid benzoate and acetate esters. Diols useful in the inventive compositions, including without limitation 1,3-butane diol, 1,4-butane diol, 1,3-propane diol, and mixtures thereof. Useful dibasic acids include without limitation azelaic, glutaric, sebacic, phthalic and terephthalic acids. Polyesters prepared from these other diols and dibasic acids are also within the contemplation of the invention. Polyesters prepared with certain tribasic acids, such as trimellitic anhydride, are also within the contemplation of the invention.

The moles of glycol (diol), dibasic acid, benzoic acid and acetic anhydride used in preparation of the inventive polyester plasticizers may vary depending on the target molecular weight and on whether an excess of any component is used in preparation of the inventive compositions. The inventive oligomeric plasticizers are characterized by number average molecular weights (Mn) ranging from about 1000 to about 2500, preferably ranging from about 300 to about 1000. Weight average molecular weights (Mw) range from 500 to about 5000. The polydispersity index or uniformity of the inventive oligomeric compositions ranges from about 1.5 to about 3, depending on the reactants ratio, mechanism of polymerization and time of reaction.

For purposes of the invention, the terms "inventive polyester plasticizers" or "inventive oligomeric plasticizer" include either oligomeric dibenzoate end-capped polyester compositions or oligomeric benzoate/acetate end-capped polyester compositions. Other terms, such as "oligomeric dibenzoates" and "oligomeric benzoate/acetate hybrid esters", may also be used to describe the inventive compositions.

"Hybrid" means a polyester of the invention having both benzoate and acetate ester end caps.

Methods of preparing polyesters are generally known in the art. The present invention provides an improved method for preparing inventive oligomeric dibenzoates in a manner that is reproducible and achieves the desired properties. The present inventive method also utilizes a known step of acetic anhydride addition to eliminate or reduce the concentration of residual hydroxyl groups in the process of preparing the inventive oligomeric dibenzoates, which may result in the formation of hybrid, oligomeric benzoate/acetate end-capped polyester compositions. The inventive method is described below in terms of the propylene glycol adipic acid end-capped with benzoic acid, although the method may be used to prepare other inventive polyester plasticizers using diols and dibasic acids as described herein.

As one embodiment, the inventive method provides for charging benzoic acid (538 grams, 4.4 moles), adipic acid (1286 grams, 8.8 moles), propylene glycol (1048 grams, 13.8 moles) and zinc acetate as a catalyst (3.65 grams, 0.2% wt./Acid) to a 3 liter round bottom flask equipped with a magnetic stirrer, distillation column packed with six inch stainless steel mesh, distillation head with a 1 liter collection flask and a nitrogen inlet (100 mL/min.). The reaction mixture was heated to 180° C. and ramped to a temperature of 220° C. at the rate of 10° C./hr. After a minimum two-hour soak at maximum temperature, the pressure was slowly reduced to 120 mm/Hg over about 1 hour and then ramped down from 120 mm-Hg to 7 mm-Hg at approximately 20 mm-Hg/hr. The pressure reduction took about 6 hours. The pressure was allowed to remain at 7 mm-Hg until the acidity was less than <0.3%, or no less than 4 hours at pressure. The product was filtered at 170-180° C. through Whatman filter paper on a Buchner funnel. The product was then allowed to cool to ambient temperature and tested for Gardner color, viscosity, acidity, and polydispersity.

As described above, the inventive method utilizes a $Zn(OAc)_2$ (zinc acetate) catalyst, which is an improvement over prior art methods using halogen-based catalysts for preparing polyesters. The inventive method also introduces early ramping of temperatures of the reaction mixture during the initial (esterification) phase of the process to minimize the presence of free benzoic acid in the reaction mixture, which has a tendency to solidify in the distillation column and condenser. In addition, pressure reduction is begun in the process when the acid number is approximately 5, which also reduces the likelihood of benzoic acid clogging the column.

As discussed herein, a fraction of polyesters produced during the above described process include residual hydroxyl groups, which are incomplete reaction products formed during the preparation of the dual benzoic acid end-capped polyesters of the invention. These undesirable residual hydroxyl groups affect compatibility in use. To facilitate the conversion of the residual hydroxyl end groups to ester end caps and drive the reaction to completion, acetic anhydride may be added to reduce or eliminate the percentage of undesirable free hydroxyl groups formed. As a result of acetic anhydride modification to the preparation process, oligomeric polyesters end-capped with benzoate and acetate esters are formed. Excess acetic anhydride can easily be removed as acetic acid upon contact with water.

The amounts of components and their relative ratios may be adjusted in the inventive method depending on the quantity of inventive material desired properties sought, or the target Mn or Mw.

Sources for components used to prepare the inventive plasticizers are known in the art. Some of the reactants are available from natural sources, thereby allowing for greater natural content and a greener product.

The inventive polyester end-capped compositions may be used as a plasticizer in caulks, sealants, adhesives, vinyl and other polymeric dispersions, where plasticizers are traditionally used.

A large variety of homopolymers and copolymers may be used with the inventive polyester plasticizers. As an example, for adhesives, any of the known polymers that can be formulated into an adhesive can be used in combination with the novel inventive polyester plasticizers to prepare a lower VOC content, environmentally safe and non-hazardous composition in accordance with the present invention. The inventive polyester plasticizers are expected to be particularly useful in a wide variety of waterborne and non-aqueous adhesive polymer compositions. Non-limiting examples of such polymers include, but are not limited to, homopolymers and/or copolymers of: acrylics, polyvinyl acetate, ethylene vinyl acetate, polyacrylates, methacrylates, styrene acrylates, polychloroprenes, polyurethanes, thermoplastic polyurethanes, polysulfides, aminos, epoxies, polyamides, and nitriles. Other polymer-based compositions useful in adhesive applications that traditionally require plasticizers will be known to one skilled in the art.

The inventive polyester plasticizers may also be used in caulks and sealants, for example in sealants based on polysulfides. A typical polysulfide insulating sealant formulation (A side and B side) is disclosed in the examples.

The polyester plasticizers of the present invention can generally be utilized with numerous other thermoplastic, thermoset, or elastomeric polymers. In a preferred embodiment, the inventive polyester plasticizers may be used to prepare a reduced viscosity PVC or acrylic plastisol in accordance with the present invention.

In addition to the materials identified above, other suitable polymeric materials include without limitation homopolymers and copolymers of vinyl acetate, vinylidene chloride, diethyl fumarate, diethyl maleate, polyvinyl butyral, polyurethanes, cellulose nitrate, and various polyacrylates. Particularly suitable acrylic polymer compositions include various polyalkyl methacrylates, such as methyl methacrylate, ethyl methacrylate, butyl methacrylate, cyclohexyl methacrylate, or allyl methacrylate; various aromatic methacrylates, such as for example benzyl methacrylate; or various alkyl acrylates, such as for example methyl acrylate, ethyl acrylate, butyl acrylate, or 2-ethylhexyl acrylate; or various acrylic acids, such as methacrylic acid and styrenated acrylics.

Other polymers for which the inventive polyesters may be useful as a plasticizer include epoxies, phenol-formaldehyde types; melamines; silyl-terminated polyethers and the like. Still other polymers will be evident to one skilled in the art.

The total amount of plasticizer used in any particular polymeric dispersion ranges broadly depending on the particular polymer, the characteristics of the polymer and other components, the process, the application or use and the results desired. By way of example only, in adhesives, generally, plasticizer levels range in amounts from about 1 to about 50 wt. %, preferably from about 5 to about 20 wt. %, based on the weight of the wet adhesive. Preferred embodiments for an adhesive include 10 wt. % in homopolymer polyvinyl acetate (PVA) and 5 wt. % in ethylene vinyl acetate (EVA) copolymers. Other plasticizer levels useful in adhesives are set forth in the examples.

In caulks and sealants, the oligomeric dibenzoate plasticizers of the invention are useful in levels ranging from about 5 to about 40 wt. %, based upon the weight to the total composition. Useful levels are disclosed in the examples.

In plastisols generally, plasticizers are used in amounts from about 30 to about 110, desirably from about 10 to about 100, and preferably from about 20 to about 80 parts by weight for every 100 total parts by weight of the one or more thermoplastic, thermoset, or elastomeric polymer that forms the composition, including without limitation any of the polymers identified above. Non-limiting plastisol formulations are shown in the examples.

The oligomeric dibenzoate plasticizers of the invention are useful in vinyl compositions in amounts ranging from about 5 to about 60 wt. %, based upon the weight of the total composition. Typical vinyl formulations are set forth in the examples.

It is expected that one skilled in the art would be able to arrive at additional acceptable plasticizer levels on the intended use and desired performance in any particular polymeric application.

The inventive polyester plasticizers may be used alone or as a substitute for traditional plasticizers. They may also be, but are not required to be, blended with various other conventional general purpose, specialty and/or secondary plasticizers to enhance or augment properties of polymeric compositions, including but not limited to improving solvating characteristics and compatibility and processability of a plastisol. Blending may be done with a wide variety of conventional plasticizers that include, but are not limited to, phthalate esters, dibenzoate esters, phosphate esters, various adipate, azelate, oleate, succinate and sebacate compounds, terephthalate esters, such as DOTP, 1,2-cyclohexane dicarboxylate esters, epoxy plasticizers, fatty acid esters, glycol derivatives, sulfonamides, and hydrocarbons and hydrocarbon derivatives that are often utilized as secondary plasticizers. Monobenzoates, such as isononyl benzoate, isodecyl benzoate, 2-ethylhexyl benzoate, and 3-phenyl propyl benzoate (3-PPB) and 2,2,4-trimethyl-1,3-pentanediol diisobutyrate, can also be blended with the inventive polyester plasticizers.

As discussed, particularly preferred applications for the inventive polyester plasticizers are in blends of compatible monomeric plasticizers in polysulfide sealants, waterborne PVAc and EVA adhesives, vinyl formulations, such as filled and unfilled plastisols and films, and automotive plastisols. Other use applications are within the scope of the invention and include without limitation other sealants, other waterborne and non-waterborne adhesives, packaging glues, adhesive assemblies, labeling, laminates, envelopes, food packaging materials, wood glue, construction adhesives, transportation product assemblies, electronic product assembly, pressure sensitive adhesive (PSA) applications, caulking, vinyl flooring and melt compounded vinyl, although this list is by no means exhaustive. Still other uses will be evident to one skilled in the art.

Depending on application, the inventive polyester plasticizers may also be combined with or include various amounts of conventional additives such as colorants, surfactants, thickeners, biocides, fillers, polyvinyl alcohol, defoamers, humectants, antioxidants, heat stabilizers, flame retardants, and the like.

The invention is further described in the examples below. While the invention is described in terms of propylene glycol adipate and propylene glycol succinate, end-capped with benzoate or benzoate/acetate esters, the invention is not limited as such. Other diols useful in the invention include without limitation 1,3-butane diol, 1,4-butane diol, and 1,3-propane diol and mixtures thereof. Useful dibasic acids include without limitation azelaic, phthalic, glutaric, sebacic and terephthalic acid. Trimellitic anhydride, a tribasic acid, may also be useful.

EXAMPLES

The inventive polyester plasticizers evaluated in the examples include:

X-121—inventive polyester plasticizer comprising propylene glycol adipate having dual benzoate end-caps X-124—inventive polyester plasticizer comprising propylene glycol adipate having dual benzoate end-caps (higher molecular weight than X-121)

X-151—inventive polyester plasticizer comprising propylene glycol succinate having dual benzoate end-caps X-131—inventive polyester plasticizer comprising propylene glycol adipate having hybrid benzoate and acetate ester end-caps.

Traditional plasticizers used for comparison in the examples include:

Diisononyl phthalate (DINP)

Dioctyl terephthalate (DOTP)

Isononyl benzyl phthalate (INBP)

Trimethyl-1-3-pentanediol monoisobutyrate benzyl phthalate (benzyl 3-isobutyryloxy-1-isopropyl-2,2-dimethylpropyl phthalate or TBP)—a traditional high molecular weight, monomeric alkyl (C12) benzyl phthalate available as Santicizer® 278 from Ferro Corporation.

K-FLEX® 850S (KF850S or 850S)—a dibenzoate diblend of diethylene glycol dibenzoate and dipropylene glycol dibenzoate (DEGDB/DPGDB), commercially available from Emerald Kalama Chemical.

K-FLEX® 975P (KF975P or 975P)—a dibenzoate triblend comprising 80 wt. % of a 4:1 ratio of DEGDB:DPGDB and 20 wt. % of 1,2-propylene glycol dibenzoate (PGDB), commercially available from Emerald Kalama Chemical.

Example 1: 2K Polysulfide Insulating Glass Sealant/B Side Evaluation

The formulation of the sealant and methodologies used in the example are set forth below:

A Side Formulation

| Component Type | PHR |
| --- | --- |
| Liquid polysulfide polymer | 100 |
| INBP | 35 |
| Coupling agent | 1.2 |
| Ground calcium carbonate | 155 |
| Precipitated calcium carbonate | 32 |
| Stearic acid | 1.6 |

B Side Formulation

| Component Type | Parts |
| --- | --- |
| Plasticizer | 155 |
| Curing agent | 101 |
| Carbon black | 33 |
| Accelerator | 6 |

TABLE 1

Methodologies

| | |
| --- | --- |
| A Side Preparation | Weighed out polymer into mixing vessel, then with mixing added remaining liquid components, mixed on speed 1 with paddle mixer until liquids were well mixed (~2 min.) Added filler in portions, making sure each portion was well blended before adding the next. Continued mixing for 20-25 minutes. Checked mixture on Hegman, continued mixing until the Hegman grind was 4 or higher. |
| B Side Preparation | Blended raw materials for 10 minutes at 200 RPM's using a dispersion blade. Ground the dispersed mixture on the three roll mill set at an adequate gap until the grind was greater than 4 on a Hegman grind gauge (3-5 passes). |
| Sealant Preparation | Mixed the A and B side together in a 10:1 volumetric ratio until the mixture was uniform in color. |
| Loop Test | ASTM D3291 |
| Pot Life (Steady Shear to 250 Pa · s) | A timer was started and the two sides were immediately mixed (10:1; A:B) together using a metal spatula. Once mixed completely, the mixture was loaded onto the rheometer. When the run was complete, the time at which the viscosity passed 250 Pa · s was recorded and added to the initial mixing time. The parallel plates were set at a gap of 100 μm and run at a steady shear of 100 s$^{-1}$. |
| Roll Test | A tight loop of sealant was rolled with absorbent paper, then placed in an oven at 60° C. for three days. Compatibility was judged on degree of exudation in sum. |

TABLE 1-continued

Methodologies

| | |
|---|---|
| Shore A Hardness | A sample of 10:1 (A:B) was mixed until color was uniform, then degassed using the three roll mill. The degassed sample was evenly spread into an aluminum weigh pan, which was then covered with a polypropylene sheet. The sample was turned upside down and pressed using a glass plate. After one hour, the polypropylene sheet was removed if possible, then tested using a Shore A hardness tester. The initial hardness value was recorded. Tests were performed every hour between 1-4 hours, then every day up until seven days, followed by weekly measurements. |
| Tensile Strength | Two polypropylene sheets were placed on two glass plates shimmed with three microscope slides. A 10:1 ratio of A:B were mixed until the color was uniform, then degassed using the three roll mill. The sample was then scooped into the center of one of the polypropylene sheets, using caution to avoid introducing bubbles. The sample was then topped with the second polypropylene sheet and glass plate and pressed. After curing 24 hours, the samples were removed. Dogbones were cut using the ASTM D412-C die, then pulled at 19.9 in/min. Tensile strength at break, 100% modulus (flexibility) and elongation % were measured according to known, standard methods. |
| Lap Shear | The A and B components were mixed on a Hobart mixer until uniform, then degassed on the three roll mill. Following the degassing the sealant was applied to 1-2 inches of substrate (either glass or aluminum), then the second substrate (also either glass or aluminum) was applied to the top. The specimen was then placed in a jig following ASTM C961. The specimens were cured at room temperature for two days, then in an oven set at 70° C. for six hours. The specimens were then allowed to condition in the environmental room overnight (at a minimum) before being pulled on the tensile tester. |

Inventive oligomeric dibenzoates based on propylene glycol adipate of different molecular weights (X-121 and X-124) were compared to a traditional high molecular weight benzyl phthalate (TBP) plasticizer in a self-curing, two-part polysulfide-insulating glass type sealant. The inventive plasticizers were incorporated on the B side of the sealant consisting of the catalyst suspended in plasticizer(s).

FIG. 1 shows steady shear (to 100 s$^{-1}$) viscosity results (Pa·s at 30 seconds) obtained for each plasticizer on the B side. The results show that the inventive propylene glycol adipate benzoate oligomers had slightly higher viscosity results, but overall compared favorably to the traditional benzyl phthalate (TBP) in terms of viscosity.

There are two reasons why viscosity is a critical parameter in the B-side. The first is to maintain the suspension of the catalyst during long-term storage. The second requirement is that the viscosities of the A and B sides are closely matched so that they can be easily mixed together.

The stability of the suspension of the B side was measured by centrifuging the control B-side (containing TBP as a plasticizer) and the X-124 experimental blend B-side at 1000 RPM's for one hour and measuring the extent of any separation or solids settling. Neither the control nor the experimental B-side showed any evidence of settling. All had good suspension stability.

Shore A results obtained over time (0-72 hrs) for polysulfide sealants comprising INBP (A-side plasticizer)/TBP (B-side plasticizer) (as a typical polysulfide control), INBP/X-121 and INBP/X-124 plasticizer blends are shown in FIG. 2. The results for all compositions are comparable and show that both of the inventive polyester plasticizer blends are efficient in the polysulfide sealant. The results demonstrate that X-121 and X-124 are good candidates to substitute for a traditional benzyl phthalate in a polysulfide application.

FIGS. 3 and 4 show tensile strength (psi), modulus (100%, psi)) and elongation (%) properties for polysulfide sealant samples comprising the INBP/TBP control, INBP/X-121, 975P/X-121 and 975P1X-124 plasticizer blends at one-day and four weeks, respectively. The 975P was utilized as a phthalate alternative in the A-side. The results show that, over time, the sample containing the inventive oligomeric dibenzoate X-121 in combination with INBP performed comparably to the INBP/TBP control. The results also showed that the X-121 and X-124 polyester plasticizers of the invention combined with the dibenzoate triblend plasticizer performed comparably to the INBP/TBP control as well. These results again demonstrate that X-121 and X-124 are good candidates to substitute for the traditional benzyl phthalate in a plasticizer blend for a polysulfide sealant. They also show that the dibenzoate triblend is a very viable alternative as a plasticizer blend for use on the A-side of a polysulfide sealant.

Roll tests for compatibility were conducted at 60° C. and results (not shown) were obtained for the INBP/TBP control and the INBP/X-124 blend in the polysulfide sealant. The results reflect that the INBP/X-124 blend is slightly less compatible over time (rating of "0" at day 1, "1" at day 2 and "2" at day 3) than the INBP/TBP control (consistent "0" rating). The results, while not perfect, still reflected acceptable compatibility.

Loop test results (not shown) for both samples were rated after 7 days of testing. Both samples rated "0" after 7 days, thus establishing the compatibility of the polyester plasticizer blend in polysulfide applications.

Pot Life—(Time to 250 Pa·s) results were obtained for seven sealant samples comprising: INBP/TBP (control), INBP/X-121, INBP/X-124, 850S/X-121, 850S/X-124, 975P/X-121 and 975P/X-124 plasticizer blends. Results are shown in FIG. 5. The results reflect very similar pot life for the X-124 blends as compared to the INBP/TBP control. Results for the X-121 blends reflect a shorter pot life, indicating that this plasticizer could be used in sealants needing an accelerated cure cycle.

Lap shear and maximum shear stress show the strength of the sealant bond. Lap shear results (stress at break, psi) were obtained for the INBP/TBP control, INBP/X-121, 975P/X-121 and 975P/X-124 blends of aluminum to aluminum (Al/Al), glass to glass (Gl/Gl) and aluminum to glass (Al/Gl) samples. The results shown in FIG. 6 reflect very similar performance between the samples evaluated, with the inventive oligomeric benzoates showing comparable or better results over the INBP/TBP control blend.

Overall, the results above show that the inventive oligomeric dibenzoates plasticizers performed very well in polysulfide applications and provide a viable alternative over traditional phthalate plasticizers.

Example 2—Propylene Glycol/Succinate Polyester with Dual Dibenzoate End Caps in Plastisol Additional Methodology used for Plastisol Evaluations:

Viscosity and Rheology: Low shear—Brookfield RVT, 20 RPM's, 10 revolution reading. ASTM D1823. High shear—TA AR2000ex used. Parallel plates were set at appropriate gap. Shear to 1000 sec$^{-1}$.

Gel/Fusion: TA AR2000ex in oscillatory mode. Parallel plates were set at appropriate gap. The test temperature was started at 40° C. and heated at a rate of 5° C./minute to 220° C.

Compatibility of the plasticizer with the polymer: Roll and Loop Tests, as above in Table 1.

Efficiency-Shore A—ASTM D2240; Tensile—ASTM D638, Type IV die, 50.8 cm/minute pull rate.

Raw Materials for Plastisol Evaluations:

Geon™ 121-A—PVC homopolymer available from PolyOne Corporation.

KRONOS TiO$_2$—Titanium dioxide available from Kronos, Inc.

Mark® 1221—Ca/Zn stabilizer available from Galata Chemicals.

Medusa Carb 18—Calcium carbonate filler available from Medusa Corporation.

X-151 Results—TBP was compared to the succinate-based propylene glycol oligomeric dibenzoate (X-151) in the standard underbody (UB) "filled" sealant plastisol formulation set forth below in Table 2:

TABLE 2

| Underbody (UB) "Filled" Sealant Plastisol | |
|---|---|
| Raw Material | PHR |
| PVC (Geon™ 121A) | 100 |
| Plasticizer | 100 |
| Filler (Medusa Carb 18) (calcium carbonate filler) | 100 |

A Loop Test for compatibility with the PVC polymer was conducted for the TBP control and X-151 samples with readings taken at 4 hours, 1 day, 1 week, 2 weeks and 4 weeks as set forth in FIG. 7. The TBP plastisol had a reading of "0" at all times, indicating excellent compatibility. X-151 plastisol had a rating of "0" at four hours and 1 day. A rating of "1" was recorded at 1 week, 2 weeks and 4 weeks, reflecting good compatibility with the polymer. The results show that X-151 is a viable alternative plasticizer for this application.

Initial shear results (400 gap) are shown in FIG. 8 for both the TBP and X-151 plastisol samples. The X-151 plasticizer sample had higher initial viscosity. One-day and three-day shear results are shown in FIGS. 9 and 10, which reflect good viscosity and stable rheology for the X-151 sample over time as compared with a traditional industry phthalate.

Gel fusion data shows the relative solvation characteristics of plasticizers. Gel/fusion curves were obtained for the TBP and X-151 plastisols. The results shown in FIG. 11 demonstrate that the inventive oligomeric dibenzoate has very good solvation characteristics when compared with the industry standard phthalate, TBP.

X-151 was also evaluated in a 100 phr "unfilled" PVC plastisol of the formulation set forth below in Table 3.

TABLE 3

| Standard Unfilled Plastisol | |
|---|---|
| Raw Material | PHR |
| Geon™ 121A (PVC homopolymer) | 100 |
| Plasticizer | 100 |
| Mark® 1221 (Ca/Zn stabilizer) | 3 |

A Loop test was conducted on the plastisol and ratings were made at 4 hours, 1 day and 1 week. X-151 had a "0" rating at 4 hours and 1 day. The rating increased to "1" at 1 week. The data (not shown) reflected good compatibility with the PVC polymer.

A Roll test was conducted and ratings were made at 1 day, 2 days, and 3 days (data not shown). X-151 had a rating of "0" at 1 day, which increased to about "2" at 2 days and 3 days. While not perfect, the data reflected acceptable compatibility with the PVC polymer.

Example 3—Propylene Glycol/Adipate Polyester with Dual Dibenzoate End Caps in Plastisol—Initial Screen The adipate-based inventive plasticizer (X-121) was compared to the high molecular weight, monomeric benzyl phthalate plasticizer TBP in the standard unfilled plastisol formulation shown above in Table 3.

Both plasticizers were utilized at 100 phr levels.

Methodologies utilized are the same as in Example 2 above.

Viscosity levels (mPa·s) obtained for the two plastisols (initial, one-day and three-day) are shown in FIG. 12 and reflect that the inventive plasticizer (X-121) surprisingly is stable in vinyl at a lower viscosity than the phthalate ester.

Initial, one-day shear and three-day shear results obtained for the unfilled plastisol samples are shown in FIGS. 13-15, respectively, and reflect very good, stable rheology characteristics for the inventive adipate-based oligomeric dibenzoate (X-121).

Surprisingly, despite being a higher molecular weight oligomeric molecule, the gel fusion curve comparing the two plastisols (shown in FIG. 16) reflects very similar results for the inventive plasticizer (X-121) and the traditional benzyl phthalate (TBP) plastisols, which is surprising.

The compatibility roll test shown in FIG. 17 reflects a higher rating for the plastisol sample comprising inventive plasticizer X-121, while the compatibility loop test in FIG. 18 reflects almost identical results for the inventive plasticizer. Based on these results, the inventive oligomeric dibenzoate X-121 was deemed to be compatible in the PVC plastisol.

The inventive plasticizer (X-121) was compared to the same industry standard phthalate ester plasticizer, TBP, in the standard "filled" PVC plastisol formulation shown in Table 2, above. Both plasticizers were utilized at levels of 100 phr.

Viscosity levels (mPa·s) obtained for the two plastisols at initial, one-day, three-day and seven-day intervals are shown in FIG. 19. Surprisingly, X-121, despite the fact that it is a high solvator, was found to be stable in vinyl at a lower viscosity than the phthalate ester.

Initial and one-day shear rates obtained for the filled plastisol samples are shown in FIGS. 20 and 21. The results demonstrate good rheological characteristics for the adipate-based oligomeric dibenzoate X-121.

The gel fusion curve (FIG. 22) reflects similar gel/fusion characteristics for the inventive plasticizer (X-121) versus the higher molecular weight phthalate ester.

The compatibility roll data (not shown) for the inventive X-121 plasticizer in the filled plastisol composition was rated "1" as compared to the phthalate ester which rated "0". The compatibility loop data (not shown) for both plasticizers in the filled composition was "0".

Overall, the above results obtained for the inventive adipate-based oligomeric dibenzoate plasticizer (X-121) reflect good compatibility and comparable rheology characteristics as compared to the phthalate (TBP) control, with enhanced solvation and viscosity characteristics. The results show that the inventive plasticizers are very good substitutes for higher molecular weight traditional phthalate ester plasticizers.

In the case of the polysulfide sealant evaluation (Example 1), the inventive oligomeric dibenzoate plasticizers offer good compatibility with the polysulfide polymer, enhanced by the polarity of the benzoic acid end caps.

Example 4—Hybrid Benzoate/Acetate End-Capped Plasticizers in a Plastisol

Methodology:
Soak Test:
Extraction in Water:

Cut out three 2×2" circles for each sample, labeled by cutting notches for reference. Weigh the samples. Submerge each sample in 100 mL of water in separate jars at 70° C. for seven days, making sure that the samples do not float. Dry samples with a Kimwipe and weigh them. Place the samples in an oven at 70° C. for four hours to completely dry, followed by reweighing once cooled.

Heat/Humidity Test:

Weigh the samples. Hang the samples from paper clips above 50 mL of water in a closed 32 oz. jar. Place jar in an oven at 70° C. for seven days. Wipe off with a Kimwipe and weigh each sample on an analytical balance. Place the samples in an oven at 70° C. for four hours to completely dry, followed by reweighing once cooled.

The process for preparing the inventive polyester end-capped plasticizer compositions was modified to reduce free or unreacted, residual hydroxyl content by adding acetic anhydride to the preparation process. The resulting inventive hybrid (benzoate/acetate end-caps) plasticizer had reduced hydroxyl content and was less prone to water extraction and reactivity in use applications. An evaluation comparing the inventive adipate-based oligomeric dibenzoate plasticizers prepared without acetic anhydride in the process (X-121) with the inventive oligomeric hybrid benzoate/acetate end-capped polyester plasticizer prepared with acetic anhydride in the process (X-131) was conducted using a basic PVC plastisol formulation set forth below in Table 4.

TABLE 4

| Raw Material | PHR |
| --- | --- |
| Geon ™ 121A (PVC homopolymer) | 100 |
| Plasticizer | 100 |
| Medusa Carb 18 | 100 |
| KRONOS $TiO_2$ | 10 |
| Mark ® 1221 (Ca/Zn stabilizer) | 3 |

The plastisol was prepared by mixing the above components on a Hobart mixer (speed 1) for 10 minutes; the formulation was then degassed while mixing for an additional 10 minutes. Physical data for plastisols comprising inventive oligomeric dibenzoate plasticizers prepared with (X-131) and without (X-121) acetic anhydride in the process were obtained and compared. The results are set forth in the tables below. Data was obtained for a number of samples and averaged as set forth below in Tables 5-7.

TABLE 5

Soak Test, 70° C. Data

| Sample | Average % Weight Change |
| --- | --- |
| X-131 | −0.002 |
| X-121 | −0.029 |

TABLE 6

Viscosity

| | Viscosity (mPa · s) | | | Temp (° C.) | | |
| --- | --- | --- | --- | --- | --- | --- |
| Plasticizer | Initial | 1-Day | 7-Day | Initial | 1-Day | 7-Day |
| X-121 | 74400 | 71000 | 83000 | 23.4 | 23.5 | 22.9 |
| X-131 | 45600 | 46200 | 50600 | 23.1 | 23.3 | 22.7 |

TABLE 7

Heat/Humidity Test

| Sample | Mass Difference |
| --- | --- |
| X-121 | −0.4% |
| X-131 | −0.2% |

The results above show that the inventive oligomeric polyester plasticizers prepared by adding acetic anhydride to the preparation process had a greater resistance to extraction by water and acceptable compatibility. This will result in better longer term performance in PVC applications where exposure to weathering is expected. Additionally, since the plasticizer will not be as easy to extract, it can perform better as a plasticizer (continue to soften properly).

Example 5—Waterborne Adhesive Evaluation in PVAc

Methodology:
Viscosity—as above in Example 2.

Glass Transition Temperature: DSC Glass Transition Method: 10 mil (wet) films were drawn down on glass and left to dry overnight. After 24 hours, the films were removed from the plates and approximately 10 mg were placed in a closed aluminum DSC pan. The temperature was equilibrated at −75° C., then ramped at 5° C./min to 65° C. Glass transition was measured as the onset of Tg.

Set Time: Set time determinations were made using two strips of 50 lb. unbleached Kraft paper measuring 1"×14" (top piece) and 1.5"×14" (bottom piece). A small amount of adhesive was applied to the bottom strip, and a #20 wire wound rod metered the adhesive onto the bottom strip while a #16 wire wound rod (rubber banded to the #20) simultaneously pressed down the top strip. A timer was then immediately started and the strips were pulled apart until significant force was required to tear apart the strips and fiber tear was noted. Time at this point was recorded as the set time. A minimum of three repetitions were performed. Evaluations were performed blind.

Open Time: A 1.5"×14" piece of 50 lb. unbleached Kraft paper was placed on a glass surface, with a 1"×14" piece of Kraft clipped to its top, rolled back so that the bottom piece was left uncovered. The top piece was sandwiched between a #0 and a #14 wire wound rod with the #0 on top. A small amount of adhesive was applied to the top of the bottom strip and a #20 wire wound rod metered out the adhesive over the entire strip. A timer was started, and at a specified time interval (with intervals of 5 seconds) the top strip was laminated to the bottom using the #0 rod. The strips were then peeled apart and assessed for adhesion and fiber tear. This process was repeated until a specific time interval was confirmed in duplicate as the last time interval to result in significant fiber tear/adhesion. Evaluations were performed blind.

The adipate-based inventive polyester end-capped with benzoic acid esters (X-121) was evaluated in two waterborne adhesives and compared to a traditional dibenzoate (diethylene glycol dibenzoate/propylene glycol dibenzoate) diblend (K-FLEX® 850S or KF850S, an industry standard for use in adhesives). The waterborne adhesive utilized in this evaluation was polyvinyl acetate homopolymer (PVAc) (PACE® 383 by Fuller). X-121 and KF850S were compared at levels in PVA of 5, 10, 15 and 20% by weight, wet.

FIG. 23 shows initial viscosity measurements (mPa·s) obtained for X-121 and KF850S PVAc samples. The results reflect comparable viscosity, with a lower viscosity achieved by the X-121 PVAc samples at the 15 and 20 weight percent levels. Even so, the viscosity for X-121 is still good. The results suggest that X-121 is less efficient; however, these results are useful as a formulation tool as less water would be needed to achieve a processing viscosity. In this way, the adhesive with X-121 can have a higher solids content at comparable viscosity/performance levels.

Viscosity measurements (mPa·s) at one-day, three-day and seven-day (FIGS. 24, 25 and 26 respectively) were obtained for both PVAc samples. The results showed that inventive X-121 plasticizer has comparable viscosity stability over time as compared to a traditional dibenzoate diblend (KF850S) used in adhesives.

Glass transition temperatures (Tg) obtained for the PVAc samples are reflected in FIG. 27. Glass transition temperature is the temperature at which mechanical properties of a plastic (adhesive) change radically. As such, it defines the temperature range to which the adhesive may be exposed. The results reflect similar Tg at 5 wt. % levels. At higher plasticizer levels, results are comparable but with a demonstrated advantage for the dibenzoate blend plasticizer in cold temperatures at higher plasticizer levels. Even so, the X-121 sample still depresses Tg effectively to make it very useful in adhesive products.

Set and open times (sec.) obtained for the PVAc samples are reflected in FIGS. 28 and 29, respectively. Set times are comparable over the levels evaluated. Open times with X-121 were lower than for the dibenzoate diblend. These properties are important as formulation tools to tailor the properties achieved with each plasticizer to a particular application.

Example 6—Waterborne Adhesive Evaluation in EVA

The plasticizers (X-121 and KF850S) of Example 5 were evaluated and compared in an ethylene vinyl acetate copolymer adhesive (EVA) (Elvace® 735 by Fuller) at 5, 10 and 15% by weight, wet.

FIG. 30 shows initial viscosity measurements (mPa·s) obtained for X-121 and KF850S samples. The results reflect lower viscosity for the X-121 plasticizer as plasticizer levels increased at the 10 and 15 weight percent levels.

Viscosity measurements (mPa·s) at one-day, three-day and seven-day (FIGS. 31, 32 and 33, respectively) were obtained for both samples. The results reflect that the inventive X-121 plasticizer had comparable or better viscosity stability over time as compared to the traditional dibenzoate diblend.

Glass transition temperatures (Tg) obtained for the samples are reflected in FIG. 34. The results show a slight advantage in Tg suppression for the traditional dibenzoate at cold temperatures, but results are still comparable.

Set and open times (sec.) obtained for the samples are reflected in FIGS. 35 and 36 respectively. Comparable results were obtained for both samples.

Example 7—Melt Compound Evaluation

Methodology:

Extraction: ASTM D1239. Extractants—Peanut oil (24 hour exposure at RT); 1% IVORY soap solution (24 hours at 50° C. and 4 hours dry at 50° C.); heptane at RT (24 hours, 4 hours dry at 50° C.).

Shore A Hardness: as above in Table 1.

Time to Fusion: The amount of time until the composition becomes a clear, fused mass.

Volatile Loss: ASTM 1203-10 or other standard test known to one skilled in the art.

Raw Materials for Example 7 and 8 Evaluations:

AC® 629 A—low density oxidized polyethylene homopolymer available from Honeywell Additives.

Atomite—fine grain calcium carbonate powder available from various suppliers.

Formolon® 622 R—a medium to low molecular weight PVC homopolymer available from Formosa Plastics.

Therm-Chek® SP 175—liquid barium zinc stabilizer available from by Ferro Corporation.

A melt compound evaluation was conducted using the basic melt compound formulation set forth in Table 8 below.

TABLE 8

| Raw Material | PHR |
| --- | --- |
| Formolon ® 676 | 100 |
| Plasticizer | 50 |
| Stearic Acid | 0.5 |
| Heat Stabilizer, Mark ® 1221 | 3 |

The following plasticizers were evaluated: DINP, DOTP, X-121, X-124 and X-131. All plasticizers were used at 50 phr.

Time to fusion (minutes) results (mill fusion) obtained for the samples are reflected in FIG. 37. All of the inventive polyester plasticizers had better (lower) fusion times as compared to the traditional phthalate plasticizers, DINP and DOTP, which is an advantage over typical polymeric plasticizers that are slower to fuse.

Shore A hardness results obtained initially and at 10 seconds for each sample are set forth in FIG. 38. Results reflect higher Shore A hardness results for compounds comprising the inventive plasticizers as compared to the phthalate samples.

Volatile Loss (%) results obtained for each sample at 1, 3, 7, 14 and 28 days are set forth in FIG. 39. The results show that all three inventive plasticizers performed the same, but all three had a greater loss (of plasticizer) as compared to the traditional phthalates likely due to some low molecular weight fractions inherent in polymeric plasticizers. Overall, due to the high molecular weights of the inventive polyester plasticizers, volatility in the long term is expected to be low, after the lower molecular weight fractions volatilize off.

As shown in FIG. 40, the inventive plasticizers demonstrated excellent extraction resistance in heptane, soapy water and peanut oil as compared to the two phthalates.

Example 8—Vinyl Label Film Evaluation

Methodology:

Surface Energy (ASTM D2578)—This test measured long term surface energy retention over time of a vinyl film, measured initially, at one day and seven days, at 23° C. and 50% relative humidity (RH). The test simulates aging. A high humidity/temperature evaluation was also conducted by hanging the film in a bottle over water at 60° C. overnight, followed by surface energy testing. These tests are indicators of aging and compatibility and resistance to water extraction as well as printability of the vinyl film.

Gloss: ASTM 2243.

PSA Migration Testing—A simple PSA with 30% AQUATAC™ 6085 resin (available from Arizona Chemical) and 70% EPS® 2113 polymer (available from Engineered Polymer Solutions) was prepared. Tapes were prepared using PVC film prepared with the formulation set forth in Table 9, using 0, 25, 35 and 45 phr of the X-121 and X-124 plasticizers. Plasticizer migration is determined by loss of holding power of the adhesive as plasticizer load increases in the vinyl film. Holding power strength (1" wide, 1 kg weight) was measured at 1 day (Room Temperature (RT), dry) cure and accelerated 7 day (60° C. in oven) cure.

A vinyl label film was prepared using the formulation set forth in Table 9 below.

TABLE 9

| Raw Material | Type | PHR |
| --- | --- | --- |
| Formolon® 622R | PVC | 100 |
| Plasticizer | Plasticizer | 0, 25, 35, 45 |
| Atomite | Filler | 15 |
| AC® 629A | Wax | 0.3 |
| Therm-Chek® SP-175 | Heat stabilizer | 3 |
| KRONOS® TiO$_2$ | Pigment | 10 |

Film Preparation: The formulation was prepared by mixing the above components in a Hobart kitchen mixer for 10 minutes at speed "1". Mill settings were 320° F., at 8 minutes with 3 rebandings. Exit gap=0.20 mm (~8 mil). Press settings: Plates were heated at 400° F. for 30 minutes. Around 4 grams of sample was placed between two pieces of 1 mil Mylar, and the Mylar/sample/Mylar was placed between the heated plates. Press cycle: Three minutes at 2000 lbs., released for 10 seconds. Twenty seconds at 2000 lbs., release for 10 seconds. Switch to high pressure for twenty seconds at 40 tons, release for 10 seconds, repeat. Two minutes at 40 tons. Cooling under 40 tons of pressure down to 180° F. (water+air until 350° F., then just water cooling). Immediate removal of pressed vinyl from plates and Mylar.

Vinyl film comprising two inventive oligomeric dibenzoates (X-121 and X-124) was prepared as above in Table 9. Gloss results at 0, 25, 35 and 45 phr plasticizer levels were obtained and are shown in FIG. 41. The results show acceptable fusion and compatibility with the vinyl film.

Surface energy over time results (23° C./50% RH) for the X-121 film samples are shown in FIG. 42, and accelerated results (60° C./high humidity) initially and at 1 day are shown in FIG. 43. Surface energy over time results (23° C./50% RH) for the X-124 samples are shown in FIG. 44, and accelerated results (60° C., high humidity) initially and at 1 day are shown in FIG. 45. Surface energy over time results for the two inventive oligomeric dibenzoates demonstrate an advantage over prior art plasticizers used in this application. The results show unexpected retention of surface energy over time demonstrating the usefulness of the inventive plasticizers for printable vinyl film, even under high temperature and high humidity conditions.

Plasticizer migration results (at 1 day, 23° C./RH) obtained for both the X-121 and X-124 samples are set forth in FIG. 46 using a simple PSA. As noted above, plasticizer migration is determined by a change in adhesive holding power as the plasticizer concentration increases. No indication of migration was noted under 24 hour/room temperature conditioning.

Plasticizer migration results (at 7 days, 60° C.) obtained for both the X-121 and X-124 samples are set forth in FIG. 47. Less migration was noted in the X-124 samples as compared to the X-121 samples, but results were acceptable for both samples.

While in accordance with the Patent Statutes, the best mode and preferred embodiments have been set forth; the scope of the invention is not limited thereto, but rather by the scope of the attached claims.

What is claimed is:

1. A vinyl label film comprising:
   a. a polymer that is polyvinyl chloride, and,
   b. a polyester plasticizer that is propylene glycol adipate end-capped with benzoic acid esters or propylene glycol succinate end-capped with benzoic acid esters, present in amounts up to about 45 parts by weight based upon 100 parts by weight of polyvinyl chloride,
   wherein the vinyl label film is characterized by a surface energy (dynes/cm) over time of greater than about 34, and
   wherein the surface energy over time is retained under high temperature and humidity conditions.

2. A two-part polymeric sealant composition, having an A side and a B side, comprising:
   a. a polysulfide polymer present in the A side of the two-part polymeric sealant, and
   b. a polyester plasticizer that is a propylene glycol adipate end-capped with benzoic acid esters or a propylene glycol succinate end-capped with benzoic acid esters present in the B side of the two-part polymeric sealant,
   wherein the polyester plasticizer has a Mw in the range of at least about 500 to about 5000.

3. A polymeric adhesive composition, comprising:
   a. a polymer that is polyvinyl acetate or ethylene vinyl acetate, and
   b. a polyester plasticizer that is propylene glycol adipate end-capped with benzoic acid esters or propylene glycol succinate end-capped with benzoic acid esters,
   wherein the polyester plasticizer is present in the polymeric adhesive composition in amounts ranging from about 5 to about 20 wt. %, based on the weight of the wet adhesive.

4. A plastisol comprising:
   a. a polyvinyl chloride homopolymer or copolymer or an acrylic-based polymer, and b. a polyester plasticizer comprising propylene glycol adipate end-capped with benzoic acid esters or propylene glycol succinate end-capped with benzoic acid esters, wherein the polyester plasticizer is present in amounts ranging from about 30 to 110 parts by weight for every 100 parts by weight of the polyvinyl chloride homopolymer or copolymer or acrylic-based polymer.

* * * * *